US007598255B2

(12) United States Patent
Dvorak

(10) Patent No.: US 7,598,255 B2
(45) Date of Patent: Oct. 6, 2009

(54) PYRIMIDINE COMPOUNDS AS SEROTONIN RECEPTOR MODULATORS

(75) Inventor: Curt A. Dvorak, San Diego, CA (US)

(73) Assignee: Janssen Pharmaceutica NV (BE)

( * ) Notice: Subject to any disclaimer, the term of this patent is extended or adjusted under 35 U.S.C. 154(b) by 0 days.

(21) Appl. No.: 11/460,294

(22) Filed: Jul. 27, 2006

(65) Prior Publication Data

US 2007/0032481 A1 Feb. 8, 2007

Related U.S. Application Data

(60) Provisional application No. 60/705,719, filed on Aug. 4, 2005.

(51) Int. Cl.
| | |
|---|---|
| A61K 31/519 | (2006.01) |
| C07D 471/04 | (2006.01) |
| C07D 487/04 | (2006.01) |
| C07D 491/04 | (2006.01) |
| C07D 239/28 | (2006.01) |
| C07D 239/72 | (2006.01) |
| C07D 239/42 | (2006.01) |
| C07D 487/08 | (2006.01) |
| C07D 401/04 | (2006.01) |
| C07D 403/04 | (2006.01) |
| C07D 413/04 | (2006.01) |
| C07D 417/04 | (2006.01) |
| C07D 419/04 | (2006.01) |

(52) U.S. Cl. ............ 514/264.1; 544/229; 544/249; 544/250; 544/253; 544/280; 544/295; 544/279; 544/242; 544/284; 544/283; 540/578

(58) Field of Classification Search ........ 514/215, 514/228.2, 228.5, 234.2, 234.5, 252.17, 252.16, 514/264.1, 266.1, 265.1; 540/578; 544/57, 544/61, 62, 69, 115, 116, 117, 229, 249, 544/250, 253, 279, 280, 333, 334, 335

See application file for complete search history.

(56) References Cited

U.S. PATENT DOCUMENTS

| | | | |
|---|---|---|---|
| 3,312,716 | A | 4/1967 | Biel et al. |
| 3,969,355 | A | 7/1976 | Schwan |
| 4,007,196 | A | 2/1977 | Christensen et al. |
| 4,136,193 | A | 1/1979 | Bogeso et al. |
| 4,314,081 | A | 2/1982 | Molloy et al. |
| 4,536,518 | A | 8/1985 | Welch et al. |
| 4,576,604 | A | 3/1986 | Guittard et al. |
| 4,673,405 | A | 6/1987 | Guittard et al. |
| 4,857,330 | A | 8/1989 | Stephens et al. |
| 5,137,890 | A | 8/1992 | Sanfilippo et al. |
| 5,405,848 | A | 4/1995 | Sanfilippo et al. |
| 5,997,905 | A | 12/1999 | McTeigue et al. |
| 6,025,367 | A | 2/2000 | Forbes et al. |
| 6,149,943 | A | 11/2000 | McTeigue et al. |
| 6,355,642 | B1 | 3/2002 | Koyama et al. |
| 6,407,112 | B1 | 6/2002 | Koyama et al. |
| 6,414,149 | B1 * | 7/2002 | Chu-Moyer et al. ......... 544/295 |
| 2002/0183519 | A1 | 12/2002 | Nar et al. |
| 2003/0153728 | A1 | 8/2003 | Kolb et al. |
| 2004/0229874 | A1 | 11/2004 | Bright et al. |
| 2005/0119295 | A1 | 6/2005 | Carruthers et al. |
| 2005/0232986 | A1 | 10/2005 | Brown et al. |
| 2005/0288355 | A1 | 12/2005 | Mork et al. |
| 2006/0194837 | A1 | 8/2006 | Carruthers et al. |
| 2006/0287292 | A1 | 12/2006 | Carruthers et al. |
| 2006/0293316 | A1 | 12/2006 | Apodaca et al. |
| 2007/0260057 | A1 | 11/2007 | Deng et al. |
| 2008/0004258 | A1 | 1/2008 | Keith et al. |
| 2008/0045508 | A1 | 2/2008 | Allison et al. |
| 2008/0045509 | A1 | 2/2008 | Allison et al. |

FOREIGN PATENT DOCUMENTS

| | | |
|---|---|---|
| EP | 1264820 A1 | 12/2002 |
| EP | 1211246 B1 | 2/2004 |
| JP | 03 148265 A | 6/1991 |
| JP | 03148265 * | 6/1991 |
| WO | WO 95/29909 A1 | 11/1995 |
| WO | WO 96/32944 A1 | 10/1996 |
| WO | WO 97/29097 A1 | 8/1997 |
| WO | WO 97/47601 A1 | 12/1997 |
| WO | WO 97/48681 A1 | 12/1997 |
| WO | WO 97/49695 A1 | 12/1997 |
| WO | WO 98/31354 A3 | 7/1998 |
| WO | WO 99/24022 A3 | 5/1999 |
| WO | WO 00/32173 A1 | 6/2000 |
| WO | WO 00/37082 A1 | 6/2000 |
| WO | WO 00/56712 A1 | 9/2000 |
| WO | WO 00/59510 A1 | 10/2000 |

(Continued)

OTHER PUBLICATIONS

Appell, et al., Bioorganic & Medicinal Chemistry (2002), 10(5), 1197-1206.*
Herrera, et al., Magnetic Resonance in Chemistry (2002), 40(4), 293-299.*
Garcia Martinez, et al., Tetrahedron (1998), 54(18), 4607-4614.*
Kawamura, et al., Bioscience, Biotechnology, and Biochemistry (1992), 56(11), 1897-9.*
Collier, et al., Science of Synthesis (2004), 19, 403-425.*
Voitenko, et al., Phosphorus, Sulfur and Silicon and the Related Elements (2005), 180(1), 163-177.*
Herrera, et al., Tetrahedron Letters (2003), 44(10), 2149-2151.*
Herrera, et al., Tetrahedron (2002), 58(19), 3755-3764.*
Lafferty, et al., Journal of Organic Chemistry (1967), 32(5), 1591-6.*
Poyurovsky, et al., Euro. Neuropsychopharmacol. 13 (2003) 123-128.*
Kim, et al., Molec. & Cellular Probes (2000) 14, 47-52.*
Khawam, et al., Cleveland Clinic J. Med., vol. 73, # 4, Apr. 2006, 351-361.*

(Continued)

*Primary Examiner*—Mark L Berch
*Assistant Examiner*—Cecilia M Jaisle
(74) *Attorney, Agent, or Firm*—Michael J. Atkins

(57) ABSTRACT

Certain pyrimidine-containing compounds are serotonin receptor modulators useful in the treatment of serotonin-mediated diseases.

11 Claims, No Drawings

FOREIGN PATENT DOCUMENTS

| WO | WO 00/73299 A1 | 12/2000 |
|---|---|---|
| WO | WO 01/29029 A1 | 4/2001 |
| WO | WO 01/41766 A1 | 6/2001 |
| WO | WO 01/57039 A1 | 8/2001 |
| WO | WO 02/14314 A2 | 2/2002 |
| WO | WO 02/062788 A1 | 8/2002 |
| WO | WO 02/072558 A1 | 9/2002 |
| WO | WO 02072558 * | 9/2002 |
| WO | WO 03/035070 A1 | 5/2003 |
| WO | WO 03/053330 A2 | 7/2003 |
| WO | WO 03053330 * | 7/2003 |
| WO | WO 2004/011467 A1 | 2/2004 |
| WO | WO 2004011467 * | 2/2004 |
| WO | WO 2004094419 * | 4/2004 |
| WO | WO 2004/039786 A1 | 5/2004 |
| WO | WO 2004039786 * | 5/2004 |
| WO | WO 2004/094419 A1 | 11/2004 |
| WO | WO 2005/005387 A1 | 1/2005 |
| WO | WO 2005/030132 A2 | 4/2005 |
| WO | WO 2005/056056 A3 | 6/2005 |
| WO | WO 2006/016262 A1 | 2/2006 |
| WO | WO 2008/013556 A1 | 1/2008 |

OTHER PUBLICATIONS

Mendelson, J. Clin. Psychiatry 2005: 66, 469-476.*
Silvestre, et al., Methods Find Exp Clin Pharmacol 2005, 27(5): 289.*
Kast, Support Care Cancer (2001) 9:469-470.*
Naranjo, et al., Addiction, vol. 90, # 7, pp. 893-905, Jul. 1995.*
May, et al., J. Pharmacol. & Experim. Therap., Apr. 3, 2003.*
PCT International Search Report for International Application No. PCT/US2006/029437 dated Dec. 14, 2006.
Appell, M. et al. An analysis of the binding of cocaine analogues to the monamine transporters using tensor decomposition 3-D QSAR. Bioorg. Med. Chem. 2002, 10(5), 1197-1206.
Berge, S.M. et al. Pharmaceutical Salts. J. Pharm. Sci., 1977, 66:1-19.
Bonhaus, D.W. et al. RS-127443: A selective, high affinity, orally bioavailable 5-HT 2B receptor antagonist. Br. J. Pharmacol. 1999, 127(5), 1075-1082.
DeRuiter, J. et al. Investigation of the Synthesis and Analgesic Activity of 1-Substituted 4-(Propananilido)perhydroazepines. J. Het. Chem. 1992, 29(4), 779-786.
Dube, H. et al. Synthesis of chiral alpha-aminoalkylpyrimidines using an enantioselective three-component reaction. Synthesis 2004, 12, 2015-2025.
Herrera, A. et al. $^1$H and $^{13}$C NMR spectral assignments of 2,4-diaryl-substituted cycloalkyl[d]pyrimidines. Magn. Reson. Chem. 2002, 40(4), 293-299.
Herrera, A. et al. On the mechanism of reaction between ketones and nitriles. Unexpected results from benzyl nitriles. Tetrahedron 2002, 58(19), 3755-3764.
Hoyer, D. et al. Molecular, Pharmacological and functional diversity of 5-HT receptors. Pharmacol. Biochem. Behav. 2002, 71, 533-554.
Jerman, J.C. et al. Pharmacological characterisation of human 5-HT$_2$ receptor subtypes. Eur. J. Pharmacol. 2001, 414, 23-30.
Kawamura, S. et al. Fused heterocycles, furo[3,2-d]pyrimidines and dihydrocyclopenta[d]pyrimidines, as potential new herbicides. Biosci. Biotechnol. Biochem. 1992, 56(11), 1897-1899.
Porter, R.H. et al. Functional characterization of agonists at recombinant human 5-HT$_{2A}$, 5-HT$_{2B}$ and 5-HT$_{2C}$ receptors in CHO-K1 cells. Br. J. Pharmacol. 1999, 128, 13-20.
Roth, B.L. et al. The Multiplicity of Serotonin Receptors: Uselessly Diverse Molecules or an Embarrassment of Riches? Neuroscientist 2000, 6(4), 252-262.
Sanfilippo et al. Novel tetrahydropyrido[4,3-d]pyrimidines as gastric antilesion agents. Eur. J. Med. Chem. 1992, 27(7), 655-661.
Schotte, A. et al. Risperidone compared with new and reference antipsychotic drugs: in vitro and in vivo receptor binding. Psychopharmacology 1996, 124, 57-73.
Stolle, W.A.W. et al. Intramolecular Diels-Alder reactions of pyrimidines: Synthesis of tricyclic annelated pyridines. Tetrahedron 1989, 45(20), 6511-6518.
Voitenko, Z.V. et al. Conversions of 2-(2-oxocycloehxylcarbonyl)benzoic acid derivatives to pyrazolo[5,1-a]isoindole and pyrimidine rings. Phosphorus, Sulfur Silicon Relat. Elem. 2005, 180(1), 163-177.
U.S. Appl. No. 60/938,790, filed May 18, 2007, Keith.
U.S. Appl. No. 11/939,881, filed Nov. 14, 2007, Keith et al.
Bard et al. Cloning of a Novel Human Serotonin Receptor (5-HT$_7$) Positively Linked to Adenylate Cyclase. J. Biol. Chem. 1993, 268(31), 23422-23426.
Bonaventure et al. Radioligand Binding Analysis of Knockout Mice Reveals 5-Hydroxytryptamine$_7$ Receptor Distribution and Uncovers 8-Hydroxy-2-(2-di-N-propylamino)tetralin Interaction with α2 Adrenergic Receptors. Neuroscience 2004, 124, 901-911.
Bonnet, U. Moclobemide: Evolution, Pharmacokinetic, and Pharmacodynamic Properties. CNS Drug Rev. 2002, 8(3), 283-308.
Bymaster et al. Fluoxetine, but not other selective serotonin reuptake inhibitors, increases norepinephrine and dopamine extracellular levels in prefrontal cortex. Psychopharmacology (Berlin) 2002, 160(4), 353-361.
Chen et al. P-Glycoprotein Limits the Brain Penetration of Nonsedating but Not Sedating H1-Antagonists. Drug Metab. Dispos. 2003, 31(3), 312-318.
Collier et al. Applications of Nitriles as Reagents for Organic Synthesis with the Loss of the Nitrile Functionality (including Cycloaddition Reactions). Science of Synthesis 2004, 19, 403-425.
Eglen et al. The 5-HT$_7$ Receptor: Orphan Found. Trends Pharmacol. Sci. 1997, 18, 104-107.
Frazer, A. Serotonergic and Noradrenergic Reuptake Inhibitors: Prediction of Clinical Effects from In Vitro Potencies. J. Clin. Psychiatry 2001, 62 Suppl. 12, 16-23.
Garcia Martinez et al. About the Timing of Wagner-Meerwein and Nametkin Rearrangements, 6,2-Hydride Shift, Proton Elimination and Cation Trapping in 2-Norbornyl Carbocations. Tetrahedron 1998, 54(18), 4607-4614.
Glass et al. Midbrain Raphe Modulation of Nonphotic Circadian Clock Resetting and 5-HT Release in the Mammalian Suprachiasmatic Nucleus. J. Neurosci. 2003, 23(20), 7451-7460.
Glennon et al. Higher-End Serotonin Receptors: 5-HT$_5$, 5-HT$_6$, and 5-HT$_7$. J. Med. Chem. 2003, 46(14), 2795-2812.
Guscott et al. The hypothermic effect of 5-CT in mice is mediated through the 5-HT$_7$ receptor. Neuropharmacology 2003, 44(8), 1031-1037.
Guscott et al. Genetic knockout and pharmacological blockade studies of the 5-HT$_7$ receptor suggest therapeutic potential in depression. Neuropharmacology 2005, 48(4), 492-502.
Hagan et al. Characterization of SB-269970-A, a selective 5-HT7 receptor antagonist. Br. J. Pharmacol. 2000, 13093), 539-548.
Hansen et al. Pharmacological Management of Allergic Rhinitis in the Elderly. Drugs Aging 2005, 22(4), 289-296.
Harsing et al. A 5-HT$_7$ Heteroreceptor-Mediated Inhibition of [$^3$H]Serotonin Release in Raphe Nuclei Slices of the Rat: Evidence for a Serotonergic-Glutamatergic Interaction. Neurochem. Res. 2004, 29(8), 1487-1497.
Hedlund et al. 5-HT$_7$ Receptor Inhibition and Inactivation Induce Antidepressantlike Behavior and Sleep Pattern. Biol. Psychiatry 2005, 58(10), 831-837.
Hedlund et al. No hypothermic response to serotonin in 5-HT$_7$ receptor knockout mice. Proc. Natl. Acad. Sci. U.S.A. 2003, 100(3), 1375-1380.
Hedlund et al. Functional, molecular and pharmacological advances in 5-HT$_7$ receptor research. Trends Pharmacol. Sci. 2004, 24(9), 481-486.
Herrera et al. One-pot synthesis of new heterocycles: 2,4-disubstituted 6,7-dihydro-5H-benzo[6,7]cyclohepta[1,2-d]pyrimidines. Tetrahedron Lett. 2003, 44(10), 2149-2151.
Ishiguro et al. Influx and Efflux Transport of H1-Antagonist Epinastine Across the Blood-Brain Barrier. Drug Metab. Dispos. 2004, 32(5), 519-524.

Keating et al. The effect of a series of organic cations upon the plasmalemmal serotonin transporter, SERT. Life Sci. 2004, 76, 109-119.

Lafferty et al. The Preparation and Properties of Certain Pyridylpyrimidines and Bidiazines as Potential Chelating Agents for Iron(II). J. Org. Chem. 1967, 32(5), 1591-1596.

Lovenberg et al. A Novel Adenylyl Cyclase-Activating Serotonin Receptor (5-$HT_7$) Implicated in the Regulation of Mammalian Circadian Rhythms. Neuron 1993, 11(3), 449-458.

Marek et al. Synergistic Action of 5-$HT_{2A}$ Antagonists and Selective Serotonin Reuptake Inhibitors in Neuropsychiatric Disorders. Neuropsychopharmacology 2003, 28, 402-412.

Meneses, A. Effects of the 5-$HT_7$ receptor antagonists SB-269970 and DR 4004 in autoshaping Pavlovian/instrumental learning task. Behav. Brain Res. 2004, 155(2), 275-282.

Murphy et al. Experimental gene interaction studies with SERT mutant mice as models for human polygenic and epistatic traits and disorders. Genes, Brain & Behav. 2003, 2(6), 350-364.

Ni et al. 5-Hydroxytryptamine in the Cardiovascular System: Focus on the Serotonin Transporter (SERT). Clin. Exp. Pharmacol. Physiol. 2006, 33(7), 575-583.

Pouzet, B. SB-258741: A 5-$HT_7$ Receptor Antagonist of Potential Clinical Interest. CNS Drug Rev. 2002, 8(1), 90-100.

Read et al. Evidence for the involvement of central 5-$HT_7$ receptors in the micturition reflex in anaesthetized female rats. Br. J. Pharmacol. 2003, 140, 53-60.

Read et al. Effects of SB-269970, the 5-$HT_7$ Receptor Antagonist, on Micturition. Presentation Abstract, International Union of Basic & Clinical Pharmacology, XIVth World Congress of Pharmacology, San Francisco, CA, Jul. 2002.

Roberts et al. GABAergic modulation of 5-$HT_7$ receptor-mediated effects on 5-HT efflux in the guinea-pig dorsal raphe nucleus. Neuropharmacology 2004, 46(7), 935-941.

Simons et al. The Pharmacology and Use of $H_1$-Receptor-Antagonist Drugs. N. Engl. J. Med. 1994, 330, 1663-1670.

Spinks et al. Serotonin Reuptake Inhibition: An Update on Current Research Strategies. Curr. Med. Chem. 2002, 9, 799-810.

Steru et al. The Automated Tail Suspension Test: A Computerized Device which Differentiates Psychotropic Drugs. Prog. Neuropsychopharmacol. & Biol. Psychiatry 1987, 11(6), 659-671.

Tagawa et al. Neuroimaging of histamine $H_1$-receptor occupancy in human brain by positron emission tomography (PET): A comparative study of ebastine, a second-generation antihistamine, and (+)-chlorpheniramine, a classical antihistamine. Br. J. Clin. Pharmacol. 2001, 52(5), 501-509.

Tashiro et al. Brain histamine $H_1$ receptor occupancy of orally administered antihistamines measured by positron emission tomography with $_{11}$C-doxepin in a placebocontrolled crossover study design in healthy subjects: a comparison of olopatadine and ketotifen. Br. J. Clin. Pharmacol. 2006, 61(1), 16-26.

Tashioro et al. Central Effects of Fexofenadine and Cetirizine: Measurement of Psychomotor Performance, Subjective Sleepiness, and Brain Histamine $H_1$-Receptor Occupancy Using $^{11}$C-Doxepin Positron Emission Tomography. J. Clin. Pharmacol. 2004, 44(8), 890-900.

Thomas et al. SB-656104-A, a novel selective 5-$HT_7$ receptor antagonist, modulates REM sleep in rats. Br. J. Pharmacol. 2003, 139(4), 705-714.

Thomas et al. 5-$HT_7$ Receptors. Curr. Drug Targets CNS Neurol. Disord. 2004, 3(1), 81-90.

To et al. Characterization and distribution of putative 5-$HT_7$ receptors in guinea-pig brain. Br. J. Pharmacol. 1995, 115(1), 107-116.

Tuladhar et al. 5-$HT_7$ receptors mediate the inhibitory effect of 5-HT on peristalsis in the isolated guinea-pig ileum. Br. J. Pharmacol. 2003, 138(7), 1210-1214.

PCT International Search Report for PCT/US 06/40911 dated Sep. 27, 2007.

Martel et al. Recent advances on the importance of the serotonin transporter SERT in the rat intestine. Pharmacol. Res. 2006, 54, 73-76.

Menza, et al. Modafinil Augmentation of Antidepressant Treatment in Depression. J. Clin. Psychiatry 2000, 61, 378-381.

Ohtsuki, S. New Aspects of the Blood-Brain Barrier Transporters; Its Physiological Roles in the Central Nervous System. Biol. Pharm. Bull. 2004, 27(10), 1489-1496.

Olver et al. Third-Generation Antidepressants: Do They Offer Advantages Over the SSRIs? CNS Drugs 2001, 15, 941-954.

Thomas et al. [$^3$H]-SB-269970 radiolabels 5-$HT_7$ receptors in rodent, pig and primate brain tissues. Neuropharmacology 2002, 42(1), 74-81.

Vanhoenacker et al. 5-$HT_7$ receptors: current knowledge and future prospects. Trends Pharmacol. Sci. 2000, 21, 70-77.

Van Wauwe et al. In Vivo Pharmacology of Astemizole, a New Type of $H_1$-Antihistaminic Compound. Arch. Int. Pharmacodyn. 1981, 251, 39-51.

Varnas et al. Distribution of 5-$HT_7$ receptors in the human brain: a preliminary autoradiographic study using [$^3$H]SB-269970. Neurosci. Lett. 2004, 367(3), 313-316.

Welch et al. $H_1$-Antihistamines and the central nervous system. In *Histamine and $H_1$-Antihistamines in Allergic Disease*, $2^{nd}$ ed.; F.E.R. Simons, Ed.; Marcel Dekker, Inc.: New York, 2002; Chapter 11.

Yanai et al. Histamine $H_1$ receptor occupancy in human brains after single oral doses of histamine $H_1$ antagonists measured by positron emission tomography. Br. J. Pharmacol. 1995, 116, 1649-1655.

Yanai et al. Mapping of Histamine $H_1$ Receptors in the Human Brain Using [$^{11}$C]Pyrilamine and Positron Emission Tomography. J. Neurochem. 1992, 59, 128-136.

Yoon et al. Rapid Screening of Blood-Brain Barrier Penetration of Drugs Using the Immobilized Artificial Membrane Phosphatidylcholine Column Chromatography. J. Biomol. Screen 2006, 11(1), 13-20.

* cited by examiner

PYRIMIDINE COMPOUNDS AS SEROTONIN RECEPTOR MODULATORS

RELATED APPLICATIONS

The present application claims the benefit under 35 U.S.C. §119(e) of provisional application Ser. No. 60/705,719, filed on Aug. 4, 2005, which is incorporated herein in its entirety.

FIELD OF THE INVENTION

There is provided by the present invention compounds that are serotonin receptor modulators. More particularly, there is provided by the present invention pyrimidine compounds that are serotonin receptor modulators useful for the treatment of disease states mediated by serotonin receptor activity.

BACKGROUND OF THE INVENTION

Serotonin (5-hydroxytryptamine, 5-HT) is a major neurotransmitter eliciting effects via a multiplicity of receptors. To date, at least fifteen different 5-HT receptors have been identified, largely as the result of cloning cDNA's, and these receptors have been grouped into seven families (5-HT$_1$ through 5-HT$_7$) (Hoyer, D. et al. *Pharmacol. Biochem. Behav.* 2002, 71, 533-554). Fourteen of the fifteen cloned 5-HT receptors are expressed in the brain. 5-HT is implicated in many disease states, particularly conditions of the central nervous system including; depression, anxiety, schizophrenia, eating disorders, obsessive compulsive disorder, learning and memory dysfunction, migraine, chronic pain, sensory perception, motor activity, temperature regulation, nociception, sexual behavior, hormone secretion, and cognition. The identification of multiple 5-HT receptors has provided the opportunity to characterize existing therapeutic agents thought to act via the serotonergic system. Consequently, this has led to the realization that many drugs have non-selective properties (Roth, B. L. et al. *Neuroscientist* 2000, 6(4), 252-262). For example, the antipsychotic drugs, clozapine, chlorpromazine, haloperidol and olanzapine exhibit affinities for multiple serotonin receptors in addition to other families of receptors. Similar behavior has been noted for antidepressants, including imipramine, nortriptaline, fluoxetine and sertraline. Similarly, the anti-migraine agent sumatriptan exhibits high affinity for several serotonin receptors. While the lack of selectivity often contributes to a favorable therapeutic outcome, it can also cause undesirable and dose-limiting side effects (Stahl, S. M. *Essential Psychopharmacology*, 2$^{nd}$ ed., Cambridge University Press, Cambridge, U.K., 2000). Thus, the inhibition of serotonin and norepinephrine uptake together with 5-HT$_2$ receptor blockade is responsible for the therapeutic effects of the tricyclic antidepressants. In contrast, their blockade of histamine H$_1$, muscarinic and alpha-adrenergic receptors can lead to sedation, blurred vision and orthostatic hypertension respectively. Likewise, the atypical antipsychotics, including olanzapine and clozapine, are considered to have positive therapeutic effects attributable to their actions at 5-HT$_2$, D$_2$ and 5-HT$_7$ receptors. Conversely, their side effect liability is due to their affinities for a range of dopaminergic, serotonergic and adrenergic receptors.

More selective ligands therefore have the potential to ameliorate untoward pharmacologies and provide novel therapies. More importantly the ability to obtain compounds with known receptor selectivities affords the prospect to target multiple therapeutic mechanisms and improve clinical responses with a single drug.

4-Phenyltetrahydropyrido[4,3-d]pyrimidines with utility in the treatment of gastrointestinal diseases have been described in U.S. Pat. No. 5,137,890 (Sanfilippo et al.):

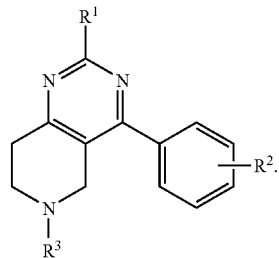

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety.

Described herein is a series of pyrimidine compounds with the ability to modulate the activity of serotonin receptors.

SUMMARY OF THE INVENTION

The invention features a compound of Formulae (I) or (II):

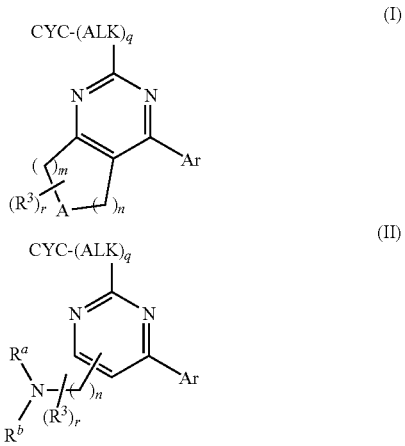

wherein
m is 1, 2, or 3;
n is 1, 2, or 3;
where when m and n are both present, m+n is greater than or equal to 2, and is less than or equal to 4;
R$^a$ and R$^b$ are independently —H, —C$_{1-7}$alkyl, or —C$_{3-7}$cycloalkyl, or R$^a$ and R$^b$ taken together with the nitrogen of attachment form piperidinyl, pyrrolidinyl, morpholinyl, thiomorpholinyl, or piperazinyl, where each R$^a$ and R$^b$ is optionally and independently substituted with —C$_{1-4}$alkyl;
q is 0 or 1;
A is >NR$^1$, >CHNR$^c$R$^d$, >CHOH or —CH$_2$— wherein
 R$^1$ is selected from the group consisting of —H, —C$_{1-7}$alkyl, —C$_{3-7}$cycloalkyl, and benzyl, where each alkyl, cycloalkyl, or benzyl is optionally mono-, di-, or tri-substituted with R$^e$;

$R^e$ is selected from the group consisting of —$C_{1-4}$alkyl, —$C_{2-4}$alkenyl, —$C_{2-4}$alkynyl, —$C_{3-6}$cycloalkyl, halo, —$CF_3$, —OH, —$OC_{1-4}$alkyl, —$OCF_3$, —$N(R^f)R^g$ (wherein $R^f$ and $R^g$ are independently —H or —$C_{1-4}$ alkyl, or $R^f$ and $R^g$ taken together with the nitrogen of attachment form piperidinyl, pyrrolidinyl, morpholinyl, thiomorpholinyl, or piperazinyl), —$C(O)N(R^f)R^g$, —$N(R^h)C(O)R^h$, —$N(R^h)SO_2C_{1-7}$ alkyl (wherein $R^h$ is —H or —$C_{1-4}$alkyl, or two $R^h$ in the same substituent taken together with the amide of attachment form an otherwise aliphatic 4- to 6-membered ring), —$S(O)_{0-2}$—$C_{1-4}$alkyl, —$SO_2N(R^f)R^g$, —$SCF_3$, —$C(O)C_{1-4}$alkyl, —CN, —COOH, and —$COOC_{1-4}$alkyl;

$R^c$ and $R^d$ are independently selected from the group consisting of —H, —$C_{1-7}$alkyl, —$C_{3-7}$alkenyl, —$C_{3-7}$alkynyl, —$C_{3-7}$cycloalkyl, —$C_{1-7}$alkyl$C_{3-7}$cycloalkyl, and —$C_{3-7}$cycloalkyl$C_{1-7}$alkyl, or $R^c$ and $R^d$ taken together with the nitrogen of attachment form piperidinyl, pyrrolidinyl, morpholinyl, thiomorpholinyl, or piperazinyl, where each $R^c$ and $R^d$ is optionally and independently substituted with $R^e$;

$R^3$ is —$C_{1-4}$alkyl, —$C_{1-4}$alkenyl, or benzyl, each optionally substituted with —$C_{1-3}$alkyl, —OH, or halo, or two $R^3$ substituents taken together form $C_{2-5}$alkylene optionally substituted with —$C_{1-3}$alkyl, —OH, or halo;

r is 0 or is an integer less than or equal to m+n+1;

Ar is an aryl or heteroaryl ring selected from the group consisting of:
a) phenyl, optionally mono-, di-, or tri-substituted with $R^i$ or di-substituted on adjacent carbons with —$OC_{1-4}$alkyleneO—, —$(CH_2)_{2-3}NH$—, —$(CH_2)_{1-2}NH(CH_2)$—, —$(CH_2)_{2-3}N(C_{1-4}alkyl)$—, or —$(CH_2)_{1-2}N(C_{1-4}alkyl)(CH_2)$—;
$R^i$ is selected from the group consisting of —$C_{1-7}$alkyl, —$C_{2-7}$alkenyl, —$C_{2-7}$alkynyl, —$C_{3-7}$cycloalkyl, halo, —$CF_3$, —OH, —$OC_{1-7}$alkyl, —$OCF_3$, —$OC_{3-7}$alkenyl, —$OC_{3-7}$alkynyl, —$N(R^j)R^k$ (wherein $R^j$ and $R^k$ are independently —H or —$C_{1-4}$alkyl), —$C(O)N(R^j)R^k$, —$N(R^j)C(O)R^k$, —$N(R^j)SO_2C_{1-6}$ alkyl, —$S(O)_{0-2}$—$C_{1-6}$alkyl, —$SO_2N(R^j)R^k$, —$SCF_3$, —$C(O)C_{1-6}$alkyl, —$NO_2$, —CN, —COOH, and —$COOC_{1-7}$alkyl;
b) a monocyclic aromatic hydrocarbon group having five ring atoms, having a carbon atom which is the point of attachment, having one carbon atom replaced by >O, >S, >NH, or >$N(C_{1-4}alkyl)$, having up to two additional carbon atoms optionally replaced by —N=, optionally mono- or di-substituted with $R^i$;
c) a monocyclic aromatic hydrocarbon group having six ring atoms, having a carbon atom which is the point of attachment, having one or two carbon atoms replaced by —N=, optionally mono- or di-substituted with $R^i$; and
d) phenyl or pyridyl, substituted with a substituent selected from the group consisting of phenyl, phenoxy, pyridyl, thiophenyl, oxazolyl, and tetrazolyl, where the resultant substituted moiety is optionally further mono-, di-, or tri-substituted with $R^i$;

ALK is a branched or unbranched $C_{1-7}$alkylene, $C_{2-7}$alkenylene, $C_{2-7}$alkynylene, $C_{3-7}$cycloalkylene, or $C_{3-7}$cycloalkenylene, optionally mono-, di-, or tri-substituted with $R^m$;
$R^m$ is selected from the group consisting of halo, —$CF_3$, —OH, —$OC_{1-7}$alkyl, —$OC_{3-7}$cycloalkyl, —$OCF_3$, —$N(R^p)R^s$ (wherein $R^p$ and $R^s$ are independently —H or —$C_{1-7}$alkyl), —$C(O)N(R^p)R^s$, —$N(R^t)C(O)R^t$, —$N(R^t)SO_2C_{1-6}$alkyl (wherein $R^t$ is —H or —$C_{1-7}$ alkyl), —$S(O)_{0-2}$—$C_{1-6}$alkyl, —$SO_2N(R^p)R^s$, —$SCF_3$, —CN, —$NO_2$, —$C(O)C_{1-7}$alkyl, —COOH, and —$COOC_{1-7}$alkyl;

CYC is —H or is a ring system selected from the group consisting of:
i) phenyl, optionally mono-, di-, or tri-substituted with $R^u$ or di-substituted on adjacent carbons with —$OC_{1-4}$alkyleneO—, —$(CH_2)_{2-3}NH$—, —$(CH_2)_{1-2}NH(CH_2)$—, —$(CH_2)_{2-3}N(C_{1-4}alkyl)$-, or —$(CH_2)_{1-2}N(C_{1-4}alkyl)(CH_2)$—;
$R^u$ is selected from the group consisting of —$C_{1-7}$alkyl, —$C_{3-7}$cycloalkyl, phenyl, benzyl, halo, —$CF_3$, —OH, —$OC_{1-7}$alkyl, —$OC_{3-7}$cycloalkyl, —Ophenyl, —Obenzyl, —$OCF_3$, —$N(R^v)R^w$ (wherein $R^v$ and $R^w$ are independently —H or —$C_{1-7}$alkyl, or $R^v$ and $R^w$ taken together with the nitrogen of attachment form piperidinyl, pyrrolidinyl, morpholinyl, thiomorpholinyl, or piperazinyl, where each $R^v$ and $R^w$ is optionally and independently substituted with —OH or —$C_{1-7}$alkyl), —$C(O)N(R^v)R^w$, —$N(R^x)C(O)R^x$, —$N(R^x)SO_2C_{1-6}$alkyl (wherein $R^x$ is —H or —$C_{1-7}$ alkyl, or two $R^x$ in the same substituent taken together with the amide of attachment form an otherwise aliphatic 4- to 6-membered ring), —$N$—$(SO_2C_{1-6}$ alkyl$)_2$, —$S(O)_{0-2}$—$C_{1-6}$alkyl, —$SO_2N(R^v)R^w$, —$SCF_3$, —$C(O)C_{1-6}$alkyl, —$NO_2$, —CN, —COOH, and —$COOC_{1-7}$alkyl;
ii) a monocyclic aromatic hydrocarbon group having five ring atoms, having a carbon atom which is the point of attachment, having one carbon atom replaced by >O, >S, >NH, or >$N(C_{1-4}alkyl)$, having up to one additional carbon atoms optionally replaced by —N=, optionally mono- or di-substituted with $R^u$;
iii) a monocyclic aromatic hydrocarbon group having six ring atoms, having a carbon atom which is the point of attachment, having one or two carbon atoms replaced by —N=, optionally mono- or di-substituted with $R^u$; and
iv) a non-aromatic heterocyclic ring having 4 to 8 members, said ring having 0, 1, or 2 non-adjacent heteroatom members selected from the group consisting of O, S, —N=, >NH, and >$N(C_{1-4}alkyl)$, having 0, 1, or 2 double bonds, having 0, 1, or 2 carbon members which is a carbonyl, optionally having one carbon member which forms a bridge, having 0 to 5 substituents $R^u$, and where when q is 0, said ring has a carbon atom which is the point of attachment;

and enantiomers, diastereomers, hydrates, solvates, and pharmaceutically acceptable salts, esters and amides thereof;

with the proviso that in Formula (I):
(a) when ALK is methylene, ethylene, propylene, or isopropylene, CYC is —H, Ar is phenyl or mono-substituted phenyl, m is 2, n is 1, and A is >$NR^1$, then $R^1$ is not —$C_{1-4}$alkyl or benzyl;
(b) when q is 0, CYC is phenyl, Ar is phenyl or 3-chlorophenyl, m is 2, and n is 1, then A is not unsubstituted —$CH_2$—; and
(c) when q is 0, CYC is 2-pyridyl, Ar is 2-pyridyl, m is 2, and n is 1, then A is not unsubstituted —$CH_2$—.

Isomeric forms of the compounds of Formulae (I) and (II) and of their pharmaceutically acceptable salts, esters, and amides, are encompassed within the present invention, and reference herein to one of such isomeric forms is meant to refer to at least one of such isomeric forms. One of ordinary skill in the art will recognize that compounds according to this invention may exist, for example in a single isomeric form whereas other compounds may exist in the form of a regioisomeric mixture.

The present invention provides methods of treating or preventing diseases and conditions mediated by the serotonin receptors, particularly, 5-HT$_7$ and/or 5-HT$_2$ receptor subtypes.

The invention also features pharmaceutical compositions containing such compounds and methods of using such compositions in the treatment or prevention of disease states mediated by the serotonin receptors, particularly, 5-HT$_7$ and/or 5-HT$_2$ receptor subtypes.

Compounds of the present invention are useful in combination with other therapeutic agents as a combination therapy method, including use in combination with selective serotonin reuptake inhibitors (SSRIs), anti-psychotics, norepinephrine reuptake inhibitors (NRIs), sedatives, monoamine oxidase inhibitors (MAOs), or tricyclic antidepressants (TCAs).

Additional features and advantages of the invention will become apparent from the detailed description and examples below, and the appended claims.

DETAILED DESCRIPTION

Particular preferred compounds of the invention comprise a compound of Formula (I) or (II), or an enantiomer, diastereomer, hydrate, solvate thereof, or a pharmaceutically acceptable salt, amide or ester thereof, wherein m, n, $R^a$, $R^b$, q, A, $R^3$, r, Ar, ALK, and CYC have any of the meanings defined hereinabove and equivalents thereof, or at least one of the following assignments and equivalents thereof. Such assignments may be used where appropriate with any of the definitions, claims or embodiments defined herein:

Preferably, m is 1 and n is 1.
Preferably, m is 1 and n is 2.
Preferably, m is 2 and n is 1.
Preferably, m is 2 and n is 2.
Preferably, m is 1 and n is 3.
Preferably, m is 3 and n is 1.
Preferably, in Formula (II), n is 1.
Preferably, in Formula (II), n is 2.
Preferably, q is 1.
Preferably, —N($R^a$)$R^b$ is amino, methylamino, ethylamino, isopropylamino, dimethylamino, diethylamino, diisopropylamino, cyclopropylamino, cyclopentylamino, piperidinyl, pyrrolidinyl, morpholinyl, thiomorpholinyl, or piperazinyl.

More preferably, —N($R^a$)$R^b$ is amino, methylamino, dimethylamino, or N-methylpiperazinyl.

Preferably, A is >N$R^1$.

Preferably, $R^1$ is selected from the group consisting of hydrogen, methyl, ethyl, isopropyl, butyl, hexyl, cyclopropyl, cyclobutyl, cyclopentyl, and benzyl, each optionally mono-, di-, or tri-substituted with $R^e$.

More preferably, $R^1$, optionally $R^e$ substituted, is selected from the group consisting of hydrogen, methyl, ethyl, isopropyl, and benzyl.

Even more preferably, $R^1$ is hydrogen or methyl.

Preferably, $R^3$, optionally substituted, is selected from the group consisting of methyl, ethyl, propyl, isopropyl, butyl, methylene, allyl, and benzyl. Alternatively, two $R^3$ substituents taken together form ethylene.

More preferably, $R^3$ is methyl.

Preferably, r is 0, 1, or 2.

Preferably Ar, optionally substituted, is selected from the group consisting of:

a) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4,5,6 or 7-yl, 1,2,3,4-tetrahydro-isoquinolin-4,5,6 or 7-yl, b) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, c) pyridinyl, pyridinyl-N-oxide, pyrazinyl, pyrimidinyl, pyridazinyl, and d) biphenyl, and 4-tetrazolylphenyl.

More preferably, Ar, optionally substituted, is selected from the group consisting of phenyl, pyridyl, thiophen-2-yl, and thiophen-3-yl.

Specific Ar may be selected from the group consisting of phenyl, 2-methoxyphenyl, 3-methoxyphenyl, 4-methoxyphenyl, 2-methylphenyl, 3-methylphenyl, 4-methylphenyl, 4-ethylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-trifluoromethylphenyl, 3-trifluoromethylphenyl, 4-trifluoromethylphenyl, 3-trifluoromethoxyphenyl, 4-trifluoromethoxyphenyl, 3-cyanophenyl, 4-cyanophenyl, 3-acetylphenyl, 4-acetylphenyl, 3,4-difluorophenyl, 3,4-dichlorophenyl, 2,3-difluorophenyl, 2,3-dichlorophenyl, 2,4-difluorophenyl, 2,4-dichlorophenyl, 3-nitrophenyl, 4-nitrophenyl, 3-chloro-4-fluorophenyl, 3-fluoro-4-chlorophenyl, benzo[1,3]dioxol-4 or 5-yl, 3-hydroxyphenyl, 4-hydroxyphenyl, 4-hydroxy-2-methylphenyl, 4-hydroxy-3-fluorophenyl, 3,4-dihydroxyphenyl, 4-dimethylaminophenyl, 4-carbamoylphenyl, 4-fluoro-3-methylphenyl, 2-phenoxyphenyl, furan-2-yl, furan-3-yl, 5-methyl-furan-2-yl, thiophen-2-yl, thiophen-3-yl, 5-chlorothiophen-2-yl, 5-methylthiophen-2-yl, 5-chlorothiophen-3-yl, 5-methylthiophen-3-yl, oxazol-2-yl, 4,5-dimethyl-oxazol-2-yl, thiazol-2-yl, 3H-[1,2,3]triazol-4-yl, 2H-pyrazol-3-yl, 1H-pyrazol-4-yl, 4-pyridyl, 5-fluoro-pyridin-2-yl, 4'-chlorobiphenyl, and 4-tetrazolylphenyl.

Preferably, ALK, optionally substituted, is selected from the group consisting of methylene, ethylene, propylene, butylene, sec-butylene, tert-butylene, pentylene, 1-ethylpropylene, 2-ethylpropylene, 2-ethylbutylene, isopropylene, but-3-enylene, isobutylene, 3-methylbutylene, allylene, prop-2-ynylene, cyclopropylene, cyclobutylene, cyclopentylene, cyclohexylene, and cycloheptylene.

Specific ALK may be selected from the group consisting of methylene, hydroxymethylene, fluoromethylene, difluoromethylene, trifluoromethylmethylene, 2,2,2-trifluoro-1-trifluoromethyl-ethylene, methoxycarbonylmethyl, methylcarbamoylmethyl, ethylene, 2-dimethylaminoethylene, 2-cyanoethylene, 2-methoxyethylene, 1-carboxy-ethylene, propylene, 3-methoxycarbonyl propylene, 3-carboxy propylene, isopropylene, 1-fluoro-1-methyl-ethylene, 1-hydroxy-1-methyl-ethylene, 1-carboxy-1-methyl-ethylene, 1-ethylpropylene, 2-ethylpropylene, butylene, tert-butylene, sec-butylene, isobutylene, 4-hydroxybutylene, 4-methoxycarbonyl butylene, 4-carboxy butylene, 2-ethylbutylene, isobutylene, 3-methylbutylene, prop-2-ynylene, but-3-enylene, pentylene, 5-hydroxypentylene, cyclopropylene, cyclobutylene, cyclopentylene, cyclopentenylene, 3,3-difluoro-cyclopentylene, 3-hydroxy-cyclohexylene, 4-fluoro-cyclohexylene, 4,4-difluoro-cyclohexylene, and 1-methyl-cyclopropylene.

Preferably CYC, optionally substituted, is hydrogen or is a ring system selected from the group consisting of:

i) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4,5,6 or 7-yl, 1,2,3,4-tetrahydro-isoquinolin-4,5,6 or 7-yl, ii) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, iii) pyridinyl, pyridinyl-N-oxide, pyrazinyl, pyrimidinyl, pyridazinyl, and iv) pyrrolinyl, pyrrolidinyl, pyrazolinyl, piperidinyl, homopiperidinyl, azepanyl, tetrahydrofuranyl, tetrahydropyranyl, piperazinyl, morpholinyl, thiomorpholinyl, and piperidinonyl.

More preferably, CYC, optionally substituted, is selected from the group consisting of hydrogen, phenyl, thiophen-2-yl, thiophen-3-yl, furan-2-yl, furan-3-yl, pyridinyl, piperidin-1,2,3 or 4-yl, 2-pyrrolin-2,3,4, or 5-yl, 3-pyrrolin-2 or 3-yl, 2-pyrazolin-3,4 or 5-yl, tetrahydrofuran-3-yl, tetrahydropyran-4-yl, morpholin-2,3, or 4-yl, thiomorpholin-2,3, or 4-yl, piperazin-1,2,3, or 4-yl, pyrrolidin-1,2, or 3-yl, and homopiperidinyl.

Most preferably, CYC, optionally substituted, is selected from the group consisting of hydrogen, phenyl, pyridyl, thiophen-2-yl, thiophen-3-yl, tetrahydropyranyl, furan-2-yl, furan-3-yl, tetrahydrofuran-3-yl, and piperidinyl.

Specific CYC may be selected from the group consisting of hydrogen, phenyl, 2-methoxyphenyl, 3-methoxyphenyl, 4-methoxyphenyl, 2-methylphenyl, 3-methylphenyl, 4-methylphenyl, 4-ethylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-trifluoromethylphenyl, 3-trifluoromethylphenyl, 4-trifluoromethylphenyl, 3-trifluoromethoxyphenyl, 4-trifluoromethoxyphenyl, 2-cyanophenyl, 3-cyanophenyl, 4-cyanophenyl, 3-acetylphenyl, 4-acetylphenyl, 3,4-difluorophenyl, 3,4-dichlorophenyl, 2,3-difluorophenyl, 2,3-dichlorophenyl, 2,4-difluorophenyl, 2,4-dichlorophenyl, 2,6-difluorophenyl, 2,6-dichlorophenyl, 2,6-dimethylphenyl, 2,4,6-trifluorophenyl, 2,4,6-trichlorophenyl, 3,4,5-trimethoxyphenyl, 4-fluoro-3-methylphenyl, 3-nitrophenyl, 4-nitrophenyl, 4-methyl-3-fluorophenyl, 3,4-dimethylphenyl, 4-methoxy-3-fluorophenyl, 4-methoxy-2-methylphenyl, 3-aminophenyl, 4-aminophenyl, 4-carbomethoxyphenyl, 3-methanesulfonylamino-phenyl, 4-methanesulfonylamino-phenyl, 3-dimethanesulfonylamino-phenyl, 4-dimethanesulfonylamino-phenyl, thiophen-2-yl, thiophen-3-yl, 5-chlorothiophen-2-yl, benzo[1,3]dioxol-4 or 5-yl, tetrahydrofuran-3-yl, tetrahydropyran-2,3 or 4-yl, furan-2-yl, furan-3-yl, 5-carboxyethyl-furan-2-yl, piperidinyl, 3,4-bis-benzyloxyphenyl, 2-hydroxyphenyl, 3-hydroxyphenyl, 4-hydroxyphenyl, 4-hydroxy-2-methylphenyl, 4-hydroxy-3-fluorophenyl, 3,4-dihydroxyphenyl, 1-piperidinyl, 4-piperidinyl, and 1-methyl-4-piperidinyl.

In one embodiment of Formula (I), CYC-(ALK)$_q$- is —C$_{3-8}$cycloalkyl.

In another embodiment of Formula (I), CYC-(ALK)$_q$- is not methyl, ethyl, propyl, or isopropyl where A is >NR$^1$. In another embodiment of Formula (I), CYC-(ALK)$_q$- is not methyl, ethyl, propyl, or isopropyl. In another embodiment of Formula (I), m is not 2. In another embodiment of Formula (I), A is not unsubstituted —CH$_2$— where q is 0.

Compounds of Formulae (I) and (II) comprise compounds that satisfy any one of the combinations of definitions given herein and equivalents thereof.

It is understood that the symbol ">" when used herein immediately prior to an atom means that the atom immediately following this symbol is divalent.

It is understood that some compounds referred to herein are chiral and/or have geometric isomeric centers, for example E- and Z-isomers. The present invention encompasses all such optical isomers, including diastereomers and racemic mixtures, atropisomers, and geometric isomers, and mixtures thereof, that possess the activity that characterizes the compounds of this invention. In addition, certain compounds referred to herein can exist in solvated as well as unsolvated forms. It is understood that this invention encompasses all such solvated and unsolvated forms that possess the activity that characterizes the compounds of this invention.

Compounds according to the present invention that have been modified to be detectable by some analytic technique are also within the scope of this invention. The compounds of the present invention may be labeled with radioactive elements such as $^{125}$I, $^{18}$F, $^{11}$C, $^{64}$Cu, $^{3}$H, $^{14}$C, and the like for use in imaging or for radioactive treatment of patients. An example of such compounds is an isotopically labeled compound, such as an $^{18}$F isotopically labeled compound that may be used as a probe in detection and/or imaging techniques, such as positron emission tomography (PET) and single-photon emission computed tomography (SPECT). Preferably, compounds of the present invention labeled with $^{18}$F or $^{11}$C may be used as a positron emission tomography (PET) molecular probe for studying serotonin-mediated disorders. Alternatively, compounds of the present invention labeled with $^{14}$C may be used in metabolic studies. Another example of such compounds is an isotopically labeled compound, such as a deuterium and/or tritium labeled compound, that may be used in reaction kinetic studies. The compounds described herein may be reacted with an appropriate functionalized radioactive reagent using conventional chemistry to provide radiolabeled compounds.

Preferred compounds, which are pyrimidines, are selected from the group consisting of:

| Ex. | Chemical Name |
|---|---|
| 1 | 2-tert-Butyl-4-(4-fluoro-phenyl)-5,6,7,8-tetrahydro-pyrido[4,3-d]pyrimidine; |
| 2 | 2-Benzyl-4-(4-fluoro-phenyl)-5,6,7,8-tetrahydro-pyrido[4,3-d]pyrimidine; |
| 3 | 2-sec-Butyl-4-(4-fluoro-phenyl)-5,6,7,8-tetrahydro-pyrido[4,3-d]pyrimidine hydrochloride; |
| 4 | 2-sec-Butyl-4-p-totyl-5,6,7,8-tetrahydro-pyrido[4,3-d]pyrimidine hydrochloride; |
| 5 | 2-Cyclobutyl-4-(4-fluoro-phenyl)-5,6,7,8-tetrahydro-pyrido[4,3-d]pyrimidine hydrochloride; |
| 6 | 2-Cyclobutyl-4-p-tolyl-5,6,7,8-tetrahydro-pyrido[4,3-d]pyrimidine; |
| 7 | 2-Cyclopropyl-4-(4-fluoro-phenyl)-5,6,7,8-tetrahydro-pyrido[4,3-d]pyrimidine; |
| 8 | 2-Benzyl-4-p-tolyl-5,6,7,8-tetrahydro-pyrido[4,3-d]pyrimidine; |
| 9 | 2-Benzyl-4-(4-trifluoromethyl-phenyl)-5,6,7,8-tetrahydro-pyrido[4,3-d]pyrimidine; |
| 10 | 2-Benzyl-4-(3,4-difluoro-phenyl)-5,6,7,8-tetrahydro-pyrido[4,3-d]pyrimidine; |
| 11 | 2-Benzyl-4-phenyl-5,6,7,8-tetrahydro-pyrido[4,3-d]pyrimidine; |
| 12 | 2-Benzyl-4-(3-fluoro-phenyl)-5,6,7,8-tetrahydro-pyrido[4,3-d]pyrimidine; |
| 13 | 2-(4-Fluoro-benzyl)-4-(4-fluoro-phenyl)-5,6,7,8-tetrahydro-pyrido[4,3-d]pyrimidine; |
| 14 | 2-(4-Fluoro-benzyl)-4-(4-fluoro-phenyl)-6-methyl-5,6,7,8-tetrahydro-pyrido[4,3-d]pyrimidine; |

-continued

| Ex. | Chemical Name |
|---|---|
| 15 | 4-[2-(4-Fluoro-benzyl)-6-methyl-5,6,7,8-tetrahydro-pyrido[4,3-d]pyrimidin-4-yl]-benzonitrile; |
| 16 | 4-[2-(4-Fluoro-benzyl)-5,6,7,8-tetrahydro-pyrido[4,3-d]pyrimidin-4-yl]-benzonitrile; |
| 17 | 2-Cyclopentyl-4-(4-fluoro-phenyl)-5,6,7,8-tetrahydro-pyrido[4,3-d]pyrimidine; |
| 18 | 2-Cyclopentyl-4-p-tolyl-5,6,7,8-tetrahydro-pyrido[4,3-d]pyrimidine; |
| 19 | 2-Cyclopentyl-4-(4-methoxy-phenyl)-5,6,7,8-tetrahydro-pyrido[4,3-d]pyrimidine; |
| 20 | 4-(2-Cyclopentyl-5,6,7,8-tetrahydro-pyrido[4,3-d]pyrimidin-4-yl)-benzonitrile; |
| 21 | 4-(4-Fluoro-phenyl)-2-isopropyl-5,6,7,8-tetrahydro-pyrido[4,3-d]pyrimidine hydrochloride; |
| 22 | 4-(4-Fluoro-phenyl)-2-isopropyl-6-methyl-5,6,7,8-tetrahydro-pyrido[4,3-d]pyrimidine; |
| 23 | 4-(3,4-Dichloro-phenyl)-2-isopropyl-5,6,7,8-tetrahydro-pyrido[4,3-d]pyrimidine hydrochloride; |
| 24 | 4-(3,4-Difluoro-phenyl)-2-isopropyl-5,6,7,8-tetrahydro-pyrido[4,3-d]pyrimidine hydrochloride; |
| 25 | 4-(3-Fluoro-phenyl)-2-isopropyl-5,6,7,8-tetrahydro-pyrido[4,3-d]pyrimidine; |
| 26 | 4-(2-Fluoro-phenyl)-2-isopropyl-5,6,7,8-tetrahydro-pyrido[4,3-d]pyrimidine; |
| 27 | 4-(2,4-Difluoro-phenyl)-2-isopropyl-5,6,7,8-tetrahydro-pyrido[4,3-d]pyrimidine; |
| 28 | 2-Isopropyl-4-p-tolyl-5,6,7,8-tetrahydro-pyrido[4,3-d]pyrimidine; |
| 29 | 4-(4-Chloro-phenyl)-2-isopropyl-5,6,7,8-tetrahydro-pyrido[4,3-d]pyrimidine; |
| 30 | 2-Isopropyl-4-(4-methoxy-phenyl)-5,6,7,8-tetrahydro-pyrido[4,3-d]pyrimidine; |
| 31 | 2-Isopropyl-4-phenyl-5,6,7,8-tetrahydro-pyrido[4,3-d]pyrimidine; |
| 32 | 2-Isopropyl-4-(4-trifluoromethyl-phenyl)-5,6,7,8-tetrahydro-pyrido[4,3-d]pyrimidine; |
| 33 | 2-Isopropyl-4-(2-phenoxy-phenyl)-5,6,7,8-tetrahydro-pyrido[4,3-d]pyrimidine; |
| 34 | 2-Isobutyl-4-thiophen-3-yl-5,6,7,8-tetrahydro-pyrido[4,3-d]pyrimidine; |
| 35 | 2-Isobutyl-4-thiophen-2-yl-5,6,7,8-tetrahydro-pyrido[4,3-d]pyrimidine; |
| 36 | 2-Isobutyl-4-pyridin-4-yl-5,6,7,8-tetrahydro-pyrido[4,3-d]pyrimidine; |
| 37 | 4-(4-Fluoro-phenyl)-2-isobutyl-5,6,7,8-tetrahydro-pyrido[4,3-d]pyrimidine; |
| 38 | 2-Isobutyl-4-p-tolyl-5,6,7,8-tetrahydro-pyrido[4,3-d]pyrimidine; |
| 39 | 4-(4-Fluoro-3-methyl-phenyl)-2-isobutyl-5,6,7,8-tetrahydro-pyrido[4,3-d]pyrimidine; |
| 40 | 4-(2-Isobutyl-5,6,7,8-tetrahydro-pyrido[4,3-d]pyrimidin-4-yl)-benzonitrile; |
| 41 | 2-Isobutyl-4-(4-methoxy-phenyl)-5,6,7,8-tetrahydro-pyrido[4,3-d]pyrimidine; |
| 42 | 2-sec-Butyl-4-(2-fluoro-phenyl)-5,6,7,8-tetrahydro-pyrido[4,3-d]pyrimidine hydrochloride; |
| 43 | 2-sec-Butyl-4-(3-fluoro-phenyl)-5,6,7,8-tetrahydro-pyrido[4,3-d]pyrimidine; |
| 44 | 2-sec-Butyl-4-(4-methoxy-phenyl)-5,6,7,8-tetrahydro-pyrido[4,3-d]pyrimidine; |
| 45 | 2-sec-Butyl-4-(4-trifluoromethoxy-phenyl)-5,6,7,8-tetrahydro-pyrido[4,3-d]pyrimidine; |
| 46 | 2-Cyclopentyl-4-(4-fluoro-phenyl)-6,7,8,9-tetrahydro-5H-pyrimido[4,5-d]azepine; |
| 47 | 2-Cyclopentyl-4-p-tolyl-6,7,8,9-tetrahydro-5H-pyrimido[4,5-d]azepine; |
| 48 | 2-Cyclopentyl-4-(4-methoxy-phenyl)-6,7,8,9-tetrahydro-5H-pyrimido[4,5-d]azepine; |
| 49 | 4-(2-Cyclopentyl-6,7,8,9-tetrahydro-5H-pyrimido[4,5-d]azepin-4-yl)-benzonitrile; |
| 50 | 4-(4-Fluoro-phenyl)-2-isopropyl-6,7,8,9-tetrahydro-5H-pyrimido[4,5-d]azepine hydrochloride; |
| 51 | 4-(4-Chloro-phenyl)-2-methyl-6,7,8,9-tetrahydro-5H-pyrimido[4,5-d]azepine; |
| 52 | 2-Methyl-4-phenyl-6,7,8,9-tetrahydro-5H-pyrimido[4,5-d]azepine; |
| 53 | 4-(3-Chloro-phenyl)-2-methyl-6,7,8,9-tetrahydro-5H-pyrimido[4,5-d]azepine; |
| 54 | 2-Benzyl-4-(4-fluoro-phenyl)-6,7,8,9-tetrahydro-5H-pyrimido[4,5-d]azepine; |
| 55 | 2-Benzyl-4-p-tolyl-6,7,8,9-tetrahydro-5H-pyrimido[4,5-d]azepine; |
| 56 | 2-Benzyl-4-(4-trifluoromethyl-phenyl)-6,7,8,9-tetrahydro-5H-pyrimido[4,5-d]azepine; |
| 57 | 2-(4-Fluoro-benzyl)-4-(4-fluoro-phenyl)-6,7,8,9-tetrahydro-5H-pyrimido[4,5-d]azepine; |
| 58 | 2-Cyclopentyl-4-(4-fluoro-phenyl)-7-methyl-6,7,8,9-tetrahydro-5H-pyrimido[4,5-d]azepine; |
| 59 | 2-Cyclopentyl-7-methyl-4-p-tolyl-6,7,8,9-tetrahydro-5H-pyrimido[4,5-d]azepine; |
| 60 | 2-Cyclopentyl-4-(4-methoxy-phenyl)-7-methyl-6,7,8,9-tetrahydro-5H-pyrimido[4,5-d]azepine; |
| 61 | 2-Benzyl-7-methyl-4-p-tolyl-6,7,8,9-tetrahydro-5H-pyrimido[4,5-d]azepine; |
| 62 | 2-(4-Fluoro-benzyl)-4-(4-fluoro-phenyl)-7-methyl-6,7,8,9-tetrahydro-5H-pyrimido[4,5-d]azepine; |
| 63 | 2-(4-Fluoro-benzyl)-4-(4-fluoro-phenyl)-7-methyl-9-methylene-6,7,8,9-tetrahydro-5H-pyrimido[4,5-d]azepine; |
| 64 | 2-Benzyl-4-(4-fluoro-phenyl)-6,7,8,9-tetrahydro-5H-pyrimido[4,5-c]azepine hydrochloride; |
| 65 | 4-(4-Fluoro-phenyl)-2-isopropyl-6,7,8,9-tetrahydro-5H-pyrimido[4,5-c]azepine hydrochloride; |
| 66 | 2-Isopropyl-4-p-tolyl-6,7,8,9-tetrahydro-5H-pyrimido[4,5-c]azepine hydrochloride; |
| 67 | 2-Isopropyl-4-(4-methoxy-phenyl)-6,7,8,9-tetrahydro-5H-pyrimido[4,5-c]azepine; |
| 68 | 2-Isopropyl-4-phenyl-6,7,8,9-tetrahydro-5H-pyrimido[4,5-c]azepine; |
| 69 | 2-Benzyl-4-(4-fluoro-phenyl)-6,7,8,9-tetrahydro-5H-1,3,6-triaza-benzocycloheptene hydrochloride; |
| 70 | 2,7-Dibenzyl-4-(4-fluoro-phenyl)-5,6,7,8-tetrahydro-pyrido[3,4-d]pyrimidine hydrochloride; |
| 71 | 2,7-Dibenzyl-4-p-tolyl-5,6,7,8-tetrahydro-pyrido[3,4-d]pyrimidine; |
| 72 | 2,7-Dibenzyl-4-phenyl-5,6,7,8-tetrahydro-pyrido[3,4-d]pyrimidine; |
| 73 | 2,7-Dibenzyl-4-(4-methoxy-phenyl)-5,6,7,8-tetrahydro-pyrido[3,4-d]pyrimidine; |
| 74 | 7-Benzyl-4-(4-fluoro-phenyl)-2-isopropyl-5,6,7,8-tetrahydro-pyrido[3,4-d]pyrimidine; |
| 75 | 7-Benzyl-2-isopropyl-4-phenyl-5,6,7,8-tetrahydro-pyrido[3,4-d]pyrimidine; |
| 76 | 2-Benzyl-4-(4-fluoro-phenyl)-5,6,7,8-tetrahydro-pyrido[3,4-d]pyrimidine hydrochloride; |
| 77 | 2-Benzyl-4-p-tolyl-5,6,7,8-tetrahydro-pyrido[3,4-d]pyrimidine hydrochloride; |
| 78 | 2-Benzyl-4-phenyl-5,6,7,8-tetrahydro-pyrido[3,4-d]pyrimidine; |
| 79 | 2-Benzyl-4-(4-methoxy-phenyl)-5,6,7,8-tetrahydro-pyrido[3,4-d]pyrimidine; |

-continued

| Ex. | Chemical Name |
|---|---|
| 80 | 4-(4-Fluoro-phenyl)-2-isopropyl-5,6,7,8-tetrahydro-pyrido[3,4-d]pyrimidine hydrochloride; |
| 81 | 2-Isopropyl-4-phenyl-5,6,7,8-tetrahydro-pyrido[3,4-d]pyrimidine; |
| 82 | 2-Benzyl-4-(4-fluoro-phenyl)-7-methyl-5,6,7,8-tetrahydro-pyrido[3,4-d]pyrimidine hydrochloride; |
| 83 | 2-Benzyl-4-(4-fluoro-phenyl)-7-isopropyl-5,6,7,8-tetrahydro-pyrido[3,4-d]pyrimidine; |
| 84 | 4-(4-Fluoro-phenyl)-2-isopropyl-7-methyl-5,6,7,8-tetrahydro-pyrido[3,4-d]pyrimidine hydrochloride; |
| 85 | 2-Isopropyl-7-methyl-4-phenyl-5,6,7,8-tetrahydro-pyrido[3,4-d]pyrimidine; |
| 86 | 7-Benzyl-2-isopropyl-4-(5-methyl-thiophen-3-yl)-5,6,7,8-tetrahydro-pyrido[3,4-d]pyrimidine hydrochloride; |
| 87 | 7-Benzyl-2-isopropyl-4-thiophen-3-yl-5,6,7,8-tetrahydro-pyrido[3,4-d]pyrimidine hydrochloride; |
| 88 | 2-Isopropyl-4-(5-methyl-thiophen-3-yl)-5,6,7,8-tetrahydro-pyrido[3,4-d]pyrimidine hydrochloride; |
| 89 | 2-Isopropyl-4-thiophen-3-yl-5,6,7,8-tetrahydro-pyrido[3,4-d]pyrimidine hydrochloride; |
| 90 | 2-Isopropyl-7-methyl-4-(5-methyl-thiophen-3-yl)-5,6,7,8-tetrahydro-pyrido[3,4-d]pyrimidine hydrochloride; |
| 91 | 2-Isopropyl-7-methyl-4-thiophen-3-yl-5,6,7,8-tetrahydro-pyrido[3,4-d]pyrimidine hydrochloride; |
| 92 | 6-Benzyl-4-(4-fluoro-phenyl)-2-isopropyl-8-methyl-5,6,7,8-tetrahydro-pyrido[4,3-d]pyrimidine; |
| 93 | 6-Benzyl-4-(3-chloro-4-fluoro-phenyl)-2-isopropyl-8-methyl-5,6,7,8-tetrahydro-pyrido[4,3-d]pyrimidine; |
| 94 | 6-Benzyl-2-isopropyl-8-methyl-4-p-tolyl-5,6,7,8-tetrahydro-pyrido[4,3-d]pyrimidine; |
| 95 | 6-Benzyl-2-isopropyl-8-methyl-4-phenyl-5,6,7,8-tetrahydro-pyrido[4,3-d]pyrimidine; |
| 96 | 6-Benzyl-2-isopropyl-8-methyl-4-(4-trifluoromethyl-phenyl)-5,6,7,8-tetrahydro-pyrido[4,3-d]pyrimidine; |
| 97 | 6-Benzyl-4-(4-chloro-phenyl)-2-isopropyl-8-methyl-5,6,7,8-tetrahydro-pyrido[4,3-d]pyrimidine; |
| 98 | 6-Benzyl-2-isopropyl-8-methyl-4-thiophen-3-yl-5,6,7,8-tetrahydro-pyrido[4,3-d]pyrimidine; |
| 99 | 6-Benzyl-4-(4'-chloro-biphenyl-4-yl)-2-isopropyl-8-methyl-5,6,7,8-tetrahydro-pyrido[4,3-d]pyrimidine; |
| 100 | 4-(4-Fluoro-phenyl)-2-isopropyl-8-methyl-5,6,7,8-tetrahydro-pyrido[4,3-d]pyrimidine hydrochloride; |
| 101 | 4-(3-Chloro-4-fluoro-phenyl)-2-isopropyl-8-methyl-5,6,7,8-tetrahydro-pyrido[4,3-d]pyrimidine hydrochloride; |
| 102 | 2-Isopropyl-8-methyl-4-p-tolyl-5,6,7,8-tetrahydro-pyrido[4,3-d]pyrimidine hydrochloride; |
| 103 | 2-Isopropyl-8-methyl-4-phenyl-5,6,7,8-tetrahydro-pyrido[4,3-d]pyrimidine; |
| 104 | 2-Isopropyl-8-methyl-4-(4-trifluoromethyl-phenyl)-5,6,7,8-tetrahydro-pyrido[4,3-d]pyrimidine; |
| 105 | 2-Isopropyl-8-methyl-4-thiophen-3-yl-5,6,7,8-tetrahydro-pyrido[4,3-d]pyrimidine; |
| 106 | 4-(4-Fluoro-phenyl)-2-isopropyl-6,7-dihydro-5H-pyrrolo[3,4-d]pyrimidine hydrochloride; |
| 107 | 4-(4-Fluoro-phenyl)-2-isopropyl-7-pyrrolidin-1-yl-5,6,7,8-tetrahydro-quinazoline; |
| 108 | [4-(4-Fluoro-phenyl)-2-isopropyl-5,6,7,8-tetrahydro-quinazolin-7-yl]-methyl-amine hydrochloride; |
| 109 | [4-(4-Fluoro-phenyl)-2-isopropyl-5,6,7,8-tetrahydro-quinazolin-6-yl]-methyl-amine hydrochloride; |
| 110 | 4-(4-Fluoro-phenyl)-2-isopropyl-5,6,7,8-tetrahydro-quinazolin-7-ol; |
| 111 | 4-(4-Fluoro-phenyl)-2-isopropyl-5,6,7,8-tetrahydro-quinazoline; |
| 112 | (2-Benzyl-6-p-tolyl-pyrimidin-4-ylmethyl)-dimethyl-amine; |
| 113 | 2-Benzyl-4-(4-methyl-piperazin-1-ylmethyl)-6-p-tolyl-pyrimidine; |
| 114 | [6-(4-Fluoro-phenyl)-2-isopropyl-pyrimidin-4-ylmethyl]-methyl-amine; |
| 115 | 2-(2-Benzyl-6-p-tolyl-pyrimidin-4-yl)-ethylamine; |
| 116 | [2-(4-Fluoro-benzyl)-4-p-tolyl-pyrimidin-5-ylmethyl]-dimethyl-amine; |
| 117 | 4-(4-Fluoro-phenyl)-2-phenyl-5,6,7,8-tetrahydro-pyrido[4,3-d]pyrimidine; |
| 118 | 2-(3,3-Difluoro-cyclopentyl)-4-(4-fluoro-phenyl)-5,6,7,8-tetrahydro-pyrido[4,3-d]pyrimidine; |
| 119 | 4-(4-Fluoro-phenyl)-2-(tetrahydro-furan-3-yl)-5,6,7,8-tetrahydro-pyrido[4,3-d]pyrimidine; |
| 120 | 4-(4-Fluoro-phenyl)-2-(2-piperidin-1-yl-ethyl)-5,6,7,8-tetrahydro-pyrido[4,3-d]pyrimidine; |
| 121 | 2-(1-Fluoro-1-methyl-ethyl)-4-(4-fluoro-phenyl)-5,6,7,8-tetrahydro-pyrido[4,3-d]pyrimidine; |
| 122 | 3-(4-Fluoro-phenyl)-5-isopropyl-4,6,12-triaza-tricyclo[7.2.1.0$^{2,7}$]dodeca-2,4,6-triene; |
| 123 | 7-(4-Fluoro-phenyl)-5-isopropyl-4,6,13-triaza-tricyclo[8.2.1.0$^{3,8}$]trideca-3,5,7-triene; |
| 124 | 4-(4-Fluoro-phenyl)-2-(tetrahydro-pyran-4-yl)-5,6,7,8-tetrahydro-pyrido[4,3-d]pyrimidine; |
| 125 | 4-(4-Fluoro-phenyl)-2-(tetrahydro-pyran-3-yl)-5,6,7,8-tetrahydro-pyrido[4,3-d]pyrimidine; |
| 126 | 4-(4-Fluoro-phenyl)-2-(2-methoxy-ethyl)-5,6,7,8-tetrahydro-pyrido[4,3-d]pyrimidine; |
| 127 | 2-[4-(4-Fluoro-phenyl)-5,6,7,8-tetrahydro-pyrido[4,3-d]pyrimidin-2-yl]-propan-2-ol; |
| 128 | 4-(4-Fluoro-phenyl)-2-(1-methyl-1-phenyl-ethyl)-5,6,7,8-tetrahydro-pyrido[4,3-d]pyrimidine; |
| 129 | 2-Cyclopent-3-enyl-4-(4-fluoro-phenyl)-5,6,7,8-tetrahydro-pyrido[4,3-d]pyrimidine; |
| 130 | 3-[4-(4-Fluoro-phenyl)-5,6,7,8-tetrahydro-pyrido[4,3-d]pyrimidin-2-yl]-cyclohexanol; |

-continued

| Ex. | Chemical Name |
|---|---|
| 131 | 4-(4-Fluoro-phenyl)-2-piperidin-4-yl-5,6,7,8-tetrahydro-pyrido[4,3-d]pyrimidine; |
| 132 | 4-(4-Fluoro-phenyl)-2-(1-methyl-piperidin-4-yl)-5,6,7,8-tetrahydro-pyrido[4,3-d]pyrimidine; |
| 133 | [4-(4-Fluoro-phenyl)-5,6,7,8-tetrahydro-pyrido[4,3-d]pyrimidin-2-yl]-phenyl-methanol; |
| 134 | 4-(4-Fluoro-phenyl)-2-(fluoro-phenyl-methyl)-5,6,7,8-tetrahydro-pyrido[4,3-d]pyrimidine; |
| 135 | 2-(Difluoro-phenyl-methyl)-4-(4-fluoro-phenyl)-5,6,7,8-tetrahydro-pyrido[4,3-d]pyrimidine; |
| 136 | 4-(4-Fluoro-phenyl)-2-phenyl-5,6,7,8-tetrahydro-pyrido[4,3-d]pyrimidine; |
| 137 | 4-(4-Fluoro-phenyl)-2-(3-fluoro-phenyl)-5,6,7,8-tetrahydro-pyrido[4,3-d]pyrimidine; |
| 138 | 4-(4-Fluoro-phenyl)-2-(4-methoxy-phenyl)-5,6,7,8-tetrahydro-pyrido[4,3-d]pyrimidine; |
| 139 | 4-(4-Fluoro-phenyl)-2-o-tolyl-5,6,7,8-tetrahydro-pyrido[4,3-d]pyrimidine; |
| 140 | 3-[4-(4-Fluoro-phenyl)-5,6,7,8-tetrahydro-pyrido[4,3-d]pyrimidin-2-yl]-benzonitrile; |
| 141 | 4-(4-Fluoro-phenyl)-2-(2,2,2-trifluoro-1-trifluoromethyl-ethyl)-5,6,7,8-tetrahydro-pyrido[4,3-d]pyrimidine; |
| 142 | 4-(4-Fluoro-phenyl)-2-(1-methyl-cyclopropyl)-5,6,7,8-tetrahydro-pyrido[4,3-d]pyrimidine; |
| 143 | 2-[4-(4-Fluoro-phenyl)-5,6,7,8-tetrahydro-pyrido[4,3-d]pyrimidin-2-yl]-2-methyl-propionic acid; |
| 144 | 2-[4-(4-Fluoro-phenyl)-5,6,7,8-tetrahydro-pyrido[4,3-d]pyrimidin-2-yl]-propionic acid; |
| 145 | 2-(4-Fluoro-cyclohexyl)-4-(4-fluoro-phenyl)-5,6,7,8-tetrahydro-pyrido[4,3-d]pyrimidine; |
| 146 | 2-(4,4-Difluoro-cyclohexyl)-4-(4-fluoro-phenyl)-5,6,7,8-tetrahydro-pyrido[4,3-d]pyrimidine; |
| 147 | 4-(4-Fluoro-phenyl)-2-phenethyl-5,6,7,8-tetrahydro-pyrido[4,3-d]pyrimidine; |
| 148 | 4-Furan-2-yl-2-isopropyl-5,6,7,8-tetrahydro-pyrido[4,3-d]pyrimidine; |
| 149 | 2-Isopropyl-4-(5-methyl-furan-2-yl)-5,6,7,8-tetrahydro-pyrido[4,3-d]pyrimidine; |
| 150 | 4-Furan-3-yl-2-isopropyl-5,6,7,8-tetrahydro-pyrido[4,3-d]pyrimidine; |
| 151 | 4-(5-Fluoro-pyridin-2-yl)-2-isopropyl-5,6,7,8-tetrahydro-pyrido[4,3-d]pyrimidine; |
| 152 | 2-Isopropyl-4-oxazol-2-yl-5,6,7,8-tetrahydro-pyrido[4,3-d]pyrimidine; |
| 153 | 4-(4,5-Dimethyl-oxazol-2-yl)-2-isopropyl-5,6,7,8-tetrahydro-pyrido[4,3-d]pyrimidine; |
| 154 | 2-Isopropyl-4-thiazol-2-yl-5,6,7,8-tetrahydro-pyrido[4,3-d]pyrimidine; |
| 155 | 2-Isopropyl-4-(3H-[1,2,3]triazol-4-yl)-5,6,7,8-tetrahydro-pyrido[4,3-d]pyrimidine; |
| 156 | 2-Isopropyl-4-(2H-pyrazol-3-yl)-5,6,7,8-tetrahydro-pyrido[4,3-d]pyrimidine; |
| 157 | 2-Isopropyl-4-(1H-pyrazol-4-yl)-5,6,7,8-tetrahydro-pyrido[4,3-d]pyrimidine; |
| 158 | 4-(4-Fluoro-phenyl)-2,6-diisopropyl-5,6,7,8-tetrahydro-pyrido[4,3-d]pyrimidine; |
| 159 | 6-Ethyl-4-(4-fluoro-phenyl)-2-isopropyl-5,6,7,8-tetrahydro-pyrido[4,3-d]pyrimidine; |
| 160 | 6-Cyclopropyl-4-(4-fluoro-phenyl)-2-isopropyl-5,6,7,8-tetrahydro-pyrido[4,3-d]pyrimidine; |
| 161 | 6-Cyclobutyl-4-(4-fluoro-phenyl)-2-isopropyl-5,6,7,8-tetrahydro-pyrido[4,3-d]pyrimidine; |
| 162 | 6-Cyclopentyl-4-(4-fluoro-phenyl)-2-isopropyl-5,6,7,8-tetrahydro-pyrido[4,3-d]pyrimidine; |
| 163 | 6-Butyl-4-(4-fluoro-phenyl)-2-isopropyl-5,6,7,8-tetrahydro-pyrido[4,3-d]pyrimidine; |
| 165 | 4-(4-Fluoro-phenyl)-2-isopropyl-5,6,7,8-tetrahydro-pyrido[4,3]pyrimidine, citrate salt; |
| 166 | {2-[2-tert-Butyl-6-(4-fluoro-phenyl)-pyrimidin-4-yl]-ethyl}-methyl-amine; and |
| 167 | {2-[2-tert-Butyl-6-(4-fluoro-phenyl)-pyrimidin-4-yl]-ethyl}-dimethyl-amine. |

Preferably, the compound is 4-(4-fluoro-phenyl)-2-isopropyl-5,6,7,8-tetrahydro-pyrido[4,3-d]pyrimidine or a pharmaceutically acceptable salt thereof.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. Where chemical symbols are used, it is understood that they are read from left to right, and that otherwise their spatial orientation has no significance.

The compounds as described above may be made according to processes within the skill of the art and/or that are described in the schemes and examples that follow. To obtain the various compounds herein, starting materials may be employed that carry the ultimately desired substituents though the reaction scheme with or without protection as appropriate. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", 3$^{rd}$ ed., John Wiley & Sons, 1999. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention. Reactions may be performed between the melting point and the reflux temperature of the solvent, and preferably between 0° C. and the reflux temperature of the solvent.

The pyrimidine compounds of Formulae (I) and (II) may be prepared by a number of reaction schemes. Access to compounds of Formulae (I) and (II) is described in Schemes 1-5. Persons skilled in the art will recognize that certain compounds are more advantageously produced by one scheme as compared to the other. In addition to the Schemes shown below, alternative methods may be used to prepare compounds of Formulae (I) or (II). Such methods are described in U.S. patent application Ser. No. 10/941,664 (Carruthers et al.), which is hereby incorporated by reference.

| Table of Acronyms | |
|---|---|
| Term | Acronym |
| Tetrahydrofuran | THF |
| N,N-Dimethylformamide | DMF |
| N,N-Dimethylacetamide | DMA |
| Dimethyl sulfoxide | DMSO |
| tert-Butylcarbamoyl | Boc |
| High-pressure liquid chromatography | HPLC |
| Thin layer chromatography | TLC |
| N,N-Diisopropylethylamine | DIEA |

Table of Acronyms

| Term | Acronym |
| --- | --- |
| 1,2-Dichloroethane | DCE |
| Ethylene glycol dimethyl ether | DME |
| Acetyl | Ac |
| Diisobutylaluminum hydride | DIBAL-H |
| Ethyl acetate | EtOAc |
| Trifluoroacetic acid | TFA |
| Methanesulfonyl chloride | MsCl |

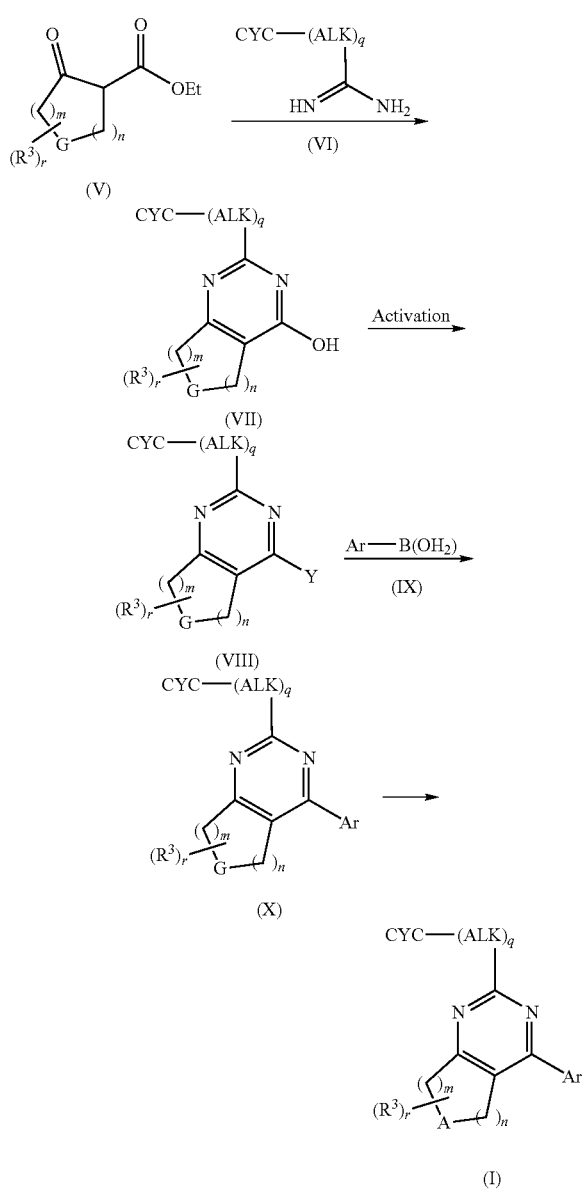

Scheme 1

Referring to Scheme 1, compounds of Formula (I) may be preprared from beta-ketoesters (V), where G may be A or a protected form of A. Where A contains an amine group, the amine moiety may be suitably protected as an alkyl or benzyl amine, amide, carbamate, or other suitable group. Preferred protecting groups for amines include the t-butyl carbamate (Boc) or benzyl groups. Beta-ketoesters (V) are available according to methods known to one skilled in the art. Compounds of formula (V) are reacted with amidines (VI), prepared, for example, in the presence of KOtBu or a tertiary amine base such as $Et_3N$, in a solvent such as tBuOH, at temperatures ranging from room temperature to the reflux temperature of the solvent, to form hydroxy pyrimidines (VII). (See also: U.S. Patent Appl. 60/326,662; Tetrahedron 1989, 45(20), 6511). Pyrimidines (VII) can be converted into precursors for transition metal-catalyzed cross-coupling reactions, such as Stille, Suzuki, Negishi or other such coupling reactions known to one skilled in the art. For example, treatment with $POCl_3$, $PCl_3$, $PCl_5$, $PBr_3$ or $POBr_3$ can afford the corresponding halopyrimidines, where Y is bromide or chloride. Preferably, pyrimidines (VII) are treated with a triflating agent such as trifluoromethane-sulfonic anhydride or N-phenyl-bis(trifluoromethane-sulfonimide) in DCE, $CH_2Cl_2$, THF, or the like, in the presence of a base such as pyridine, $Et_3N$, DIEA, or KOtBu, to provide triflates of formula (VII) where Y is OTf. Coupling of halides or triflates (VIII) with aryl boronic acids (IX), or their boronic ester analogs, in the presence of a catalyst such as $Pd(PPh_3)_4$, $PdCl_2(PPh_3)_2$, $PdCl_2(Pot-ol_3)_2$, $PdCl_2(dppe)$ or $PdCl_2(dppf)$, in a solvent such as THF, 1,4-dioxane, DMA, DMF, DME, toluene, toluene/ethanol, or toluene/$H_2O$ mixtures, in the presence of a base such as $Na_2CO_3$, $K_2CO_3$, $Cs_2CO_3$, $K_3PO_4$, KF, CsF, or KOAc, affords pyrimidines (X). Preferred catalysts are $Pd(PPh_3)_4$ and $PdCl_2(dppf)$, with or without additives such as dppf and catalytic $Bu_4NBr$. Preferred conditions include $PdCl_2(dppf)$, catalytic dppf, and $K_3PO_4$ in 1,4-dioxane.

Where G contains a protecting group, it may be removed using generally accepted methods, or may be otherwise converted into A of Formula (I). More specifically, a group such as a t-butyl carbamate may be removed with an acid such as trifluoroacetic acid or HCl, in a solvent such as $CH_2Cl_2$, dioxane, EtOH, or MeOH to afford compounds of Formula (I). Where G contains a benzyl group, said group may be removed according to standard methods, including hydrogenation in the presence of a palladium catalyst such as Pd/C, in a solvent such as EtOH, or through reaction with 1-chloroethylchloroformate in DCE.

Compounds of formula (X) where G is >NH may be further converted into additional embodiments of Formula (I) wherein A is >$NR^1$ using conventional synthetic methods such as reductive amination or alkylation protocols. Thus, treatment of amines (X) with a suitable aldehyde in the presence of a reductant such as $NaBH_4$, $NaBH_3CN$, $NaBH(OAc)_3$, or $H_{2(g)}$, in the presence of a catalyst, in a solvent such as $CH_2Cl_2$, DCE, THF, EtOH, or MeOH affords compounds of Formula (I) where A is >$NR^1$. One skilled in the art will recognize that the addition of an acid such as AcOH, $Ti(O-iPr)_4$, trifluoroacetic acid, or HCl, may be required. Alternatively, compounds (X) where G is >NH may be treated with an alkylating agent, such as an alkyl chloride, bromide, iodide, mesylate or tosylate, in a solvent such as DMF, DMA, THF, or EtOH, and in the presence of a base such as $NaHCO_3$, $Na_2CO_3$, $K_2CO_3$ or $Cs_2CO_3$ will produce compounds of Formula (I) where A is >$NR^1$.

In the following Schemes, the $R^3$ substituents of Formula (I) and intermediates have been removed to simplify the structural depictions, but one skilled in the art will recognize that the procedures shown provide access to compounds of Formula (I) containing the $R^3$ substituents.

Scheme 2

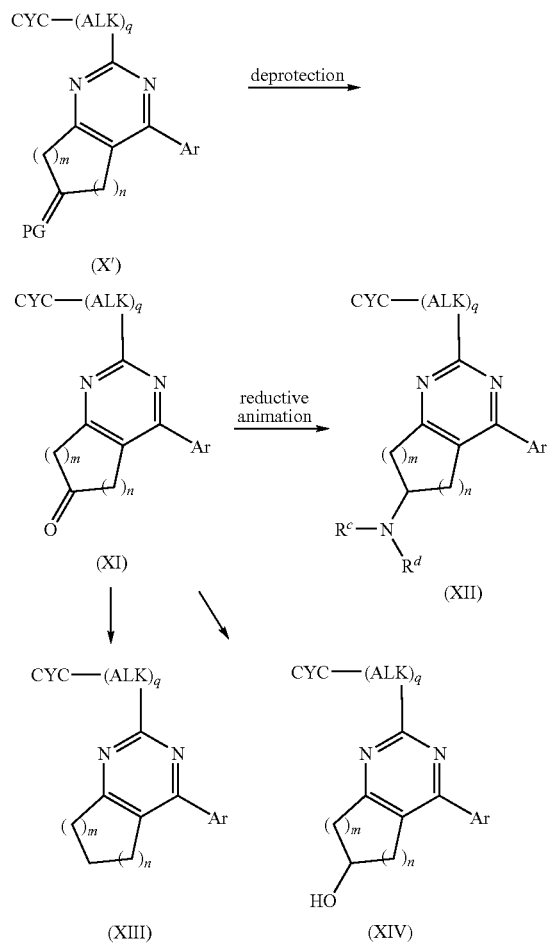

Referring to Scheme 2, compounds of formula (X'), where PG is a ketone protecting group, may be prepared according to the methods described in Scheme 1. Compounds (X') may subsequently be converted into additional embodiments of Formula (I), exemplified by compounds (XII), (XIII), and (XIV). Reductive amination of ketones (XI) may be accomplished as described in Scheme 1. Alternatively, ketones (XI) may be reduced using conventional methods such as $NaBH_4$ in EtOH or DIBAL-H in THF to the corresponding secondary alcohols (XIV), or reduced completely via hydrogenation, Wolff-Kishner reduction, or other protocols to form carbocycles (XIII).

Scheme 3

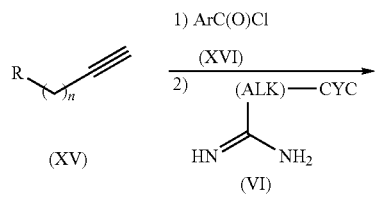

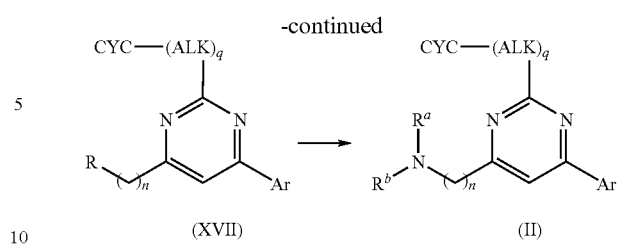

Compounds of Formula (II) may be accessed according to Scheme 3. Alkynes (XV) where R is a suitable protected alcohol or amine are first coupled with a suitable acid chloride (XVI), in the presence of a palladium catalyst such as $Pd(PPh_3)_2Cl_2$, a base such as $Et_3N$, an additive such as CuI, in a solvent such as THF to form intermediate alkynyl ketones. Said ketones are reacted in situ with amidines (VI), under conditions as described in Scheme 1, to form pyrimidines (XVII). Alcohol and amino protecting groups may then be removed under standard conditions. The resulting free amines are themselves compounds of Formula (II), but may be further processed to additional embodiments of Formula (II) via reductive amination as described in Scheme 2. Where a free alcohol is liberated, said alcohol may be converted to —$N(R^a)R^b$ by: 1) formation of a suitable leaving group (an alkyl halide, mesylate, or tosylate); and 2) displacement with $HN(R^a)R^b$. Alternatively, the leaving group may be displaced by treatment with sodium azide. Subsequent reduction of the azido group under Staudinger conditions gives a free amine. In another embodiment, the free alcohol may be oxidized to the corresponding aldehyde using, for example, Dess-Martin periodinane or Swern oxidation conditions, and the resulting aldehyde converted to —$N(R^a)R^b$ using reductive amination methods as described in Scheme 1.

Scheme 4

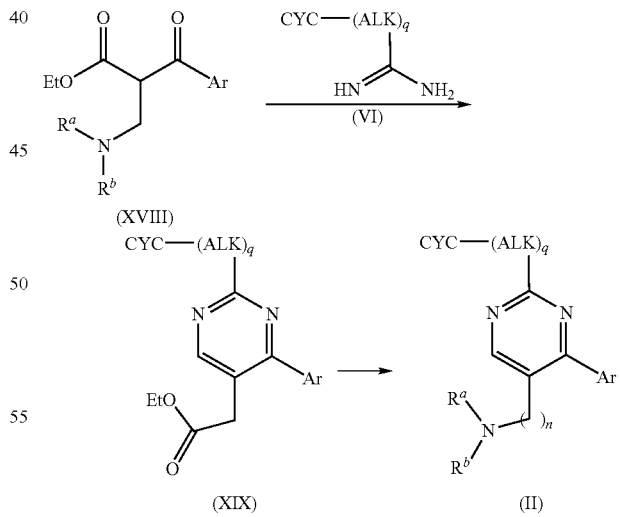

Alternatively, compounds of Formula (II) may be prepared according to Scheme 4. Acrylate esters (XVIII) may be condensed with amidines (VI) as described in Scheme 1 to form pyrimidines (XIX). The pendant ester group may be transformed into amines where n=1 by reduction to the alcohol, and either: 1) oxidizing to the corresponding aldehyde, and performing a reductive amination to install the —$N(R^a)R^b$ substituent; or 2) activating the alcohol as a leaving group such as a tosylate, bromide, or chloride, and displacing with a suitable —HN(R$^a$)R$^b$ reagent. For n=2, the ester may be converted to an amide through peptide coupling methods, and the amide reduced to the corresponding amine. For n=3, homologation procedures known to one skilled in the art may be used to install two carbon units.

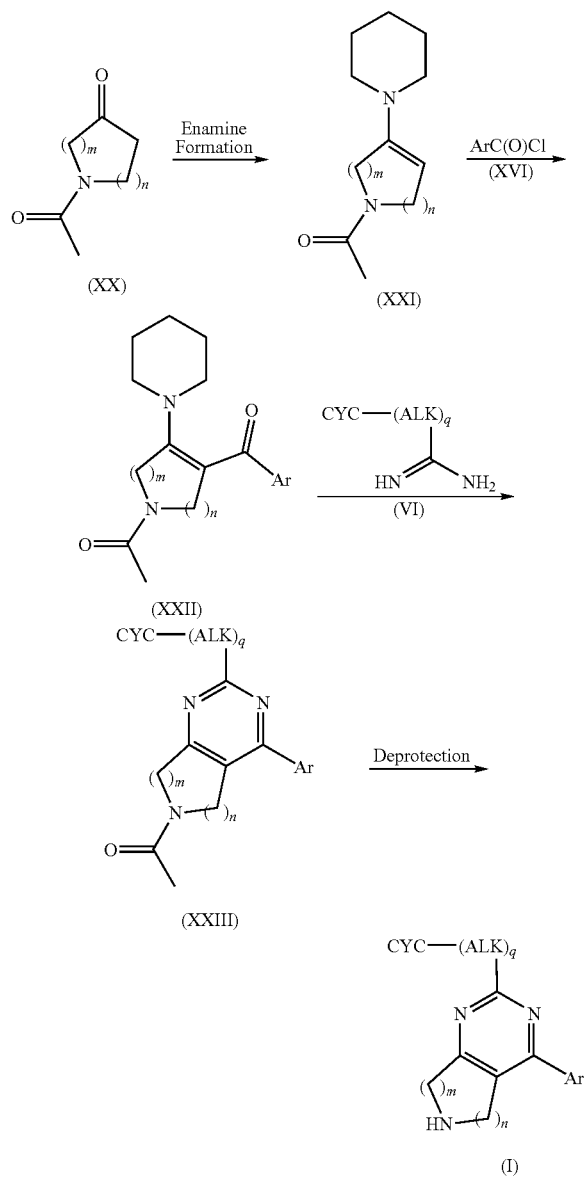

Scheme 5

Compounds of Formula (I) where A is >NH, and m and n are as defined in Formula (I), may be prepared according to Scheme 5. Ketones (XX) are commercially available or may be prepared using methods known to one skilled in the art. The nitrogen protecting group may be an acyl group or carbamoyl group (such as a Boc group). Preferably, the nitrogen protecting group is acetyl. Conversion to enamines of formula (XXI) is performed by reaction with a secondary amine under standard water removal conditions. Preferably, the reaction is done with piperidine as the secondary amine, and using a Dean Stark trap, with a catalyst such as p-toluenesulfonic acid, in a solvent such as toluene. Elevated temperatures are preferred. Enamines are transformed into 1,3-diketones (XXII) by reaction with acyl chlorides (XVI), in the presence of a suitable base such as Et$_3$N, in a solvent such as CH$_2$Cl$_2$. See also: Breitenbucher, et al. PCT Intl. Appl. WO02/014314. Condensation with amidines of formula (VI) to form pyrimidines (XXIII) may be accomplished as described in Scheme 1. Preferably, condensations are accomplished in the presence of Et$_3$N, in a solvent such as t-amyl alcohol, at temperatures between room temperature and reflux temperature of the solvent. Deprotection of the nitrogen protecting group may be effected using conditions known to one skilled in the art. Preferably, where the protecting group is acetyl, deprotection is done in the presence of 10% aqueous HCl at reflux temperature. One skilled in the art will recognize that compounds of Formula (I) prepared in Scheme 5 may be subsequently converted to other embodiments where A is >NR$^2$ as described in Scheme 1.

Compounds of Formulae (I) or (II) may be converted to their corresponding salts using methods known to those skilled in the art. For example, amines of Formulae (I) or (II) may be treated with trifluoroacetic acid, HCl, or citric acid in a solvent such as MeOH to provide the corresponding salt forms.

Compounds prepared according to the schemes described above may be obtained as single enantiomers, diastereomers, or regioisomers, or as racemic mixtures or mixtures of enantiomers, diastereomers, or regioisomers. Where regioisomeric or diastereomeric mixtures are obtained, isomers may be separated using conventional methods such as chromatography or crystallization. Where racemic (1:1) and non-racemic (not 1:1) mixtures of enantiomers are obtained, single enantiomers may be isolated using conventional separation methods known to one skilled in the art. Particularly useful separation methods may include chiral chromatography, recrystallization, resolution, diastereomeric salt formation, or derivatization into diastereomeric adducts followed by separation.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with a compound of Formula (I) or (II) or with a compound that converts to a compound of Formula (I) or (II) in vivo after administration to the patient. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

For therapeutic use, salts of the compounds of the present invention are those that are pharmaceutically acceptable. However, salts of acids and bases that are non-pharmaceutically acceptable may also find use, for example, in the preparation or purification of a pharmaceutically acceptable compound. All salts, whether pharmaceutically acceptable or not are included within the ambit of the present invention.

Pharmaceutically acceptable salts, esters, and amides of compounds according to the present invention refer to those salt, ester, and amide forms of the compounds of the present invention which would be apparent to the pharmaceutical chemist, i.e., those that are non-toxic and that would favorably affect the pharmacokinetic properties of said compounds of the present invention. Those compounds having favorable pharmacokinetic properties would be apparent to the pharmaceutical chemist, i.e., those which are non-toxic and which possess such pharmacokinetic properties to provide sufficient palatability, absorption, distribution, metabolism and excretion. Other factors, more practical in nature, which are also important in the selection, are cost of raw materials, ease of crystallization, yield, stability, hygroscopicity and flowability of the resulting bulk drug.

Examples of acids that may be used in the preparation of pharmaceutically acceptable salts include the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Compounds of the present invention containing acidic protons may be converted into their therapeutically active non-toxic metal or amine addition salt forms by treatment with appropriate organic and inorganic bases. Appropriate base salt forms comprise, for example, the ammonium salts; the alkali and earth alkaline metal salts (e.g. lithium, sodium, potassium, magnesium, calcium salts, which may be prepared by treatment with, for example, magnesium hydroxide, calcium hydroxide, potassium hydroxide, zinc hydroxide, or sodium hydroxide); and amine salts made with organic bases (e.g. primary, secondary and tertiary aliphatic and aromatic amines such as L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine). See, e.g., S. M. Berge, et al., "Pharmaceutical Salts", J. Pharm. Sci., 1977, 66:1-19, and *Handbook of Pharmaceutical Salts, Propertions, Selection, and Use*; Stahl, P. H., Wermuth, C. G., Eds.; Wiley-VCH and VHCA: Zurich, 2002, which are incorporated herein by reference.

Pharmaceutically acceptable esters and amides are those that are within a reasonable benefit/risk ratio, pharmacologically effective and suitable for contact with the tissues of patients without undue toxicity, irritation, or allergic response. Representative pharmaceutically acceptable amides of the invention include those derived from ammonia, primary $C_{1-6}$alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-12}$alkyl)amines.

Representative pharmaceutically acceptable esters of the invention include $C_{1-7}$alkyl, $C_{5-7}$cycloalkyl, phenyl, substituted phenyl, and phenyl$C_{1-6}$alkyl-esters. Preferred esters include methyl esters. Furthermore, examples of suitable esters include such esters where one or more carboxyl substituents is replaced with p-methoxybenzyloxy-carbonyl, 2,4,6-trimethylbenzyloxy-carbonyl, 9-anthryloxycarbonyl, $CH_3SCH_2COO$—, tetrahydrofur-2-yloxycarbonyl, tetrahydropyran-2-yloxy-carbonyl, fur-2-yloxycarbonyl, benzoylmethoxy-carbonyl, p-nitrobenzyloxy-carbonyl, 4-pyridylmethoxycarbonyl, 2,2,2-trichloro-ethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxy-carbonyl, 2-benzyloxyphenyloxycarbonyl, 4-methylthiophenyloxycarbonyl, or tetrahydropyran-2-yloxycarbonyl.

The compounds of the present invention are serotonin receptor modulators, and as such, the compounds are useful in the treatment of serotonin-mediated disease states. Particularly, the compounds may be used in methods for treating or preventing CNS disorders, such as sleep disorders, depression/anxiety, generalized anxiety disorder, schizophrenia, bipolar disorders, cognitive disorders, mild cognitive impairment, Alzheimer's disease, Parkinson's disease, psychotic disorders, phobic disorders, obsessive-compulsive disorder, mood disorders, post-traumatic stress and other stress-related disorders, migraine, pain, eating disorders, obesity, sexual dysfunction, metabolic disturbances, hormonal imbalance, hot flushes associated with menopause, alcohol abuse, drug abuse, addictive disorders including drug addiction and alcohol addiction, nausea, inflammation, centrally mediated hypertension, sleep/wake disturbances, jetlag, and circadian rhythm abnormalities. The compounds may also be used in the treatment and prevention of hypotension, peripheral vascular disorders, cardiovascular shock, renal disorders, gastric motility, diarrhea, spastic colon, irritable bowel disorders, ischemias, septic shock, urinary incontinence, and other disorders related to the gastrointestinal and vascular systems. In addition, compounds of the present invention may be used in methods for treating or preventing a range of ocular disorders including glaucoma, optic neuritis, diabetic retinopathy, retinal edema, and age-related macular degeneration.

The compounds of the present invention are 5-$HT_7$ modulators and many are 5-$HT_7$ antagonists. As such, the compounds are useful in methods for treating or preventing 5-$HT_7$-mediated disease states. Where the compounds possess substantial 5-$HT_7$ antagonist activity, they may be particularly useful in methods for treating or preventing depression/anxiety, sleep/wake disturbances, jetlag, migraine, urinary incontinence, gastric motility, and irritable bowel disorders.

Many of the compounds of the present invention are 5-$HT_2$ modulators and many are 5-$HT_2$ antagonists. As such, the compounds are useful in methods for treating or preventing 5-$HT_2$-mediated diseases and conditions. Where the compounds possess substantial 5-$HT_2$ antagonist activity, they may be particularly useful in methods for treating or preventing depression/anxiety, generalized anxiety disorder, schizophrenia, bipolar disorders, psychotic disorders, obsessive-compulsive disorder, mood disorders, post-traumatic stress disorders, sleep disturbances, sexual dysfunction, hot flushes associated with menopause, eating disorders, migraine, addictive disorders, and peripheral vascular disorders.

The compounds of the present invention are 5-HT$_6$ modulators and many are 5-HT$_6$ antagonists. As such, the compounds are useful in methods for treating or preventing 5-HT$_6$-mediated disease states. Where the compounds possess substantial 5-HT$_6$ antagonist activity, they may be particularly useful in methods for treating or preventing schizophrenia, cognitive disorders, mild cognitive impairment, Alzheimer's disease, and Parkinson's disease.

Said methods of treating and preventing comprise the step of administering to a mammal suffering therefrom an effective amount of at least one compound of the present invention.

The present invention also contemplates a method of treating or preventing a serotonin-mediated disease or condition with a combination therapy, comprising administering at least one compound of the present invention in combination with one or more neuroactive agents. Suitable neuroactive agents include: selective serotonin reuptake inhibitors (SSRIs), antipsychotics, norepinephrine reuptake inhibitors (NRIs), sedatives, monoamine oxidase inhibitors (MAOs), and tricyclic antidepressants (TCAs). In another embodiment, the present invention includes compositions comprising at least one compound of the present invention and one or more neuroactive agent.

Compounds of the present invention may be administered in pharmaceutical compositions to treat patients (humans and other mammals) with disorders mediated by the serotonin receptor. Thus, the invention features pharmaceutical compositions containing at least one compound of the present invention and a pharmaceutically acceptable carrier. A composition of the invention may further include at least one other therapeutic agent (for example, a combination formulation or combination of differently formulated active agents for use in a combination therapy method).

The present invention also features methods of using or preparing or formulating such pharmaceutical compositions. The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes, or by inhalation. Preparations may also be designed to give slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinyl-pyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or may be presented as a dry product for reconstitution with water or other suitable vehicles before use. Compositions of such liquid may contain pharmaceutically-acceptable excipients such as suspending agents (for example, sorbitol, methyl cellulose, sodium alginate, gelatin, hydroxyethylcellulose, carboxymethylcellulose, aluminium stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation consisting of the compound of the invention and a suitable carrier.

Methods are known in the art for determining effective doses for therapeutic (treatment) and prophylactic (preventative) purposes for the pharmaceutical compositions or the drug combinations of the present invention, whether or not formulated in the same composition. The specific dosage level required for any particular patient will depend on a number of factors, including severity of the condition being treated, the route of administration, and the weight of the patient. For therapeutic purposes, "effective dose" or "effective amount" refers to that amount of each active compound or pharmaceutical agent, alone or in combination, that elicits the biological or medicinal response in a tissue system, animal, or human that is being sought by a researcher, veterinarian, medical doctor, or other clinician, which includes alleviation of the symptoms of the disease or disorder being treated. For prophylactic purposes (i.e., preventing or inhibiting the onset or progression of a disorder), the term "effective dose" or "effective amount" refers to that amount of each active compound or pharmaceutical agent, alone or in combination, that inhibits in a subject the onset or progression of a disorder as being sought by a researcher, veterinarian, medical doctor, or other clinician, the delaying of which disorder is mediated, at least in part, by the modulation of the serotonin receptor. Methods of combination therapy include co-administration of a single formulation containing all active agents; essentially contemporaneous administration of more than one formulation; and administration of two or more active agents separately formulated.

It is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

Preferably, oral doses range from about 0.05 to 200 mg/kg, daily, taken in 1 to 4 separate doses. Some compounds of the invention may be orally dosed in the range of about 0.05 to about 50 mg/kg daily, others may be dosed at 0.05 to about 20 mg/kg daily, while still others may be dosed at 0.1 to about 10 mg/kg daily. Infusion doses can range from about 1 to 1000 μg/kg/min of inhibitor, admixed with a pharmaceutical carrier over a period ranging from several minutes to several days. For topical administration compounds of the present invention may be mixed with a pharmaceutical carrier at a concentration of about 0.1% to about 10% of drug to vehicle.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

Preparative Reversed-Phase HPLC was performed as follows:

Method A. Instrument, Hewlett Packard Series 1100; Column, Agilent ZORBAX® Bonus RP, 5 μm, 4.6×250 mm; Flow rate, 1 mL/min; Detection, λ=220 & 254 nm; Gradient, 1 to 99% acetonitrile/water, 0.05% trifluoroacetic acid over 20 min.

Method B. Instrument, Hewlett Packard HPLC; Column, Agilent ZORBAX® Eclipse XDB-C8, 5 μm, 4.6×150 mm; Flow rate, 1 mL/min; Detection, λ=220 & 254 nm; Gradient, 1 to 99% acetonitrile/water, 0.05% trifluoroacetic acid over 8 min.

Mass spectra were obtained on an Agilent series 1100 MSD using electrospray ionization (ESI) in either positive or negative modes as indicated.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

NMR spectra were obtained on either a Bruker model DPX400 (400 MHz), DPX500 (500 MHz), or DPX600 (600 MHz) spectrometer. The format of the $^1$H NMR data below is: chemical shift in ppm down field of the tetramethylsilane reference (multiplicity, coupling constant J in Hz, integration).

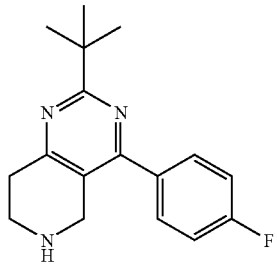

Example 1

2-tert-Butyl-4-(4-fluoro-phenyl)-5,6,7,8-tetrahydro-pyrido[4,3-d]pyrimidine

Step A. 2-tert-Butyl-4-(4-fluoro-phenyl)-5,6,7,8-tetrahydro-pyrido[4,3-d]pyrimidine hydrochloride. To a tert-BuOH (17 mL) solution of 4-oxo-piperidine-1,3-dicarboxylic acid-1-tert-butyl ester-3-ethyl ester (2.18 g, 8.05 mmol), and 2,2-dimethyl-propionamidine hydrochloride (1.0 g, 7.3 mmol) was added Et$_3$N (3.0 mL, 22.0 mmol). The reaction solution was heated at reflux for 48 h, cooled to rt, and concentrated. The resulting solid was dissolved in CH$_2$Cl$_2$ and washed with water. The aqueous layer was extracted with CH$_2$Cl$_2$. The combined organic layers were dried and concentrated to give a yellow solid that was triturated with Et$_2$O to give 1.74 g (70%) of the title compound as a white solid. MS (ESI): exact mass calcd. for $C_{16}H_{25}N_3O_3$, 307.19; m/z found, 308.4 [M+H]$^+$. $^1$H NMR (CDCl$_3$): 4.35 (s, 2H), 3.68-3.67 (m, 2H), 2.74-2.65 (m, 2H), 1.49 (s, 9H), 1.37 (s, 9H).

Step B. 2-tert-Butyl-4-trifluoromethanesulfonyloxy-7,8-dihydro-5H-pyrido[4,3-d]pyrimidine-6-carboxylic acid tert-butyl ester. To a 0° C. solution of the product from Step A (1.0 g, 3.25 mmol) in CH$_2$Cl$_2$ (16 mL) was added Et$_3$N (0.53 mL, 3.80 mmol) and trifluoromethanesulfonic anhydride (0.64 mL, 3.8 mmol) dropwise over 10 min. After 2 h at 0° C., the mixture was diluted with CH$_2$Cl$_2$ and washed with water. The aqueous layer was extracted with CH$_2$Cl$_2$. The combined organic layers were dried and concentrated. The resulting residue was purified via SiO$_2$ chromatography (10-30% EtOAc/hexanes) to give 1.28 g (91%) of the title compound. MS (ESI): exact mass calcd. for $C_{17}H_{24}F_3N_3O_3S$, 439.14; m/z found, 440.3 [M+H]$^+$. $^1$H NMR (CDCl$_3$): 4.56 (s, 2H), 3.77 (t, J=5.7, 2H), 2.99-2.95 (m, 2H), 1.50 (s, 9H), 1.36 (s, 9H).

Step C. 2-tert-Butyl-4-(4-fluoro-phenyl)-7,8-dihydro-5H-pyrido[4,3-d]pyrimidine-6-carboxylic acid tert-butyl ester. To the product from Step B (0.17 g, 0.39 mmol) was added 4-fluorophenylboronic acid (0.082 g, 0.586 mmol), K$_3$PO$_4$ (0.124 g, 0.584 mmol), Pd(Cl)$_2$dppf.CH$_2$Cl$_2$ (0.018 g, 0.022 mmol) and dppf (0.008 g, 0.014 mmol). The mixture was evacuated with N$_2$, dioxane (4 mL) was added and the mixture was heated at reflux for 2 h. After cooling to room temperature (rt), the mixture was diluted with Et$_2$O, filtered through a small SiO$_2$ plug, and the filtrate was concentrated. The resulting residue was purified via SiO$_2$ chromatography (5-30% EtOAc/hexanes) to give 0.134 g (89%) of the title compound. MS (ESI): exact mass calcd. for $C_{22}H_{28}FN_3O_2$, 385.22; m/z found, 386.4 [M+H]$^+$. $^1$H NMR (CDCl$_3$): 7.60 (dd, J=5.4, 8.8, 2H), 7.17-7.14 (m, 2H), 4.59 (s, 2H), 3.76 (t, J=6.1, 2H), 3.09 (t, J=6.1, 2H), 1.44 (s, 9H), 1.41 (s, 9H).

Step D. 2-tert-Butyl-4-(4-fluoro-phenyl)-5,6,7,8-tetrahydro-pyrido[4,3-d]pyrimidine hydrochloride. To an EtOAc solution of the product from Step D (0.130 g, 0.337 mmol) was added 4 M HCl in dioxane. After stirring for 18 h the volatiles were removed and the solid partitioned between water and EtOAc. The aqueous layer was made basic with 1 N NaOH and extracted with EtOAc (2×). The combined organic layers were dried with MgSO$_4$, filtered and concentrated. The resulting residue was purified via SiO$_2$ chromatography (1-7% 2 M NH$_3$ in MeOH/CH$_2$Cl$_2$) to give 0.079 g (82%) of the title compound. The corresponding HCl salt was obtained upon treatment of the free base in Et$_2$O with 1 M HCl in Et$_2$O. MS (ESI): exact mass calcd. for C$_{17}$H$_{20}$FN$_3$, 285.16; m/z found, 286.4 [M+H]$^+$. $^1$H NMR (DMSO-d$_6$): 9.74 (s, 2H), 7.71 (dd, J=5.5, 8.6, 2H), 7.42 (d, J=8.8, 2H), 4.31 (m, 2H), 3.49-3.48 (m, 2H), 3.16 (t, J=6.2, 2H), 1.38 (s, 9H).

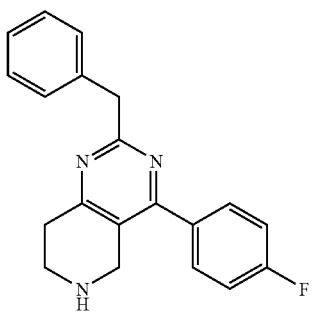

Example 2

2-Benzyl-4-(4-fluoro-phenyl)-5,6,7,8-tetrahydro-pyrido[4,3-d]pyrimidine

Step A. 2-Benzyl-4-trifluoromethanesulfonyloxy-7,8-dihydro-5H-pyrido[4,3-d]pyrimidine-6-carboxylic acid tert-butyl ester. To a solution of 2-benzyl-4-hydroxy-7,8-dihydro-5H-pyrido[4,3-d]pyrimidine-6-carboxylic acid tert-butyl ester (2.0 g, 5.9 mmol; prepared from 2-phenyl-acetamidine hydrochloride as described in Example 1, Step A) in THF (15 mL) was added KOtBu (0.408 g, 3.6 mmol). After 15 min, the mixture was treated with N-phenyl-bis(trifluoromethanesulfonimide) (1.18 g, 3.3 mmol) and the mixture was stirred for 18 h. The mixture was diluted with water and extracted with EtOAc (2×). The combined organic layers were dried and concentrated. The resulting residue was purified via SiO$_2$ chromatography (10-40% EtOAc/hexanes) to give 1.15 g (81%) of the title compound which was contaminated with byproducts from N-phenyl-bis(trifluoromethanesulfonimide).

Step B. 2-Benzyl-4-(4-fluoro-phenyl)-7,8-dihydro-5H-pyrido[4,3-d]pyrimidine-6-carboxylic acid tert-butyl ester. The title compound was prepared as described in Example 1, Step C. MS (ESI): exact mass calcd. for C$_{25}$H$_{26}$FN$_3$O$_2$, 419.20; m/z found, 420.5 [M+H]$^+$. $^1$H NMR (CDCl$_3$): 7.53 (dd, J=5.3, 8.7, 2H), 7.43-7.41 (m, 2H), 7.31-7.28 (m, 2H), 7.23-7.14 (m, 3H), 4.55 (s, 2H), 4.27 (s, 2H), 3.75 (t, J=6.1, 2H), 3.00 (t, J=6.0, 2H), 1.43 (s, 9H).

Step C. 2-Benzyl-4-(4-fluoro-phenyl)-5,6,7,8-tetrahydro-pyrido[4,3-d]pyrimidine. A solution of the product from Step B (0.131 g, 0.312 mmol) in CH$_2$Cl$_2$ was treated with TFA. After stirring for 4 h, the mixture was concentrated and partitioned between saturated (satd.) aq. NaHCO$_3$ and CH$_2$Cl$_2$ (2×). The combined organic layers were dried and concentrated. The resulting residue was purified via SiO$_2$ chromatography (1-7% 2 M NH$_3$ in MeOH/CH$_2$Cl$_2$) to give 0.084 g (84%) of the title compound. MS (ESI): exact mass calcd. for C$_{20}$H$_{18}$FN$_3$, 319.15; m/z found, 320.4 [M+H]$^+$. $^1$H NMR (CDCl$_3$): 7.51 (dd, J=5.4, 8.8, 2H), 7.41 (d, J=7.4, 2H), 7.31-7.27 (m, 2H), 7.22-7.19 (m, 1H), 7.15 (dd, J=8.7, 2H), 4.27 (s, 2H), 3.95 (s, 2H), 3.24 (t, J=6.1, 2H), 2.97 (t, J=6.1, 2H).

Unless otherwise specified, the compounds in Examples 3-57 were prepared using methods similar to those described in Examples 1 and 2, utilizing the appropriate β-ketoesters, amidine hydrochlorides, and arylboronic acids.

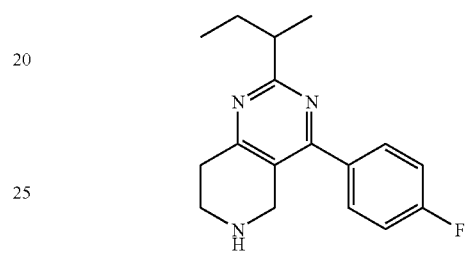

Example 3

2-sec-Butyl-4-(4-fluoro-phenyl)-5,6,7,8-tetrahydro-pyrido[4,3-d]pyrimidine hydrochloride MS (ESI): exact mass calcd. for C$_{17}$H$_{20}$FN$_3$, 285.16; m/z found, 286.4 [M+H]$^+$. $^1$H NMR (DMSO-d$_6$): 9.72 (s, 2H), 7.69 (dd, J=5.5, 8.8, 2H), 7.42 (dd, J=8.8, 2H), 4.33-4.27 (m, 2H), 3.52-3.44 (m, 2H), 3.16 (t, J=6.4, 2H), 2.96-2.88 (m, 1H), 1.88-1.77 (m, 1H), 1.66-1.56 (m, 1H), 1.26 (d, J=6.9, 3H), 0.83 (t, J=7.4, 3H).

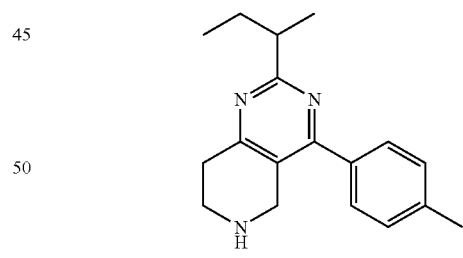

Example 4

2-sec-Butyl-4-p-tolyl-5,6,7,8-tetrahydro-pyrido[4,3-d]pyrimidine hydrochloride

MS (ESI): exact mass calcd. for C$_{21}$H$_{21}$N$_3$, 281.19; m/z found, 282.5 [M+H]$^+$. $^1$H NMR (DMSO-d$_6$): 9.69 (s, 2H), 7.52 (d, J=8.1, 2H), 7.38 (d, J=7.4?, 2H), 4.33-4.26 (m, 2H), 3.52-3.54 (m, 2H), 3.15 (t, J=6.3, 2H), 2.96-2.87 (m, 1H), 2.92 (m, 1H), 2.40 (s, 3H), 1.88-1.77 (m, 1H), 1.67-1.55 (m, 1H), 1.26 (d, J=6.9, 3H), 0.83 (t, J=7.4, 3H).

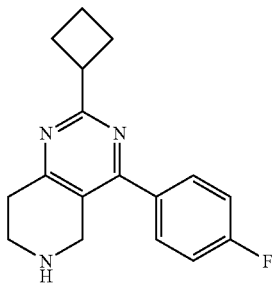

Example 5

2-Cyclobutyl-4-(4-fluoro-phenyl)-5,6,7,8-tetrahydro-pyrido[4,3-d]pyrimidine hydrochloride MS (ESI): exact mass calcd. for $C_{17}H_{18}FN_3$, 283.15; m/z found, 284.3 [M+H]$^+$. $^1$H NMR (DMSO-d$_6$): 9.72 (m, 2H), 7.70 (dd, J=5.5, 8.8, 2H), 7.44-7.40 (m, 2H), 4.32-4.26 (m, 2H), 3.79-3.73 (m, 1H), 3.50-3.45 (m, 2H), 3.16 (t, J=6.4, 2H), 2.42-2.27 (m, 4H), 2.08-1.99 (m, 1H), 1.91-1.83 (m, 1H).

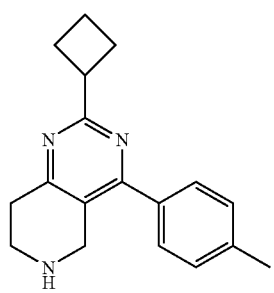

Example 6

2-Cyclobutyl-4-p-tolyl-5,6,7,8-tetrahydro-pyrido[4,3-d]pyrimidine

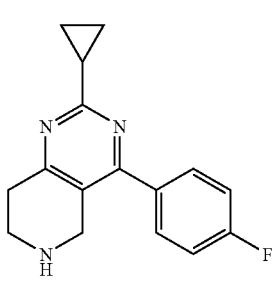

Example 7

2-Cyclopropyl-4-(4-fluoro-phenyl)-5,6,7,8-tetrahydro-pyrido[4,3-d]pyrimidine

MS (ESI): exact mass calcd. for $C_{16}H_{16}FN_3$, 269.13; m/z found, 270.3 [M+H]$^+$. $^1$H NMR (DMSO-d$_6$): 9.81 (m, 2H), 7.67 (dd, J=5.4, 8.6, 2H), 7.40 (dd, J=8.8, 2H), 4.26-4.22 (m, 2H), 3.48-3.42 (m, 2H), 3.11 (t, J=6.3, 2H), 2.24-2.19 (m, 1H), 1.08-1.01 (m, 4H).

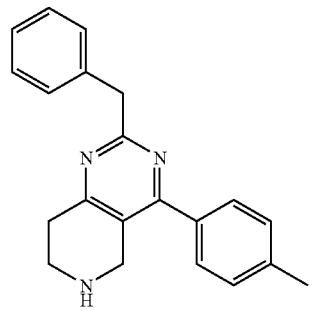

Example 8

2-Benzyl-4-p-tolyl-5,6,7,8-tetrahydro-pyrido[4,3-d]pyrimidine

MS (ESI): exact mass calcd. for $C_{21}H_{21}N_3$, 315.17; m/z found, 316.4 [M+H]$^+$. $^1$H NMR (CDCl$_3$): 7.43-7.41 (m, 4H), 7.30-7.25 (m, 4H), 7.21-7.18 (m, 1H), 4.27 (s, 2H), 3.97 (s, 2H), 3.23 (t, J=6.1, 2H), 2.96 (t, J=6.1, 2H), 2.40 (s, 3H).

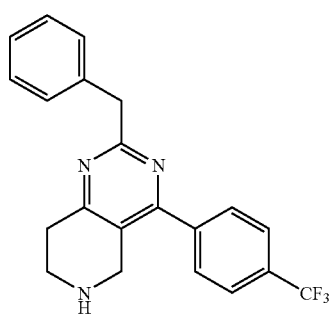

Example 9

2-Benzyl-4-(4-trifluoromethyl-phenyl)-5,6,7,8-tetrahydro-pyrido[4,3-d]pyrimidine

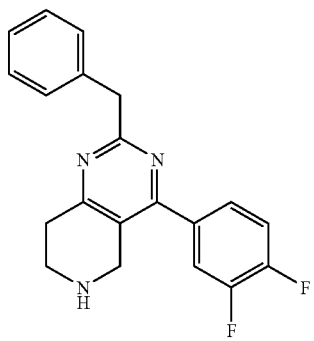

Example 10

2-Benzyl-4-(3,4-difluoro-phenyl)-5,6,7,8-tetrahydro-pyrido[4,3-d]pyrimidine

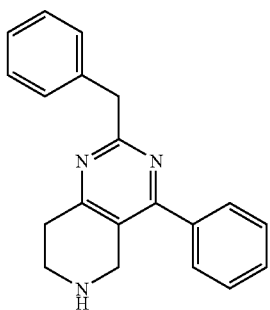

Example 11

2-Benzyl-4-phenyl-5,6,7,8-tetrahydro-pyrido[4,3-d]pyrimidine

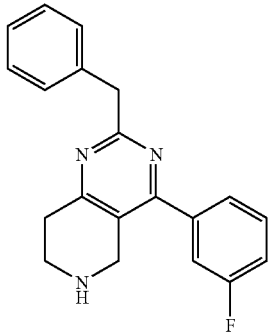

Example 12

2-Benzyl-4-(3-fluoro-phenyl)-5,6,7,8-tetrahydro-pyrido[4,3-d]pyrimidine

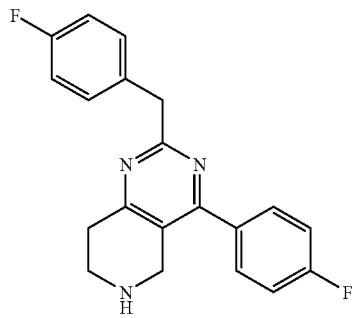

Example 13

2-(4-Fluoro-benzyl)-4-(4-fluoro-phenyl)-5,6,7,8-tetrahydro-pyrido[4,3-d]pyrimidine MS (ESI): exact mass calcd. for $C_{20}H_{17}F_2N_3$, 337.14; m/z found, 338.4 [M+H]$^+$. $^1$H NMR (CDCl$_3$): 7.53-7.49 (m, 2H), 7.38-7.35 (m, 2H), 7.18-7.13 (m, 2H), 6.99-6.95 (m, 2H), 4.23 (s, 2H), 3.96 (s, 2H), 3.25 (t, J=6.1, 2H), 2.97 (t, J=6.1, 2H).

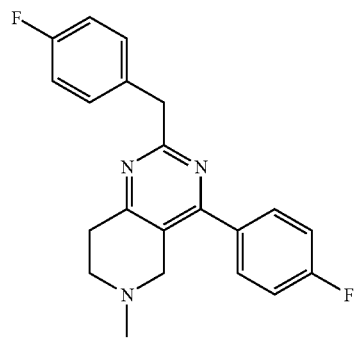

Example 14

2-(4-Fluoro-benzyl)-4-(4-fluoro-phenyl)-6-methyl-5,6,7,8-tetrahydro-pyrido[4,3-d]pyrimidine

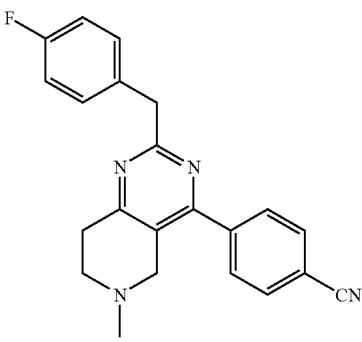

Example 15

4-[2-(4-Fluoro-benzyl)-6-methyl-5,6,7,8-tetrahydro-pyrido[4,3-d]pyrimidin-4-yl]-benzonitrile

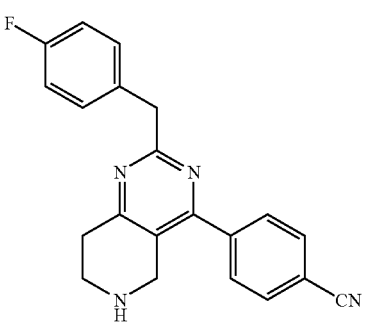

Example 16

4-[2-(4-Fluoro-benzyl)-5,6,7,8-tetrahydro-pyrido[4,3-d]pyrimidin-4-yl]-benzonitrile

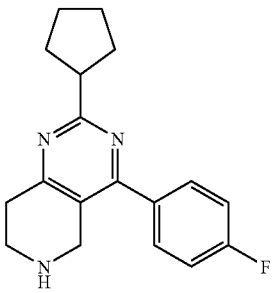

Example 17

2-Cyclopentyl-4-(4-fluoro-phenyl)-5,6,7,8-tetrahydro-pyrido[4,3-d]pyrimidine

MS (ESI): exact mass calcd. for $C_{18}H_{20}FN_3$, 297.16; m/z found, 298.4 [M+H]$^+$. $^1$H NMR (CDCl$_3$): 7.55 (dd, J=5.4, 8.8, 2H), 7.15 (t, J=8.8, 2H), 3.97 (s, 2H), 3.36-3.28 (m, 1H), 3.26 (t, J=6.1, 2H), 2.97 (t, J=6.1, 2H), 2.12-1.64 (m, 8H).

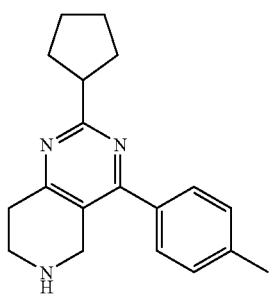

Example 18

2-Cyclopentyl-4-p-tolyl-5,6,7,8-tetrahydro-pyrido[4,3-d]pyrimidine

MS (ESI): exact mass calcd. for $C_{19}H_{23}N_3$, 293.19; m/z found, 294.5 [M+H]$^+$. $^1$H NMR (CDCl$_3$): 7.55 (dd, J=5.4, 8.8, 2H), 7.15 (t, J=8.8, 2H), 3.97 (s, 2H), 3.36-3.27 (m, 1H), 3.26 (t, J=6.1, 2H), 2.97 (t, J=6.1, 2H), 2.12-1.64 (m, 8H).

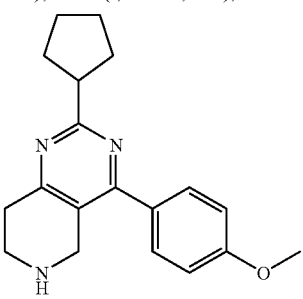

Example 19

2-Cyclopentyl-4-(4-methoxy-phenyl)-5,6,7,8-tetrahydro-pyrido[4,3-d]pyrimidine

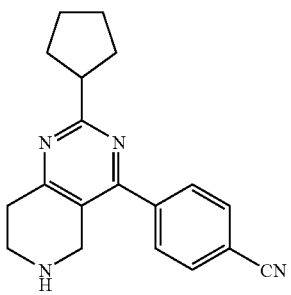

Example 20

4-(2-Cyclopentyl-5,6,7,8-tetrahydro-pyrido[4,3-d]pyrimidin-4-yl)-benzonitrile

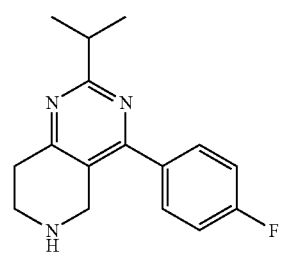

Example 21

4-(4-Fluoro-phenyl)-2-isopropyl-5,6,7,8-tetrahydro-pyrido[4,3-d]pyrimidine hydrochloride MS (ESI): exact mass calcd. for $C_{16}H_{18}FN_3$, 271.15; m/z found, 272.4 [M+H]$^+$. $^1$H NMR (MeOH-d$_4$): 7.75-7.70 (m, 2H), 7.37-7.31 (m, 2H), 4.47 (s, 2H), 3.72-3.68 (m, 2H), 3.37-3.32 (m, 2H), 3.30-3.22 (m, 1H), 1.39 (d, J=6.9, 6H).

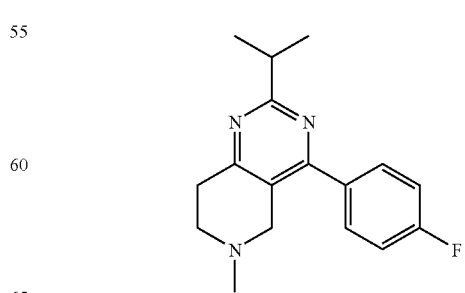

Example 22

4-(4-Fluoro-phenyl)-2-isopropyl-6-methyl-5,6,7,8-tetrahydro-pyrido[4,3-d]pyrimidine

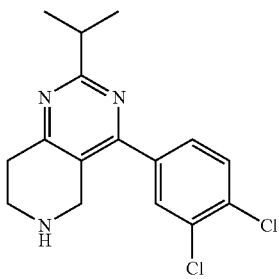

Example 23

4-(3,4-Dichloro-phenyl)-2-isopropyl-5,6,7,8-tetrahydro-pyrido[4,3-d]pyrimidine hydrochloride MS (ESI): exact mass calcd. for $C_{16}H_{17}Cl_2N_3$, 321.08; m/z found, 322.3 [M+H]$^+$. $^1$H NMR (MeOH-d$_4$): 7.86-7.84 (m, 1H), 7.77-7.74 (m, 1H), 7.60-7.57 (m, 1H), 4.47 (s, 2H), 3.71-3.67 (m, 2H), 3.35-3.32 (m, 2H), 3.29-3.21 (m, 1H), 1.38 (d, J=6.9, 6H).

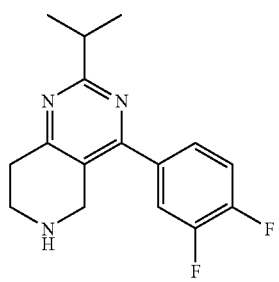

Example 24

4-(3,4-Difluoro-phenyl)-2-isopropyl-5,6,7,8-tetrahydro-pyrido[4,3-d]pyrimidine hydrochloride MS (ESI): exact mass calcd. for $C_{16}H_{17}F_2N_3$, 289.14; m/z found, 290.4 [M+H]$^+$. $^1$H NMR (MeOH-d$_4$): 7.67-7.62 (m, 1H), 7.54-7.47 (m, 2H), 4.48 (s, 2H), 3.71-3.67 (m, 2H), 3.35-3.32 (m, 2H), 3.29-3.21 (m, 1H), 1.38 (d, J=6.9, 6H).

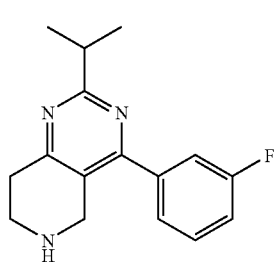

Example 25

4-(3-Fluoro-phenyl)-2-isopropyl-5,6,7,8-tetrahydro-pyrido[4,3-d]pyrimidine

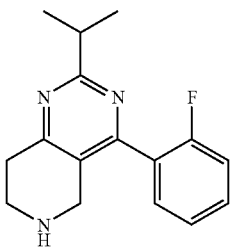

Example 26

4-(2-Fluoro-phenyl)-2-isopropyl-5,6,7,8-tetrahydro-pyrido[4,3-d]pyrimidine

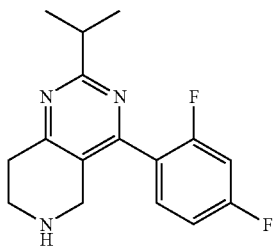

Example 27

4-(2,4-Difluoro-phenyl)-2-isopropyl-5,6,7,8-tetrahydro-pyrido[4,3-d]pyrimidine

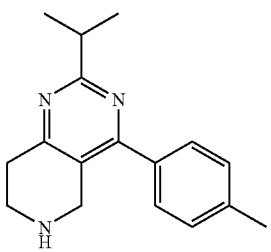

Example 28

2-Isopropyl-4-p-tolyl-5,6,7,8-tetrahydro-pyrido[4,3-d]pyrimidine

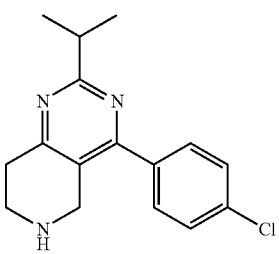

Example 29

4-(4-Chloro-phenyl)-2-isopropyl-5,6,7,8-tetrahydro-pyrido[4,3-d]pyrimidine

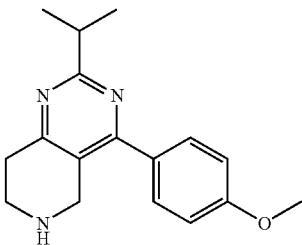

Example 30

2-Isopropyl-4-(4-methoxy-phenyl)-5,6,7,8-tetrahydro-pyrido[4,3-d]pyrimidine

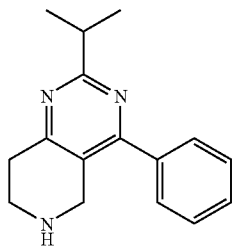

Example 31

2-Isopropyl-4-phenyl-5,6,7,8-tetrahydro-pyrido[4,3-d]pyrimidine

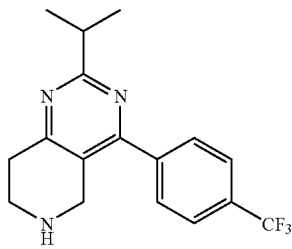

Example 32

2-Isopropyl-4-(4-trifluoromethyl-phenyl)-5,6,7,8-tetrahydro-pyrido[4,3-d]pyrimidine

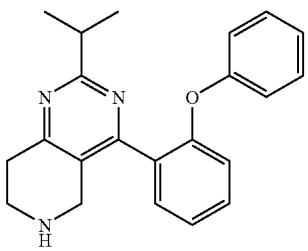

Example 33

2-Isopropyl-4-(2-phenoxy-phenyl)-5,6,7,8-tetrahydro-pyrido[4,3-d]pyrimidine

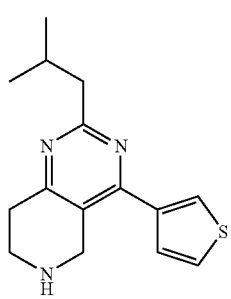

Example 34

2-Isobutyl-4-thiophen-3-yl-5,6,7,8-tetrahydro-pyrido[4,3-d]pyrimidine

MS (ESI): exact mass calcd. for $C_{15}H_{19}N_3S$, 273.13; m/z found, 274.1 [M+H]$^+$. $^1$H NMR (CDCl$_3$): 7.67 (dd, J=1.3, 2.9, 1H), 7.52 (dd, J=1.3, 5.0, 1H), 7.40 (dd, J=2.9, 5.0, 1H), 4.11 (s, 2H), 3.2 (t, J=6.1, 2H), 2.96 (t, J=6.1, 2H), 2.80 (d, J=7.3, 2H), 2.35-2.25 (m, 1H), 0.98 (d, J=6.7, 6H).

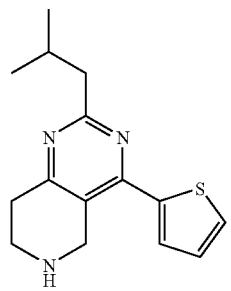

Example 35

2-Isobutyl-4-thiophen-2-yl-5,6,7,8-tetrahydro-pyrido[4,3-d]pyrimidine

MS (ESI): exact mass calcd. for $C_{15}H_{19}N_3S$, 273.13; m/z found, 274.1 [M+H]$^+$. $^1$H NMR (CDCl$_3$): 7.52 (dd, J=1.0, 5.1, 1H), 7.48 (dd, J=1.0, 3.8, 1H), 7.16 (dd, J=3.8, 5.1, 1H), 4.22, (s, 2H), 3.27 (t, J=6.0, 2H), 2.96 (t, J=6.0, 2H), 2.78 (d, J=7.3, 2H), 2.36-2.26 (m, 1H), 0.99 (d, J=6.7, 6H).

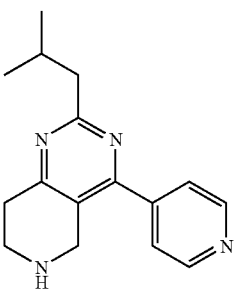

Example 36

2-Isobutyl-4-pyridin-4-yl-5,6,7,8-tetrahydro-pyrido[4,3-d]pyrimidine

MS (ESI): exact mass calcd. for $C_{16}H_{20}N_4$, 268.17; m/z found, 269.2 [M+H]$^+$. $^1$H NMR (CDCl$_3$): 8.75-8.74 (m, 2H), 7.44-7.43 (m, 2H), 3.97 (s, 2H), 3.28 (t, J=6.0, 2H), 3.01 (t, J=6.0, 2H), 2.83 (d, J=7.3, 2H), 2.34-2.23 (m, 1H), 0.98 (d, J=6.7, 6H).

Example 37

4-(4-Fluoro-phenyl)-2-isobutyl-5,6,7,8-tetrahydro-pyrido[4,3-d]pyrimidine

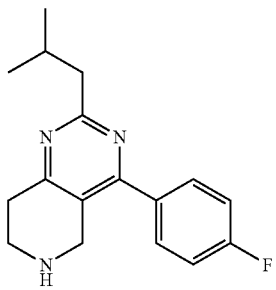

Example 38

2-Isobutyl-4-p-tolyl-5,6,7,8-tetrahydro-pyrido[4,3-d]pyrimidine

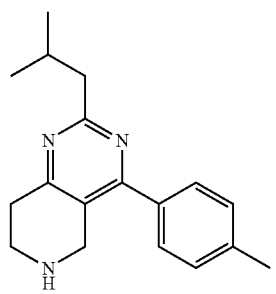

Example 39

4-(4-Fluoro-3-methyl-phenyl)-2-isobutyl-5,6,7,8-tetrahydro-pyrido[4,3-d]pyrimidine

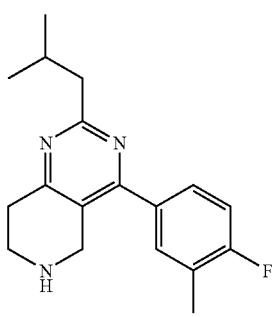

Example 40

4-(2-Isobutyl-5,6,7,8-tetrahydro-pyrido[4,3-d]pyrimidin-4-yl)-benzonitrile

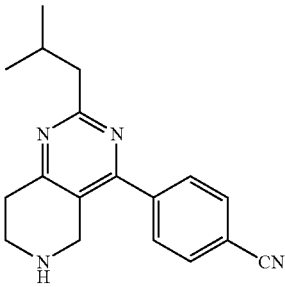

Example 41

2-Isobutyl-4-(4-methoxy-phenyl)-5,6,7,8-tetrahydro-pyrido[4,3-d]pyrimidine

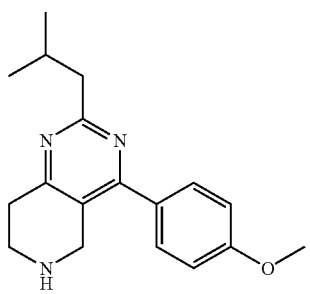

Example 42

2-sec-Butyl-4-(2-fluoro-phenyl)-5,6,7,8-tetrahydro-pyrido[4,3-d]pyrimidine hydrochloride

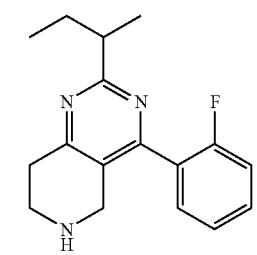

MS (ESI): exact mass calcd. for $C_{17}H_{20}FN_3$, 285.16; m/z found, 286.4 [M+H]$^+$. $^1$H NMR (DMSO-d$_6$): 9.62 (s, 2H), 7.66-7.61 (m, 1H), 7.51-7.39 (m, 3H), 4.08-4.06 (m, 2H), 3.55-3.47 (m, 2H), 3.17 (dd, J=6.3, 2H), 2.93 (tq, J=6.9, 7.4, 1H), 1.86-1.75 (m, 1H), 1.66-1.55 (m, 1H), 1.25 (d, J=6.9, 3H), 0.82 (t, J=7.4, 3H).

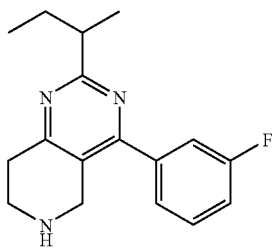

Example 43

2-sec-Butyl-4-(3-fluoro-phenyl)-5,6,7,8-tetrahydro-pyrido[4,3-d]pyrimidine

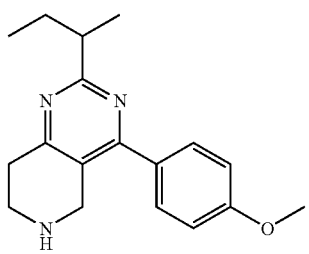

Example 44

2-sec-Butyl-4-(4-methoxy-phenyl)-5,6,7,8-tetrahydro-pyrido[4,3-d]pyrimidine

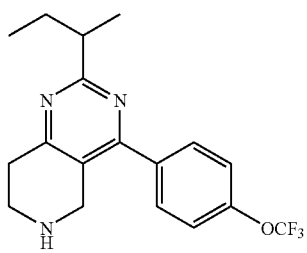

Example 45

2-sec-Butyl-4-(4-trifluoromethoxy-phenyl)-5,6,7,8-tetrahydro-pyrido[4,3-d]pyrimidine The following Examples 46-57 were prepared as described in Examples 1 and 2, substituting 5-oxo-azepane-1,4-dicarboxylic acid 1-tert-butyl ester 4-ethyl ester (J. Het. Chem. 1992, 29(4), 779-786) for 4-oxo-piperidine-1,3-dicarboxylic acid 1-tert-butyl ester 3-ethyl ester.

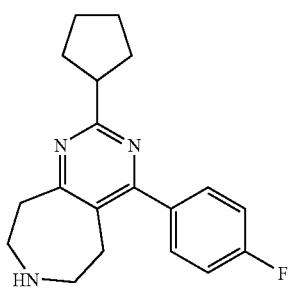

Example 46

2-Cyclopentyl-4-(4-fluoro-phenyl)-6,7,8,9-tetrahydro-5H-pyrimido[4,5-d]azepine

MS (ESI): exact mass calcd. for $C_{19}H_{22}FN_3$, 311.18; m/z found, 312.4 [M+H]$^+$. $^1$H NMR (CDCl$_3$): 7.46 (dd, J=5.4, 8.6, 2H), 7.14 (dd, J=8.7, 2H), 3.32-3.26 (m, 1H), 3.18-3.16 (m, 2H), 3.07-3.05 (m, 2H), 2.96-2.92 (m, 4H), 2.12-2.06 (m, 2H), 1.99-1.91 (m, 2H), 1.87-1.80 (m, 2H), 1.72-1.64 (m, 2H).

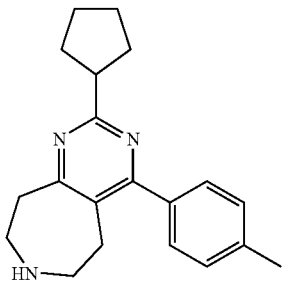

Example 47

2-Cyclopentyl-4-p-tolyl-6,7,8,9-tetrahydro-5H-pyrimido[4,5-d]azepine

MS (ESI): exact mass calcd. for $C_{20}H_{25}N_3$, 307.2; m/z found, 308.4 [M+H]$^+$. $^1$H NMR (CDCl$_3$): 7.37 (d, J=8.1, 2H), 7.26 (m, 2H), 3.32-3.26 (m, 1H), 3.17-3.15 (m, 2H), 3.07-3.05 (m, 2H), 2.94 (m, 4H), 2.41 (s, 3H), 2.11-2.05 (m, 2H), 2.0-1.93 (m, 2H), 1.86-1.79 (m, 2H), 1.71-1.62 (m, 2H).

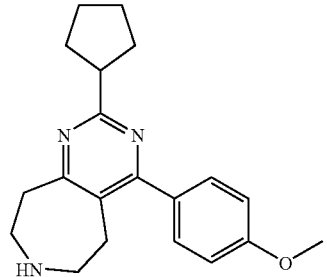

Example 48

2-Cyclopentyl-4-(4-methoxy-phenyl)-6,7,8,9-tetrahydro-5H-pyrimido[4,5-d]azepine

MS (ESI): exact mass calcd. for $C_{20}H_{25}N_3O$, 323.2; m/z found, 324.5 [M+H]$^+$. $^1$H NMR (CDCl$_3$): 7.44 (d, J=8.9, 2H), 6.98 (d, J=8.9, 2H), 3.86 (s, 3H), 3.35-3.26 (m, 1H), 3.17-3.15 (m, 2H), 3.07-3.05 (m, 2H), 2.12-2.05 (m, 2H), 2.00-1.92 (m, 2H), 1.87-1.80 (m, 2H), 1.71-1.64 (m, 2H).

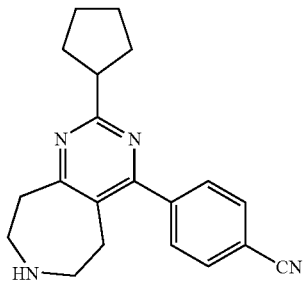

Example 49

4-(2-Cyclopentyl-6,7,8,9-tetrahydro-5H-pyrimido[4,5-d]azepin-4-yl)-benzonitrile

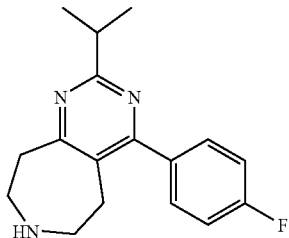

Example 50

4-(4-Fluoro-phenyl)-2-isopropyl-6,7,8,9-tetrahydro-5H-pyrimido[4,5-d]azepine hydrochloride MS (ESI): exact mass calcd. for $C_{17}H_{20}FN_3$, 285.16; m/z found, 286.2 [M+H]$^+$. $^1$H NMR (MeOH-$d_4$): 7.76-7.71 (m, 2H), 7.41-7.36 (m, 2H), 3.69-3.65 (m, 2H), 3.63-3.59 (m, 2H), 3.49-3.45 (m, 2H), 3.42-3.34 (m, 3H), 1.45 (d, J=6.9, 6H).

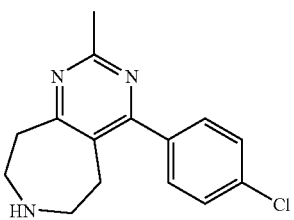

Example 51

4-(4-Chloro-phenyl)-2-methyl-6,7,8,9-tetrahydro-5H-pyrimido[4,5-d]azepine

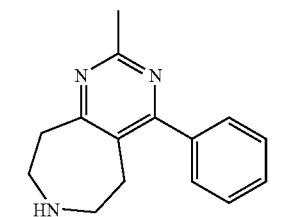

Example 52

2-Methyl-4-phenyl-6,7,8,9-tetrahydro-5H-pyrimido[4,5-d]azepine

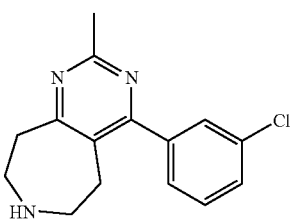

Example 53

4-(3-Chloro-phenyl)-2-methyl-6,7,8,9-tetrahydro-5H-pyrimido[4,5-d]azepine

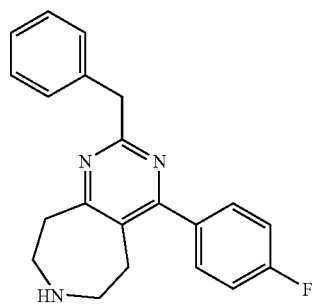

Example 54

2-Benzyl-4-(4-fluoro-phenyl)-6,7,8,9-tetrahydro-5H-pyrimido[4,5-d]azepine

MS (ESI): exact mass calcd. for $C_{21}H_{20}FN_3$, 333.16; m/z found, 334.4 [M+H]$^+$. $^1$H NMR (CDCl$_3$): 7.44-7.42 (m, 4H), 7.31-7.28 (m, 2H), 7.23-7.20 (m, 1H), 7.16-7.13 (m, 2H), 4.25 (s, 2H), 3.18-3.16 (m, 2H), 3.06-3.03 (m, 2H), 2.94-2.90 (m, 4H).

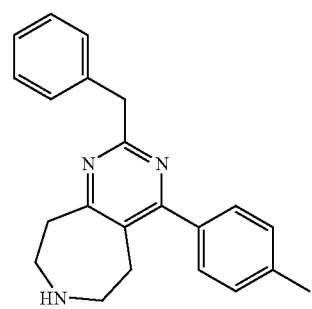

Example 55

2-Benzyl-4-p-tolyl-6,7,8,9-tetrahydro-5H-pyrimido[4,5-d]azepine

MS (ESI): exact mass calcd. for $C_{22}H_{23}N_3$, 329.19; m/z found, 330.5 [M+H]$^+$. $^1$H NMR (CDCl$_3$): 7.45-7.43 (m, 2H), 7.35-7.33 (m, 2H), 7.30-7.25 (m, 4H), 7.22-7.19 (m, 1H), 4.25 (s, 2H), 3.17-3.15 (m, 2H), 3.05-3.03 (m, 2H), 2.41 (s, 3H).

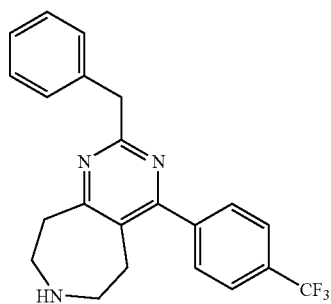

Example 56

2-Benzyl-4-(4-trifluoromethyl-phenyl)-6,7,8,9-tetrahydro-5H-pyrimido[4,5-d]azepine MS (ESI): exact mass calcd. for $C_{22}H_{20}F_3N_3$, 383.16; m/z found, 384.4 [M+H]$^+$. $^1$H NMR (CDCl$_3$): 7.72 (d, J=8.1, 2H), 7.55 (d, J=8.0, 2H), 7.43 (d, J=7.5, 2H), 7.31-7.28 (m, 2H), 7.23-7.20 (m, 1H), 4.26 (s, 2H), 3.20-3.18 (m, 2H), 3.06-3.04 (m, 2H), 2.95-2.93 (m, 2H), 2.90-2.88 (m, 2H).

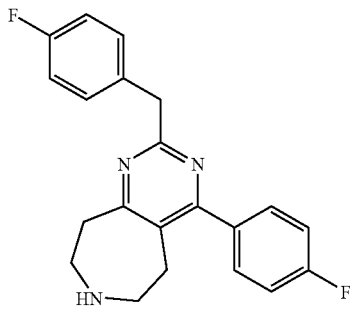

Example 57

2-(4-Fluoro-benzyl)-4-(4-fluoro-phenyl)-6,7,8,9-tetrahydro-5H-pyrimido[4,5-d]azepine MS (ESI): exact mass calcd. for $C_{21}H_{19}F_2N_3$, 351.15; m/z found, 352.4 [M+H]$^+$. $^1$H NMR (CDCl$_3$): 7.44-7.41 (m, 2H), 7.40-7.36 (m, 2H), 7.18-7.12 (m, 2H), 7.01-6.95 (m, 2H), 4.21 (s, 2H), 3.19-3.17 (m, 2H), 3.07-3.04 (m, 2H), 2.96-2.92 (m, 4H).

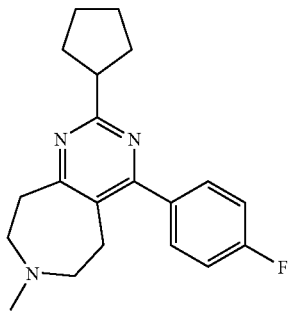

Example 58

2-Cyclopentyl-4-(4-fluoro-phenyl)-7-methyl-6,7,8,9-tetrahydro-5H-pyrimido[4,5-d]azepine To a solution of 2-cyclopentyl-4-(4-fluoro-phenyl)-6,7,8,9-tetrahydro-5H-pyrimido[4,5-d]azepine (0.035 g, 0.112 mmol) in MeOH (1 mL) was added formaldehyde (37% in water; 0.10 mL) and NaBH(OAc)$_3$ (0.032 g, 0.151 mmol). After the reaction was judged complete, the mixture was diluted with 1 N NaOH and extracted with CH$_2$Cl$_2$ (3×). The combined organic layers were dried and concentrated. The resulting residue was purified via SiO$_2$ chromatography (1-7% 2 M NH$_3$ in MeOH/CH$_2$Cl$_2$) to give 0.031 g (87%) of the title compound. MS (ESI): exact mass calcd. for $C_{20}H_{24}FN_3$, 325.20; m/z found, 326.4 [M+H]$^+$. $^1$H NMR (CDCl$_3$): 7.47 (dd, J=5.4, 8.8, 2H), 7.15 (t, J=8.7, 2H), 3.38-3.30 (m, 1H), 3.20 (dd, J=4.1, 6.3, 2H), 2.97 (dd, J=4.2, 5.9, 2H), 2.71-2.70 (m, 2H), 2.60 (m, 2H), 2.41 (s, 3H), 2.12-2.05 (m, 2H), 1.99-1.91 (m, 2H), 1.87-1.79 (m, 2H), 1.73-1.63 (m, 2H).

The following compounds in Examples 59-62 were prepared using methods similar to those described in Example 58, starting with the corresponding unmethylated azepines from the preceding examples.

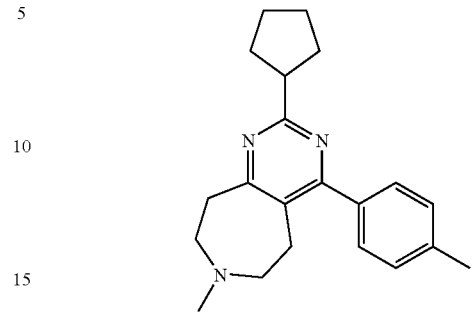

Example 59

2-Cyclopentyl-7-methyl-4-p-tolyl-6,7,8,9-tetrahydro-5H-pyrimido[4,5-d]azepine

MS (ESI): exact mass calcd. for $C_{21}H_{27}N_3$, 321.22; m/z found, 322.5 [M+H]$^+$. $^1$H NMR (CDCl$_3$): 7.39-7.37 (m, 2H), 7.27-7.25 (m, 2H), 3.35-3.26 (m, 1H), 3.20-3.18 (m, 2H), 3.0-2.97 (m, 2H), 2.7-2.68 (m, 2H), 2.59 (m, 2H), 2.41 (s, 3H), 2.40 (s, 3H), 2.12-2.04 (m, 2H), 2.0-1.91 (m, 2H), 1.88-1.79 (m, 2H), 1.72-1.61 (m, 2H).

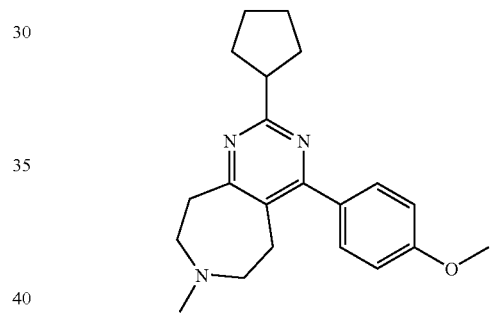

Example 60

2-Cyclopentyl-4-(4-methoxy-phenyl)-7-methyl-6,7,8,9-tetrahydro-5H-pyrimido[4,5-d]azepine MS (ESI): exact mass calcd. for $C_{21}H_{27}N_3O$, 337.22; m/z found, 338.5 [M+H]$^+$. $^1$H NMR (CDCl$_3$): 7.44 (d, J=8.8, 2H), 6.98 (d, J=8.8, 2H), 3.86 (s, 3H), 3.34-3.26 (m, 1H), 3.19 (dd, J=4.2, 6.2, 2H), 3.01 (dd, J=4.3, 5.5, 2H), 2.71-2.69 (m, 2H), 2.61 (m, 2H), 2.41 (s, 3H), 2.12-2.05 (m, 2H), 2.0-1.91 (m, 2H), 1.87-1.79 (m, 2H), 1.71-1.63 (m, 2H).

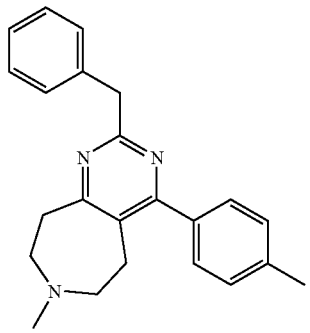

Example 61

2-Benzyl-7-methyl-4-p-tolyl-6,7,8,9-tetrahydro-5H-pyrimido[4,5-d]azepine

MS (ESI): exact mass calcd. for $C_{23}H_{25}N_3$, 343.2; m/z found, 344.5 [M+H]$^+$. $^1$H NMR (CDCl$_3$): 7.43 (d, J=7.3, 2H), 7.35 (d, J=8.0, 2H), 7.30-7.25 (m, 4H), 7.21-7.19 (m, 1H), 4.26 (s, 2H), 3.18-3.16 (m, 2H), 2.97-2.95 (m, 2H), 2.66-2.65 (m, 2H), 2.56 (m, 2H), 2.41 (s, 3H), 2.38 (s, 3H).

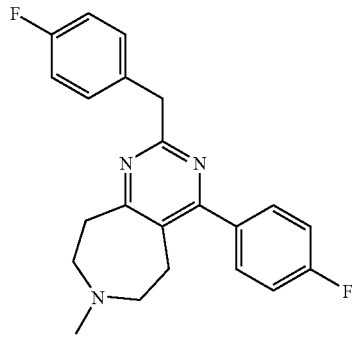

Example 62

2-(4-Fluoro-benzyl)-4-(4-fluoro-phenyl)-7-methyl-6,7,8,9-tetrahydro-5H-pyrimido[4,5-d]azepine MS (ESI): exact mass calcd. for $C_{22}H_{21}F_2N_3$, 365.17; m/z found, 366.4 [M+H]$^+$. $^1$H NMR (CDCl$_3$): 7.46-7.42 (m, 2H), 7.39-7.36 (m, 2H), 7.18-7.13 (m, 2H), 7.0-6.95 (m, 2H), 4.22 (s, 2H), 3.20-3.17 (m, 2H), 2.96-2.93 (m, 2H), 2.67-2.65 (m, 2H), 2.58-2.55 (m, 2H), 2.39 (s, 3H).

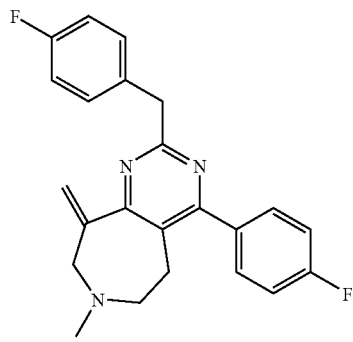

Example 63

2-(4-Fluoro-benzyl)-4-(4-fluoro-phenyl)-7-methyl-9-methylene-6,7,8,9-tetrahydro-5H-pyrimido[4,5-d]azepine To a solution of 2-(4-fluoro-benzyl)-4-(4-fluoro-phenyl)-5,6,8,9-tetrahydro-pyrimido[4,5-d]azepine-7-carboxylic acid tert-butyl ester in formic acid was added paraformaldehyde (10 equiv.). The mixture was heated at 80° C. for 6 h. The mixture was diluted with water and basified to pH ~10 with 1 M NaOH. The mixture was extracted with CH$_2$Cl$_2$, dried and concentrated. Chromatography on SiO$_2$ (0-5% 2 M NH$_3$ in MeOH/CH$_2$Cl$_2$) afforded the desired compound. 2-(4-Fluoro-benzyl)-4-(4-fluoro-phenyl)-7-methyl-6,7,8,9-tetrahydro-5H-pyrimido[4,5-d]azepine was also obtained. MS (ESI): exact mass calcd. for $C_{23}H_{21}F_2N_3$, 377.17; m/z found, 378.4 [M+H]$^+$. $^1$H NMR (CDCl$_3$): 7.50-7.46 (m, 2H), 7.42-7.37 (m, 2H), 7.17-7.12 (m, 2H), 6.99-6.94 (m, 4H), 6.03-6.01 (m, 1H), 5.47-5.46 (m, 1H), 4.25 (s, 2H), 3.51 (s, 2H), 2.87-2.83 (m, 2H), 2.76-2.72 (m, 2H), 2.41 (s, 3H).

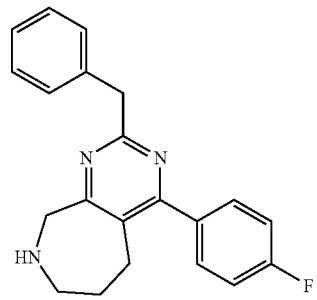

Example 64

2-Benzyl-4-(4-fluoro-phenyl)-6,7,8,9-tetrahydro-5H-pyrimido[4,5-c]azepine hydrochloride Step A. 3-Oxo-azepane-1,4-dicarboxylic acid 1-tert-butyl ester 4-ethyl ester and 4-oxo-azepane-1,3-dicarboxylic acid 1-tert-butyl ester 3-ethyl ester. To a 0° C. solution of 3-oxo-piperidine-1-carboxylic acid tert-butyl ester (11.3 g, 56.7 mmol) in Et$_2$O (170 mL) was added BF$_3$.Et$_2$O (7.2 mL, 56.7 mmol) and ethyl diazoacetate (7.2 mL, 68.0 mmol) dropwise over 30 min. After an additional 1 h, satd. aq. NaHCO$_3$ was added and the solution was stirred for 1 h, then was extracted with Et$_2$O (2×). The combined organic layers were washed with brine, dried and concentrated. The resulting residue was purified via SiO$_2$ chromatography (10-30% EtOAc/hexanes) to give 5.48 g (34%) of 3-oxo-azepane-1,4-dicarboxylic acid 1-tert-butyl ester 4-ethyl ester. In addition, 5.25 g (32%) of the more polar 4-oxo-azepane-1,3-dicarboxylic acid 1-tert-butyl ester 3-ethyl ester was isolated.

Step B. 2-Benzyl-4-(4-fluoro-phenyl)-6,7,8,9-tetrahydro-5H-pyrimido[4,5-c]azepine. The title compound was prepared from 3-oxo-azepane-1,4-dicarboxylic acid 1-tert-butyl ester 4-ethyl ester according to the methods described in Example 1. MS (ESI): exact mass calcd. for $C_{21}H_{20}FN_3$, 333.16; m/z found, 334.4 [M+H]$^+$. $^1$H NMR (DMSO-d$_6$): 9.81 (m, 2H), 7.55 (dd, J=5.5, 8.7, 2H), 7.40-7.35 (m, 4H), 7.31-7.27 (m, 2H), 7.22-7.19 (m, 1H), 4.46-4.43 (m, 2H), 4.21 (s, 2H), 3.43-3.33 (m, 2H), 3.00-2.93 (m, 2H), 1.98-1.88 (m, 2H).

The following compounds in Examples 65-68 were prepared using methods similar to those described in Example 64.

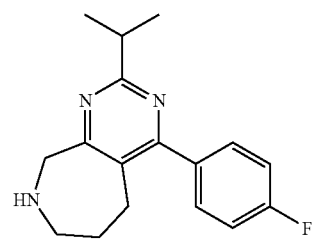

Example 65

4-(4-Fluoro-phenyl)-2-isopropyl-6,7,8,9-tetrahydro-5H-pyrimido[4,5-c]azepine hydrochloride MS (ESI): exact mass calcd. for $C_{17}H_{20}FN_3$, 285.16; m/z found, 286.4 $[M+H]^+$. $^1$H NMR (DMSO-$d_6$): 9.77 (s, 2H), 7.57 (dd, J=5.5, 8.7, 2H), 7.40-7.37 (m, 2H), 4.49-4.44 (m, 2H), 3.43-3.36 (m, 2H), 3.19-3.10 (m, 1H), 2.99-2.97 (m, 2H), 1.99-1.92 (m, 2H), 1.30 (d, J=6.9, 6H).

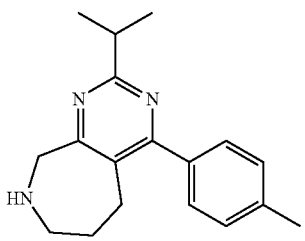

Example 66

2-Isopropyl-4-p-tolyl-6,7,8,9-tetrahydro-5H-pyrimido[4,5-c]azepine hydrochloride MS (ESI): exact mass calcd. for $C_{18}H_{23}N_3$, 281.19; m/z found, 282.4 $[M+H]^+$. $^1$H NMR (DMSO-$d_6$): 9.80 (s, 2H), 7.41 (d, J=8.0, 2H), 7.35 (d, J=8.0, 2H), 4.46 (m, 2H), 3.50-3.36 (m, 2H), 3.18-3.10 (m, 1H), 3.90-2.98 (m, 2H), 2.8 (s, 3H), 1.98-1.90 (m, 2H), 1.29 (d, J=6.9, 6H).

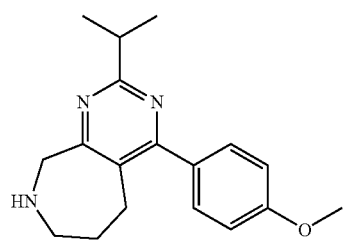

Example 67

2-Isopropyl-4-(4-methoxy-phenyl)-6,7,8,9-tetrahydro-5H-pyrimido[4,5-c]azepine

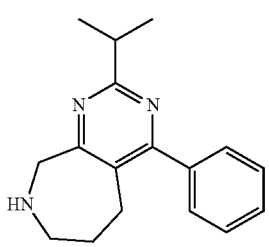

Example 68

2-Isopropyl-4-phenyl-6,7,8,9-tetrahydro-5H-pyrimido[4,5-c]azepine

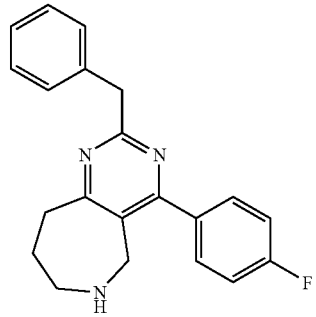

Example 69

2-Benzyl-4-(4-fluoro-phenyl)-6,7,8,9-tetrahydro-5H-1,3,6-triaza-benzocycloheptene hydrochloride The title compound was synthesized as described in Example 64 using 4-oxo-azepane-1,3-dicarboxylic acid 1-tert-butyl ester 3-ethyl ester. MS (ESI): exact mass calcd. for $C_{21}H_{20}FN_3$, 333.16; m/z found, 334.4 $[M+H]^+$. $^1$H NMR (DMSO-$d_6$): 9.59 (s, 2H), 7.66 (dd, J=5.5, 8.8, 2H), 7.42-7.27 (m, 6H), 7.22-7.19 (m, 1H), 4.29-4.26 (m, 2H), 4.21 (s, 2H), 3.42-0.36 (m, 2H), 3.22-3.20 (m, 2H), 2.01-1.95 (m, 2H).

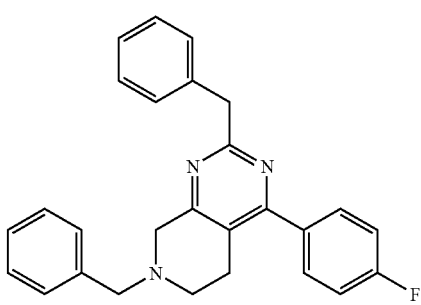

Example 70

2,7-Dibenzyl-4-(4-fluoro-phenyl)-5,6,7,8-tetrahydro-pyrido[3,4-d]pyrimidine hydrochloride The title compound was synthesized as described in Example 1, Steps A-C, using 1-benzyl-3-oxo-piperidine-4-carboxylic acid ethyl ester hydrochloride. Purification was performed using SiO$_2$ chromatography (2 M NH$_3$ in MeOH/CH$_2$Cl$_2$). MS (ESI): exact mass calcd. for $C_{27}H_{24}FN_3$, 409.2; m/z found, 410.5 $[M+H]^+$. $^1$H NMR (MeOH-$d_4$): 7.74-7.70 (m, 2H), 7.66-7.63 (m, 2H), 7.56-7.53 (m, 3H), 7.36-7.18 (m, 7H), 4.59 (s, 2H), 4.49 (br s, 2H), 4.29 (s, 2H).

The compounds in Examples 71-75 were prepared using methods similar to those described in Example 70.

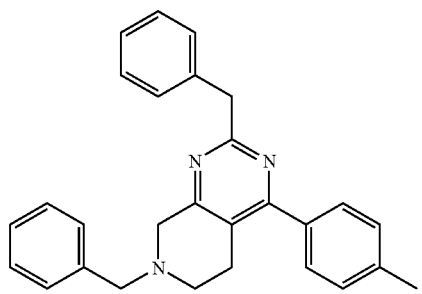

Example 71

2,7-Dibenzyl-4-p-tolyl-5,6,7,8-tetrahydro-pyrido[3,4-d]pyrimidine

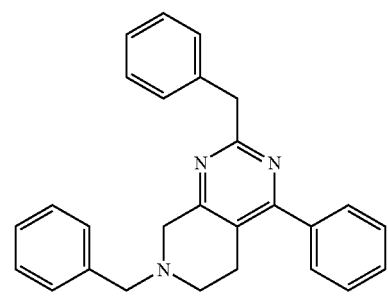

Example 72

2,7-Dibenzyl-4-phenyl-5,6,7,8-tetrahydro-pyrido[3,4-d]pyrimidine

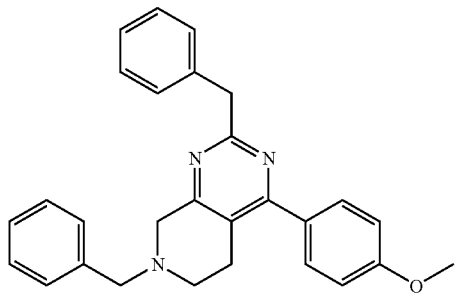

Example 73

2,7-Dibenzyl-4-(4-methoxy-phenyl)-5,6,7,8-tetrahydro-pyrido[3,4-d]pyrimidine

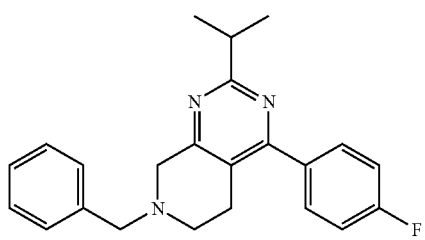

Example 74

7-Benzyl-4-(4-fluoro-phenyl)-2-isopropyl-5,6,7,8-tetrahydro-pyrido[3,4-d]pyrimidine

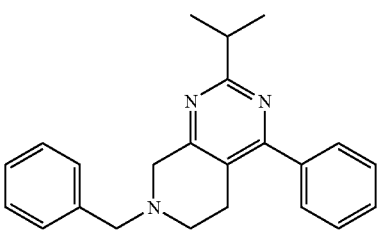

Example 75

7-Benzyl-2-isopropyl-4-phenyl-5,6,7,8-tetrahydro-pyrido[3,4-d]pyrimidine

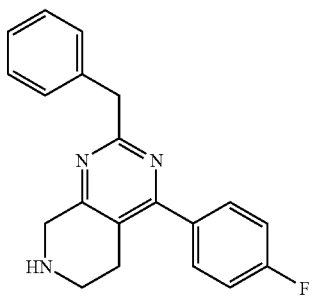

Example 76

2-Benzyl-4-(4-fluoro-phenyl)-5,6,7,8-tetrahydro-pyrido[3,4-d]pyrimidine hydrochloride To a solution of 2,7-dibenzyl-4-(4-fluoro-phenyl)-5,6,7,8-tetrahydro-pyrido[3,4-d]pyrimidine hydrochloride in EtOH was added 10% Pd/C (1 equiv) followed by 1,4-cyclohexadiene (5 equiv). The mixture was heated at 85° C. for 5 h, filtered and concentrated. The residue was dissolved in $CH_2Cl_2$ and treated with Dowex 550A resin. After 1 h, the resin was removed by filtration and the filtrate was concentrated. Chromatography on $SiO_2$ (2 M $NH_3$ in MeOH/$CH_2Cl_2$) afforded the title compound. MS (ESI): exact mass calcd. for $C_{20}H_{18}FN_3$, 319.15; m/z found, 320.4 $[M+H]^+$. $^1H$ NMR (MeOH-$d_4$): 7.70-7.67 (m, 2H), 7.36-7.35 (m, 2H), 7.31-7.25 (m, 4H), 7.20-7.17 (m, 1H), 4.42 (s, 2H), 4.26 (s, 2H), 3.48 (t, J=6.1, 2H), 3.09 (t, J=6.1, 2H).

The compounds in Examples 77-81 were prepared using methods similar to those described in Example 76.

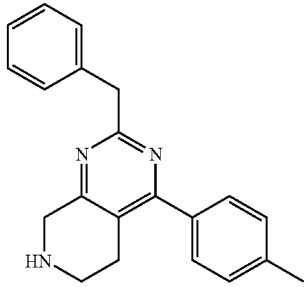

Example 77

2-Benzyl-4-p-tolyl-5,6,7,8-tetrahydro-pyrido[3,4-d]pyrimidine hydrochloride

MS (ESI): exact mass calcd. for $C_{21}H_{21}N_3$, 315.17; m/z found, 316.4 [M+H]$^+$. $^1$H NMR (MeOH-d$_4$): 7.55-7.54 (m, 2H), 7.44-7.36 (m, 4H), 7.29-7.26 (m, 2H), 7.22-7.19 (m, 1H), 4.46 (s, 2H), 4.29 (s, 2H), 3.48 (t, J=6.1, 2H), 3.12 (t, J=6.1, 2H), 2.44 (s, 3H).

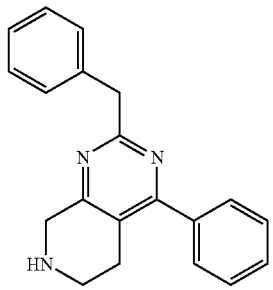

Example 78

2-Benzyl-4-phenyl-5,6,7,8-tetrahydro-pyrido[3,4-d]pyrimidine

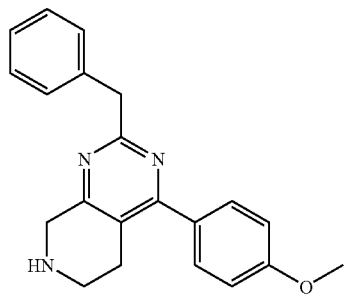

Example 79

2-Benzyl-4-(4-methoxy-phenyl)-5,6,7,8-tetrahydro-pyrido[3,4-d]pyrimidine

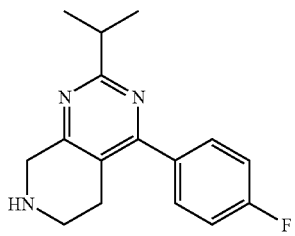

Example 80

4-(4-Fluoro-phenyl)-2-isopropyl-5,6,7,8-tetrahydro-pyrido[3,4-d]pyrimidine hydrochloride MS (ESI): exact mass calcd. for $C_{16}H_{18}FN_3$, 271.15; m/z found, 272.4 [M+H]$^+$. $^1$H NMR (MeOH-d$_4$): 7.74-7.72 (m, 2H), 7.33-7.30 (m, 2H), 4.48 (s, 2H), 3.51 (t, J=6.0, 2H), 3.26-3.20 (m, 1H), 3.12 (t, J=6.0, 2H), 1.37 (d, J=7.2, 6H).

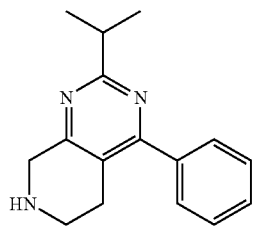

Example 81

2-Isopropyl-4-phenyl-5,6,7,8-tetrahydro-pyrido[3,4-d]pyrimidine

The compounds in Examples 82-85 were prepared using methods similar to those described in Example 58.

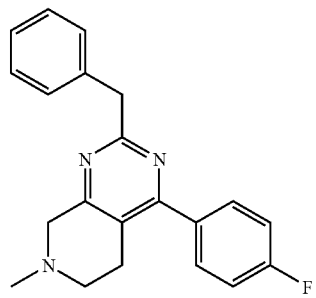

Example 82

2-Benzyl-4-(4-fluoro-phenyl)-7-methyl-5,6,7,8-tetrahydro-pyrido[3,4-d]pyrimidine hydrochloride MS (ESI): exact mass calcd. for $C_{21}H_{20}FN_3$, 333.16; m/z found, 334.4 [M+H]$^+$. $^1$H NMR (MeOH-d$_4$): 7.70-7.68 (m, 2H), 7.36-7.17 (m, 7H), 4.70-4.60 (m, 1H), 4.45-4.35 (m, 1H), 4.25 (s, 2H), 3.76 (brs, 1H), 3.11-3.01 (m, 4H).

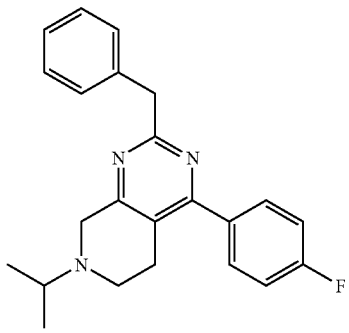

Example 83

2-Benzyl-4-(4-fluoro-phenyl)-7-isopropyl-5,6,7,8-tetrahydro-pyrido[3,4-d]pyrimidine

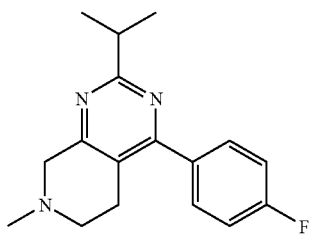

Example 84

4-(4-Fluoro-phenyl)-2-isopropyl-7-methyl-5,6,7,8-tetrahydro-pyrido[3,4-d]pyrimidine hydrochloride MS (ESI): exact mass calcd. for $C_{17}H_{20}FN_3$, 285.16; m/z found, 286.3 [M+H]$^+$. $^1$H NMR (MeOH-d$_4$): 7.74-7.71 (m, 2H), 7.32-7.29 (m, 2H), 4.72-4.62 (m, 1H), 4.49-4.37 (m, 1H), 3.79 (brs, 1H), 3.43-3.32 (m, 2H), 3.25-3.19 (m, 1H), 3.13 (s, 3H), 3.09-2.99 (m, 1H), 1.35 (d, J=6.6, 6H).

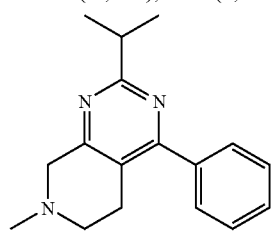

Example 85

2-Isopropyl-7-methyl-4-phenyl-5,6,7,8-tetrahydro-pyrido[3,4-d]pyrimidine

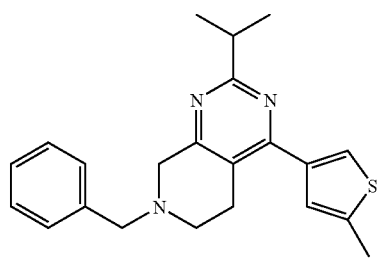

Example 86

7-Benzyl-2-isopropyl-4-(5-methyl-thiophen-3-yl)-5,6,7,8-tetrahydro-pyrido[3,4-d]pyrimidine hydrochloride Step A. 4-(7-Benzyl-2-isopropyl-5,6,7,8-tetrahydro-pyrido[3,4-d]pyrimidin-4-yl)-thiophene-2-carbaldehyde. The title compound was prepared as described in Example 1, Steps A-C.

Step B. 7-Benzyl-2-isopropyl-4-(5-methyl-thiophen-3-yl)-5,6,7,8-tetrahydro-pyrido[3,4-d]pyrimidine. To a solution of the product of Step A (0.230 g) in ethylene glycol was added hydrazine hydrate (0.1 mL). The mixture was heated at 200° C. for 1 h, then KOH (0.150 g) was added and the heating continued for 6 h. The mixture was allowed to cool then was diluted with water and extracted with Et$_2$O. The combined organic extracts were dried and concentrated to 0.210 g of pale yellow solid. Chromatography on SiO$_2$ (EtOAc/hexanes) afforded 0.146 g of the title compound. MS (ESI): exact mass calcd. for $C_{22}H_{25}N_3S$, 363.18; found m/z 364.4 [M+H]$^+$. $^1$H NMR (MeOH-d$_4$): 7.85-7.84 (m, 1H), 7.65-7.63 (m, 2H), 7.56-7.55 (m, 3H), 7.37-7.36 (m, 1H), 4.60 (br s, 2H), 4.44 (brs, 2H), 3.46-3.32 (m, 2H), 3.22-3.17 (m, 1H), 2.55 (s, 3H), 1.34 (d, J=7.2, 6H).

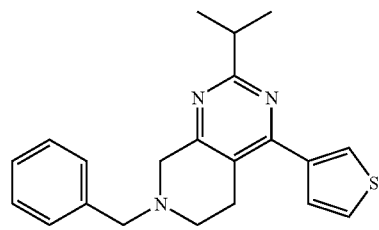

Example 87

7-Benzyl-2-isopropyl-4-thiophen-3-yl-5,6,7,8-tetrahydro-pyrido[3,4-d]pyrimidine hydrochloride The title compound was prepared according to the methods described in Example 86.

MS (ESI): exact mass calcd. for $C_{21}H_{23}N_3S$, 349.16; m/z found, 350.4 [M+H]$^+$. $^1$H NMR (MeOH-d$_4$): 8.29-8.28 (m, 1H), 7.72-7.69 (m, 4H), 7.56-7.55 (m, 3H), 4.65 (s, 2H), 4.59 (br s, 2H), 3.89 (br s, 1H), 3.57-3.32 (m, 4H), 1.40 (d, J=6.6, 6H).

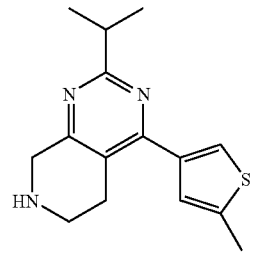

Example 88

2-Isopropyl-4-(5-methyl-thiophen-3-yl)-5,6,7,8-tetrahydro-pyrido[3,4-d]pyrimidine hydrochloride A solution of 7-benzyl-2-isopropyl-4-(5-methyl-thiophen-3-yl)-5,6,7,8-tetrahydro-pyrido[3,4-d]pyrimidine hydrochloride (0.133 g) in 1,2-dichloroethane (7 mL) was treated with 1-chloroethylchloroformate (0.105 mL). The mixture was heated at 95° C. for 16 h, concentrated, dissolved in MeOH, and heated at 50° C. for an additional 2 h. The mixture was concentrated and chromatographed on SiO$_2$ (2 M NH$_3$ in MeOH/CH$_2$Cl$_2$). MS (ESI): exact mass calcd. for C$_{15}$H$_{19}$N$_3$S, 273.13; m/z found, 274.3 [M+H]$^+$. $^1$H NMR (MeOH-d$_4$): 7.81-7.80 (m, 1H), 7.36-7.35 (m, 1H), 4.42 (s, 2H), 3.55 (t, J=6.0, 2H), 3.25 (t, J=6.0, 2H), 3.19 (m, 1H), 2.55 (s, 3H), 1.35 (d, J=7.2, 6H).

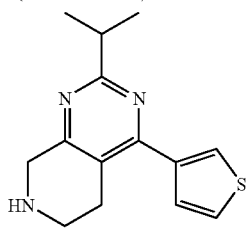

Example 89

2-Isopropyl-4-thiophen-3-yl-5,6,7,8-tetrahydro-pyrido[3,4-d]pyrimidine hydrochloride The title compound was prepared according to the methods described in Example 88.

MS (ESI): exact mass calcd. for C$_{14}$H$_{17}$N$_3$S, 259.11; m/z found, 260.3 [M+H]$^+$. $^1$H NMR (MeOH-d$_4$): 8.16-8.15 (m, 1H), 7.70-7.65 (m, 2H), 4.49 (s, 2H), 3.57 (t, J=6.0, 2H), 3.31-3.23 (m, 3H), 1.39 (d, J=7.2, 6H).

The following Examples 90-91 were prepared using methods similar to those described in Example 58.

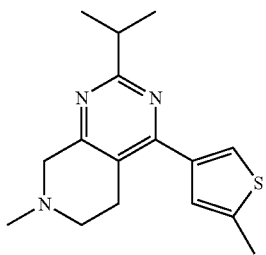

Example 90

2-Isopropyl-7-methyl-4-(5-methyl-thiophen-3-yl)-5,6,7,8-tetrahydro-pyrido[3,4-d]pyrimidine hydrochloride MS (ESI): exact mass calcd. for C$_{16}$H$_{21}$N$_3$S, 287.15; m/z found, 288.3 [M+H]$^+$. $^1$H NMR (MeOH-d$_4$): 7.79 (s, 1H), 7.36 (s, 1H), 4.65-4.54 (m, 1H), 4.45-4.35 (m, 1H), 3.83 (br s, 1H), 3.41 (brs, 1H), 3.27 (brs, 1H), 3.20-3.13 (m, 4H), 2.55 (s, 3H), 1.34 (d, J=7.2, 6H).

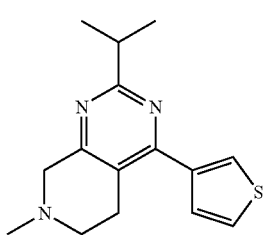

Example 91

2-Isopropyl-7-methyl-4-thiophen-3-yl-5,6,7,8-tetrahydro-pyrido[3,4-d]pyrimidine hydrochloride MS (ESI): exact mass calcd. for C$_{15}$H$_{19}$N$_3$S, 273.13; m/z found, 274.3 [M+H]$^+$. $^1$H NMR (MeOH-d$_4$): 8.27 (t, J=1.8, 1H), 7.71 (d, J=1.8, 2H), 4.82-4.71 (m, 1H), 4.63-4.49 (m, 1H), 3.95-3.81 (m, 1H), 3.57-3.41 (m, 1H), 3.34-3.32 (m, 1H), 3.16 (s, 3H), 1.41 (d, J=6.6, 6H).

The following compounds in Examples 92-99 were prepared using the methods similar to those described for Example 70 utilizing 1-benzyl-5-methyl-4-oxo-piperidine-3-carboxylic acid ethyl ester in place of 1-benzyl-3-oxo-piperidine-4-carboxylic acid ethyl ester hydrochloride.

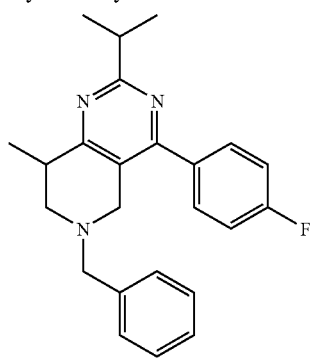

Example 92

6-Benzyl-4-(4-fluoro-phenyl)-2-isopropyl-8-methyl-5,6,7,8-tetrahydro-pyrido[4,3-d]pyrimidine

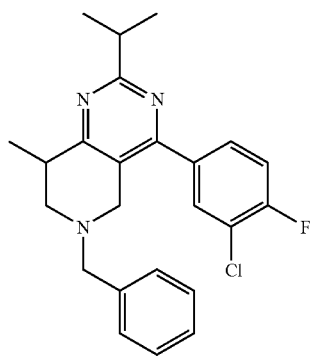

Example 93

6-Benzyl-4-(3-chloro-4-fluoro-phenyl)-2-isopropyl-8-methyl-5,6,7,8-tetrahydro-pyrido[4,3-d]pyrimidine

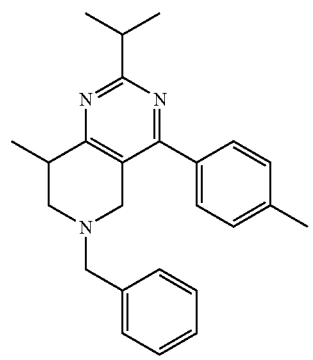

Example 94

6-Benzyl-2-isopropyl-8-methyl-4-p-tolyl-5,6,7,8-tetrahydro-pyrido[4,3-d]pyrimidine

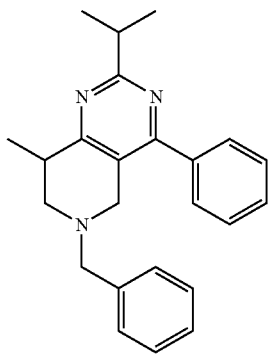

Example 95

6-Benzyl-2-isopropyl-8-methyl-4-phenyl-5,6,7,8-tetrahydro-pyrido[4,3-d]pyrimidine

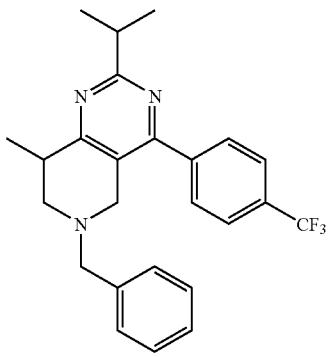

Example 96

6-Benzyl-2-isopropyl-8-methyl-4-(4-trifluoromethyl-phenyl)-5,6,7,8-tetrahydro-pyrido[4,3-d]pyrimidine

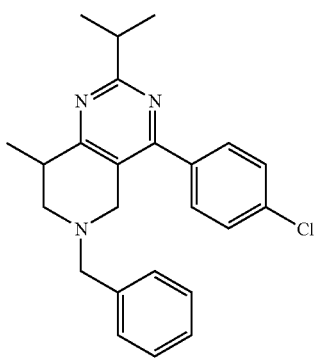

Example 97

6-Benzyl-4-(4-chloro-phenyl)-2-isopropyl-8-methyl-5,6,7,8-tetrahydro-pyrido[4,3-d]pyrimidine

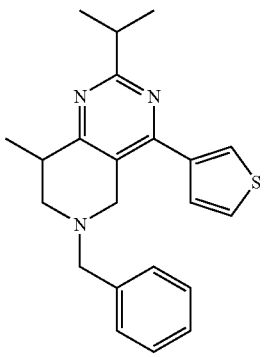

Example 98

6-Benzyl-2-isopropyl-8-methyl-4-thiophen-3-yl-5,6,7,8-tetrahydro-pyrido[4,3-d]pyrimidine

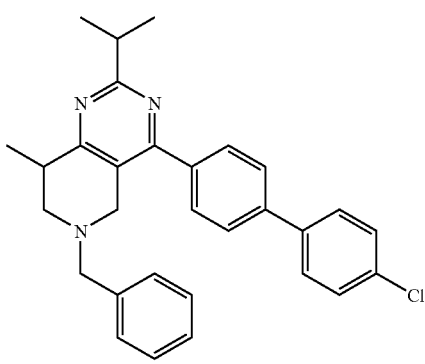

Example 99

6-Benzyl-4-(4'-chloro-biphenyl-4-yl)-2-isopropyl-8-methyl-5,6,7,8-tetrahydro-pyrido[4,3-d]pyrimidine The following compounds in Examples 100-105 were prepared using methods similar to those described in Example 76.

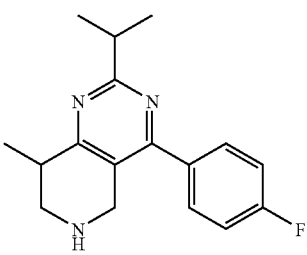

Example 100

4-(4-Fluoro-phenyl)-2-isopropyl-8-methyl-5,6,7,8-tetrahydro-pyrido[4,3-d]pyrimidine hydrochloride MS (ESI): exact mass calcd. for $C_{17}H_{20}FN_3$, 285.16; m/z found, 286.4 [M+H]$^+$. $^1$H NMR (MeOH-d$_4$): 7.69-7.66 (m, 2H), 7.34-7.30 (m, 2H), 4.56-4.53 (m, 1H), 4.32-4.29 (m, 1H), 3.81-3.78 (m, 1H), 3.45-3.38 (m, 1H), 3.36-3.30 (m, 1H), 3.26-3.24 (m, 1H), 1.55 (d, J=7.2, 3H), 1.37 (d, J=6.6, 6H).

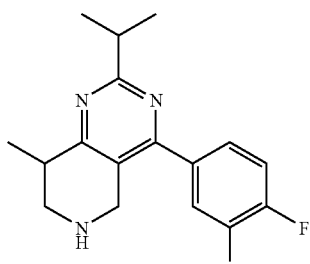

Example 101

4-(3-Chloro-4-fluoro-phenyl)-2-isopropyl-8-methyl-5,6,7,8-tetrahydro-pyrido[4,3-d]pyrimidine hydrochloride MS (ESI): exact mass calcd. for $C_{17}H_{19}ClFN_3$, 319.13; m/z found, 320.3 [M+H]$^+$. $^1$H NMR (MeOH-d$_4$): 7.79-7.77 (m, 1H), 7.60-7.58 (m, 1H), 7.46-7.44 (m, 1H), 4.56-4.54 (m, 1H), 4.32-4.29 (m, 1H), 3.80-3.77 (m, 1H), 3.40-3.32 (m, 2H), 3.26-3.20 (m, 1H), 1.54 (d, J=7.2, 3H), 1.36 (d, J=7.2, 6H).

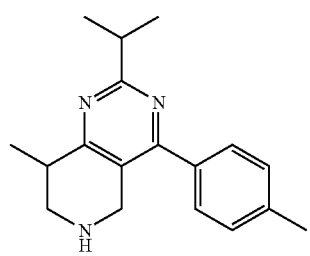

Example 102

2-Isopropyl-8-methyl-4-p-tolyl-5,6,7,8-tetrahydro-pyrido[4,3-d]pyrimidine hydrochloride MS (ESI): exact mass calcd. for $C_{18}H_{23}N_3$, 281.19; m/z found, 282.4 [M+H]$^+$. $^1$H NMR (MeOH-d4): 7.57-7.56 (m, 2H), 7.45-7.44 (m, 2H), 4.59-4.56 (m, 1H), 4.35-4.33 (m, 1H), 3.83-3.80 (m, 1H), 3.52-3.49 (m, 1H), 3.40-3.30 (m, 2H), 2.46 (s, 3H), 1.58 (d, J=7.2, 3H), 1.41 (d, J=6.6, 6H).

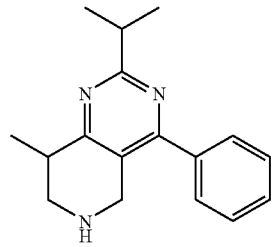

Example 103

2-Isopropyl-8-methyl-4-phenyl-5,6,7,8-tetrahydro-pyrido[4,3-d]pyrimidine

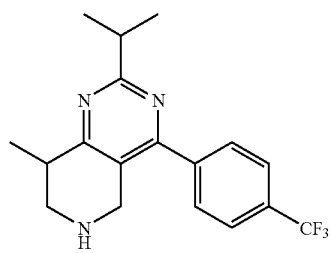

Example 104

2-Isopropyl-8-methyl-4-(4-trifluoromethyl-phenyl)-5,6,7,8-tetrahydro-pyrido[4,3-d]pyrimidine

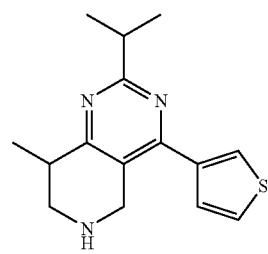

Example 105

2-Isopropyl-8-methyl-4-thiophen-3-yl-5,6,7,8-tetrahydro-pyrido[4,3-d]pyrimidine

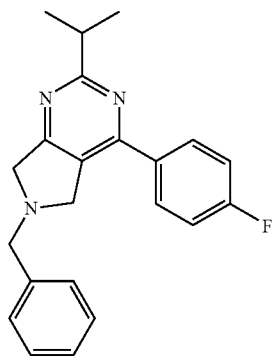

Example 106

4-(4-Fluoro-phenyl)-2-isopropyl-6,7-dihydro-5H-pyrrolo[3,4-d]pyrimidine hydrochloride Step A. 6-Benzyl-2-isopropyl-6,7-dihydro-5H-pyrrolo[3,4-d]pyrimidin-4-ol. To a solution of 1-benzyl-4-oxo-pyrrolidine-3-carboxylic acid ethyl ester hydrochloride (U.S. Pat. No. 3,312,716; 0.568 g, 2.30 mmol) in tert-BuOH was added isobutyramidine hydrochloride (0.282 g, 2.30 mmol) and KOtBu (0.516 g, 4.6 mmol). After heating for 6 h at 100° C., the reaction was cooled to rt, concentrated, diluted with water and washed with Et$_2$O. The organic layer discarded. The aqueous layer was adjusted to pH 7 and extracted with Et$_2$O. The organic layers were then dried and concentrated to give 0.145 g (23%) of the title compound of yellow solid that was used without further purification.

Steps B and C. The title compound was prepared according to the methods described in Example 1, Steps B and C. MS (ESI): exact mass calcd. for $C_{22}H_{22}FN_3$, 347.18; m/z found, 348.3 [M+H]$^+$. $^1$H NMR (MeOH-d$_4$): 7.99-7.96 (m, 2H), 7.61-7.60 (m, 2H), 7.53-7.51 (m, 3H), 7.34-7.32 (m, 2H), 5.09 (br s, 2H), 4.71 (br s, 4H), 3.31-3.25 (m, 1H), 1.38 (d, J=7.2, 6H).

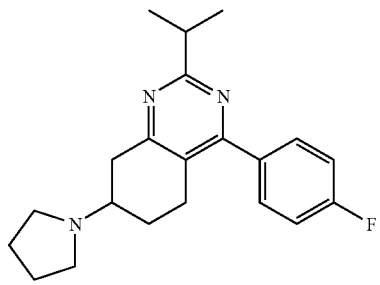

Example 107

4-(4-Fluoro-phenyl)-2-isopropyl-7-pyrrolidin-1-yl-5,6,7,8-tetrahydro-quinazoline Step A. 4-Ethoxy-2-oxo-cyclohex-3-enecarboxylic acid ethyl ester. To a −78° C. solution of LDA (192 mmol) in THF (200 mL) was added 3-ethoxy-cyclohex-2-enone (23 mL) dropwise. After stirring for 1 h at −78° C., ethyl cyanoformate (16 mL) was added. The mixture was stirred at −78° C. for 4 h and then was warmed to rt and stirred for 1 h. The mixture was concentrated, diluted with aq. NH$_4$Cl (300 mL), and poured into water. The resulting solids were collected by suction filtration and washed with hexanes followed by water, then was dried and concentrated to provide 17.1 g of a brown solid. TLC (SiO$_2$, 33% EtOAc/hexanes): R$_f$=0.43.

Step B. 7-Oxo-1,4-dioxa-spiro[4.5]decane-8-carboxylic acid ethyl ester. To a solution of the product of Step A (25.4 g resulting from iterative reactions) in toluene (500 mL) was added ethylene glycol (8.5 mL) and p-TsOH (1.9 g). The mixture was heated at reflux for 4 h in a flask fitted with a Dean-Stark trap. The mixture was then cooled and concentrated. Chromatography on SiO$_2$ (0 to 15% EtOAc/hexanes) afforded 7.76 g of the desired compound. TLC (SiO$_2$, 25% EtOAc/hexanes): R$_f$=0.42.

Step C. 2-Isopropyl-7-(2-[1,3]dioxolane)-5,6,7,8-tetrahydro-quinazolin-4-ol. The title compound was prepared according to the method described in Example 1, Step A. MS (ESI): exact mass calcd. for $C_{13}H_{18}N_2O_3$, 250.13; m/z found, 251.3 [M+H]$^+$.

Step D. Trifluoro-methanesulfonic acid 2-isopropyl-7-(2-[1,3]Dioxolane)-5,6,7,8-tetrahydro-quinazolin-4-yl ester. The title compound was prepared according to the method described in Example 1, Step B. TLC (SiO$_2$, 25% EtOAc/hexanes): R$_f$=0.46. MS (ESI): exact mass calcd. for $C_{14}H_{17}F_3N_2O_5S$, 382.08; m/z found, 383.2 [M+H]$^+$.

Step E. 4-(4-Fluoro-phenyl)-2-isopropyl-7-(2-[1,3]dioxolane)-5,6,7,8-tetrahydro-quinazoline. The title compound was prepared according to the method described in Example 1, Step C. TLC (SiO$_2$, 25% EtOAc/hexanes): R$_f$=0.40. MS (ESI): exact mass calcd. for $C_{19}H_{21}FN_2O_2$, 328.16; m/z found, 329.3 [M+H]$^+$.

Step F. 4-(4-Fluoro-phenyl)-2-isopropyl-5,8-dihydro-6H-quinazolin-7-one. To a solution of the product of Step E (1.15 g) in THF (70 mL) was added 1 M HCl (6 mL). The mixture was heated at 60° C. for 10 h, cooled to rt, and poured into 350 mL of water. The aqueous mixture was basified to pH ~9 with 1 M NaOH, and was extracted with CH$_2$Cl$_2$. The organic layer was dried and concentrated to afford 0.98 g of the desired compound, which was used in the next step without purification. MS (ESI): exact mass calcd. for $C_{17}H_{17}FN_2O$, 284.13; m/z found, 285.3 [M+H]$^+$.

Step G. 4-(4-Fluoro-phenyl)-2-isopropyl-7-pyrrolidin-1-yl-5,6,7,8-tetrahydro-quinazoline. To a solution of the product of Step F (0.128 g) in MeOH (4 mL) was added of bromocresol green (0.003 g), pyrrolidine (0.06 mL), and NaBH$_3$CN (0.20 g). To this mixture was added 1 M HCl in MeOH until a persistent color change to yellow was observed. After 30 min, the mixture was quenched with 1 M NaOH and poured into water (50 mL). The mixture was extracted with CH$_2$Cl$_2$, dried and concentrated. Chromatography on SiO$_2$ (0 to 5% 2 M NH$_3$ in MeOH/CH$_2$Cl$_2$) afforded 0.015 g of the desired compound. MS (ESI): exact mass calcd. for $C_{21}H_{26}FN_3$, 339.21; m/z found, 340.4 [M+H]$^+$. $^1$H NMR (CDCl$_3$): 7.59-7.54 (m, 2H), 7.18-7.13 (m, 2H), 3.76-3.68 (m, 1H), 3.50-3.44 (m, 1H), 3.41-3.35 (m, 1H), 3.28-3.14 (m, 2H), 3.0-2.93 (m, 1H), 2.88-2.70 (m, 4H), 2.36-2.23 (m, 3H), 2.19-2.09 (m, 1H), 1.98-1.87 (m, 2H).

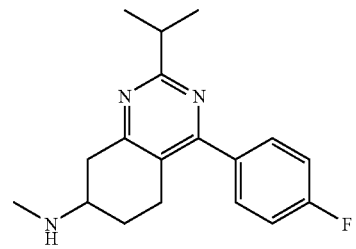

Example 108

[4-(4-Fluoro-phenyl)-2-isopropyl-5,6,7,8-tetrahydro-quinazolin-7-yl]-methyl-amine hydrochloride The title compound was prepared according to the method described for Example 107.

MS (ESI): exact mass calcd. for $C_{18}H_{22}FN_3$, 299.18; m/z found, 300.4 [M+H]$^+$. $^1$H NMR (MeOH-d$_4$): 7.80-7.72 (m, 2H), 7.37-7.30 (m, 2H), 3.81-3.71 (m, 1H), 3.65-3.56 (m, 1H), 3.35-3.26 (m, 1H), 3.22-3.14 (m, 1H), 3.11-3.00 (m, 1H), 2.99-2.91 (m, 1H), 2.85 (s, 3H), 2.42-2.33 (m, 1H), 1.92-1.82 (m, 1H), 1.43-1.38 (m, 6H).

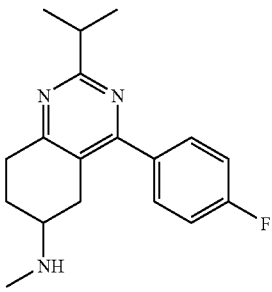

Example 109

[4-(4-Fluoro-phenyl)-2-isopropyl-5,6,7,8-tetrahydro-quinazolin-6-yl]-methyl-amine hydrochloride The title compound was prepared according to the methods described for Example 107, using 1,4-dioxa-spiro[4.5]decan-8-one. MS (ESI): exact mass calcd. for $C_{18}H_{22}FN_3$, 299.18; m/z found, 300.4 [M+H]$^+$. $^1$H NMR (MeOH-d$_4$): 7.87-7.82 (m, 2H), 7.40-7.35 (m, 2H), 3.59-3.52 (m, 1H), 3.41-3.24 (m, 4H), 3.20-3.13 (m, 1H), 2.76 (s, 3H), 2.54-2.47 (m, 1H), 2.21-2.11 (m, 1H), 1.45 (d, J=6.9, 3H), 1.44 (d, J=6.9, 3H).

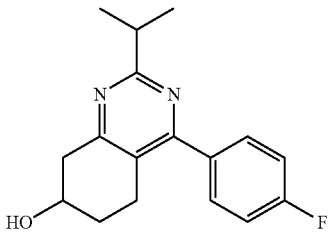

Example 110

4-(4-Fluoro-phenyl)-2-isopropyl-5,6,7,8-tetrahydro-quinazolin-7-ol

To a solution of 4-(4-fluoro-phenyl)-2-isopropyl-5,8-dihydro-6H-quinazolin-7-one (0.126 g) in EtOH (3 mL) was added NaBH$_4$ (0.053 g). After 16 h, the mixture was treated with 1 M NaOH (5 mL) and water (10 mL). The mixture was stirred for 30 min then extracted with CH$_2$Cl$_2$. The organic layer was dried and concentrated. Chromatography on SiO$_2$ (10 to 35% EtOAc/hexanes) afforded 0.98 g of the title compound. TLC (SiO$_2$, 50% EtOAc/hexanes): R$_f$=0.18. MS (ESI): exact mass calcd. for C$_{17}$H$_{19}$FN$_2$O, 286.15; m/z found, 287.3 [M+H]$^+$.

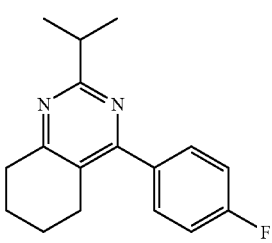

Example 111

4-(4-Fluoro-phenyl)-2-isopropyl-5,6,7,8-tetrahydro-quinazoline

The title compound was obtained as a minor product from the hydrogenation of of 4-(4-fluoro-phenyl)-2-isopropyl-5,8-dihydro-6H-quinazolin-7-one with 10% Pd/C in the presence of pyrrolidine. MS (ESI): exact mass calcd. for $C_{17}H_{19}FN_2$, 270.15; m/z found, 271.3 [M+H]$^+$. $^1$H NMR (CDCl$_3$): 7.59-7.55 (m, 2H), 7.16-7.12 (m, 2H), 3.21-3.13 (m, 1H), 2.95-2.91 (m, 2H), 2.71-2.67 (m, 2H), 1.95-1.89 (m, 2H), 1.77-1.72 (m, 2H), 1.35 (d, J=6.9, 6H).

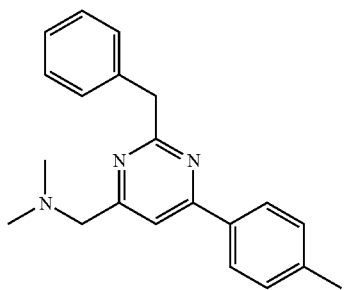

Example 112

(2-Benzyl-6-p-tolyl-pyrimidin-4-ylmethyl)-dimethyl-amine

Step A. 2-Benzyl-4-(tetrahydro-pyran-2-yloxymethyl)-6-p-tolyl-pyrimidine. To a solution of Pd(PPh$_3$)$_2$Cl$_2$ (0.285 g, 0.41 mmol) and CuI in THF (50 mL) (0.148 g, 0.777 mmol) was added Et$_3$N (1.5 mL, 11.0 mmol), p-toluoyl chloride (1.3 mL, 10.0 mmol) and tetrahydro-2-(2-propynyloxy)-2H-pyran (1.4 mL, 10.0 mmol). After stirring for 2.5 h, a solution of 2-phenylacetamidine hydrochloride (2.0 g, 11.7 mmol) in THF/MeOH (1:1, 10 mL) was added followed by additional MeOH (5 mL) and Na$_2$CO$_3$ (3.2 g, 30.0 mmol). The reaction mixture was heated at reflux for 15 h, cooled to rt, diluted with Et$_2$O and filtered through a small pad of diatomaceous earth. The filtrate was concentrated and purified via SiO$_2$ chromatography (10-45% EtOAc/hexanes) to give 2.0 g (53%) of the title compound. $^1$H NMR (CDCl$_3$): 8.02-8.00 (m, 2H), 7.68 (s, 1H), 7.46-7.44 (m, 2H), 7.30-7.27 (m, 4H), 7.21-7.19 (m, 1H), 4.87 (d, J=14.7, 1H), 4.77 (t, J=3.5, 1H), 4.62 (d, J=15.1, 1H), 4.31 (s, 2H), 3.91-3.86 (m, 1H), 3.57-3.52 (m, 1H), 2.41 (s, 3H), 1.96-1.87 (m, 1H), 1.84-1.72 (m, 2H), 1.66-1.55 (m, 3H).

Step B. (2-Benzyl-6-p-tolyl-pyrimidin-4-yl)-methanol. To a solution of the product from Step A (2.0 g, 5.3 g) in MeOH (30 mL) was added p-TsOH.H$_2$O. After 18 h, the reaction was diluted with satd. aq. NaHCO$_3$ and extracted with EtOAc (2×). The combined organic layers were dried and concentrated to give the 1.53 g (99%) of the title compound. MS (ESI): exact mass calcd. for C$_{19}$H$_{18}$N$_2$O, 290.14; m/z found, 291.4 [M+H]$^+$. $^1$H NMR (CDCl$_3$): 8.00-7.98 (m, 2H), 7.45-7.43 (m, 3H), 7.32-7.28 (m, 4H), 7.23-7.20 (m, 1H), 4.74 (d, J=4.8, 2H), 4.33 (s, 2H), 3.62 (t, J=5.1, 1H), 2.42 (s, 3H).

Step C. (2-Benzyl-6-p-tolyl-pyrimidin-4-ylmethyl)-dimethyl-amine. To a solution of the product from Step B (0.102 g, 0.35 mmol) in CH$_2$Cl$_2$ (2 mL) was added the Dess-Martin periodinane (0.228, 0.53 mmol). After 30 min, the mixture was diluted satd. aq. NaHCO$_3$ and extracted with CH$_2$Cl$_2$ (2×). The combined organic layers were dried, concentrated, and filtered through a small plug of SiO$_2$ (25% EtOAc in hexanes). The filtrate was concentrated to give 2-benzyl-6-p-tolyl-pyrimidine-4-carbaldehyde (0.55 g, 54%). To a solution of this aldehyde in CH$_2$Cl$_2$ (3 mL) was added dimethylamine (2 M in THF; 0.15 mL, 0.30 mmol) and NaBH(OAc)$_3$ (0.058 mg, 0.27 mmol). After 15 h, the reaction was diluted with CH$_2$Cl$_2$ and washed with 1 N NaOH. The aqueous layer was extracted with CH$_2$Cl$_2$ (1×). The combined organic layers were dried and concentrated. The resulting residue was purified via SiO$_2$ chromatography (1-7% 2 M NH$_3$ in MeOH/CH$_2$Cl$_2$) to give 0.050 g (79%) of the title compound. MS (ESI): exact mass calcd. for C$_{21}$H$_{23}$N$_3$, 317.19; m/z found, 318.4 [M+H]$^+$. $^1$H NMR (CDCl$_3$): 8.02 (d, J=8.2, 2H), 7.66 (s, 1H), 7.22 (d, J=7.5, 2H), 7.31-7.26 (m, 4H), 7.22-7.18 (m, 1H), 4.33 (s, 2H), 3.58 (s, 2H), 2.41 (s, 3H), 2.32 (s, 6H).

The compounds in Examples 113-114 were prepared using methods similar to those described in Example 112, with the appropriate substituent changes.

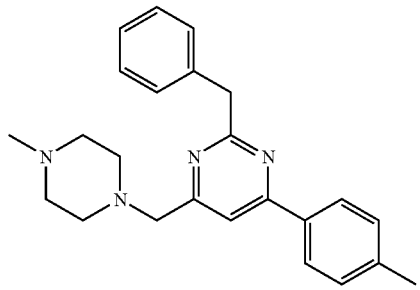

Example 113

2-Benzyl-4-(4-methyl-piperazin-1-ylmethyl)-6-p-tolyl-pyrimidine

MS (ESI): exact mass calcd. for C$_{24}$H$_{28}$N$_4$, 372.23; m/z found, 373.5 [M+H]$^+$. $^1$H NMR (CDCl$_3$): 8.02-7.99 (m, 2H), 7.66 (s, 1H), 7.46-7.44 (m, 2H), 7.31-7.27 (m, 4H), 7.22-7.18 (m, 1H), 4.32 (s, 2H), 3.66 (s, 2H), 2.58-2.50 (m, 8H), 2.42 (s, 3H), 2.32 (s, 3H).

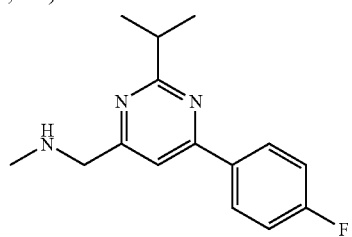

Example 114

[6-(4-Fluoro-phenyl)-2-isopropyl-pyrimidin-4-ylmethyl]-methyl-amine

Prop-2-ynyl-carbamic acid tert-butyl ester was converted to [6-(4-fluoro-phenyl)-2-isopropyl-pyrimidin-4-ylmethyl]-methyl-carbamic acid tert-butyl ester using methods described in Example 112, Step A. This ester was deprotected according to the methods described in Example 1, Step D, to provide the title compound. MS (ESI): exact mass calcd. for C$_{15}$H$_{18}$FN$_3$, 259.15; m/z found, 260.3 [M+H]$^+$. $^1$H NMR (DMSO-d$_6$): 9.45 (s, 2H); 8.31-8.28 (m, 2H), 8.10 (s, 1H), 7.45-7.41 (m, 2H), 4.35 (t, J=6.0, 2H), 3.26-3.18 (m, 1H), 2.69 (t, J=5.4, 3H), 1.37 (d, J=6.9, 6H).

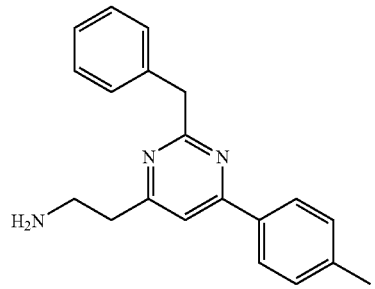

Example 115

2-(2-Benzyl-6-p-tolyl-pyrimidin-4-yl)-ethylamine

Step A and B. 2-(2-Benzyl-6-p-tolyl-pyrimidin-4-yl)-ethanol. The title compound was prepared from 2-(3-butynyloxy) tetrahydro-2H-pyran using the methods described in Example 112, Steps A and B. MS (ESI): exact mass calcd. for C$_{20}$H$_{20}$N$_2$O, 304.16; m/z found, 305.4 [M+H]$^+$. $^1$H NMR (CDCl$_3$): 7.98 (d, J=8.2, 2H), 7.42-7.42 (m, 2H), 7.34-7.29 (m, 4H), 7.25-7.22 (m, 1H), 4.31 (s, 2H), 3.98 (t, J=5.3, 2H), 2.97 (t, J=5.3, 2H), 2.42 (s, 3H).

Step C. 4-(2-Azido-ethyl)-2-benzyl-6-p-tolyl-pyrimidine. To a 0° C. solution of the product of Step B (0.150 g, 0.493 mmol) in THF (2.5 mL) was added MsCl (0.042 mL, 0.54 mmol) followed by Et$_3$N (0.76 mL, 0.54 mmol). After 1 h, EtOAc was added and the mixture washed with brine, dried and concentrated to give methanesulfonic acid 2-(2-benzyl-6-p-tolyl-pyrimidin-4-yl)-ethyl ester (0.185 g). To a solution of this mesylate (0.120 g, 0.32 mmol) in DMF (1 mL) was added sodium azide (0.105 g, 1.6 mmol). The flask was heated at 40° C. for 10 h, then was cooled to rt, diluted with water, and extracted with EtOAc (3×). The combined organic layers were dried and concentrated. The resulting residue was purified via SiO$_2$ chromatography (5-15% EtOAc/hexanes) to give 0.080 g (76%) of the title compound. MS (ESI): exact mass calcd. for C$_{20}$H$_{19}$N$_5$, 329.16 m/z found, 330.4 [M+H]$^+$. $^1$H NMR (CDCl$_3$): 7.98 (d, J=8.2, 2H), 7.46-7.43 (m, 2H), 7.38 (s, 1H), 7.32-7.28 (m, 4H), 7.23-7.19 (m, 2H), 4.31 (s, 2H), 3.76 (t, J=6.8, 2H), 3.02 (t, J=6.8, 2H), 2.42 (s, 3H).

Step D. To a solution of the product of Step C (0.066 g, 0.2 mmol) in THF (2 mL) was added PPh$_3$ (0.059 g, 2.2 mmol). After 18 h, water was added (0.10 mL) and the mixture was stirred for 48 h. The mixture was diluted with water and extracted with CH$_2$Cl$_2$ (2×). The combined organic layers were dried and concentrated. The resulting residue was purified via SiO$_2$ chromatography (5-15% EtOAc/hexanes) to give 0.060 g (99%) of the title compound. MS (ESI): exact mass calcd. for C$_{20}$H$_{21}$N$_3$, 303.17; m/z found, 304.4 [M+H]$^+$. $^1$H NMR (CDCl$_3$): 7.98-7.96 (m, 2H), 7.45-7.44 (m, 2H), 7.36 (s, 1H), 7.32-7.28 (m, 4H), 7.23-7.19 (m, 1H), 4.31 (s, 2H), 3.13 (t, J=6.5, 2H), 2.91 (t, J=6.5, 2H), 2.42 (s, 3H).

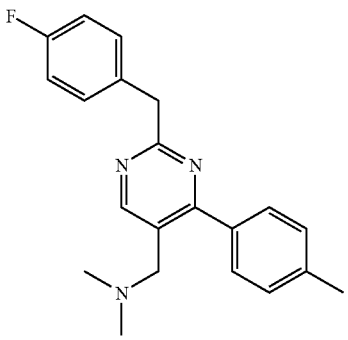

Example 116

[2-(4-Fluoro-benzyl)-4-p-tolyl-pyrimidin-5-ylmethyl]-dimethyl-amine

Step A. 2-(4-Fluoro-benzyl)-4-p-tolyl-pyrimidine-5-carboxylic acid ethyl ester. To solution of 3-dimethylamino-2-(4-methyl-benzoyl)-acrylic acid ethyl ester (Tetrahedron, 2002, 58, 8581-8589; 0.567 g, 2.15 mmol) in EtOH (10 mL) was added 2-(4-fluoro-phenyl)-acetamidine hydrochloride (0.405 g, 2.15 mmol) and Et$_3$N (0.90 mL, 6.5 mmol). The mixture was heated at reflux for 18 h, and then was diluted with water and extracted with EtOAc (2×). The combined organic layers were dried and concentrated. The resulting residue was purified via SiO$_2$ chromatography (5-20% EtOAc/hexanes) to give 0.560 g (74%) of the title compound. MS (ESI): exact mass calcd. for C$_{21}$H$_{19}$FN$_2$O$_2$, 350.14; m/z found, 351.4 [M+H]$^+$. $^1$H NMR (CDCl$_3$): 8.97 (s, 1H), 7.51 (d, J=8.2, 2H), 7.38-7.35 (m, 2H), 7.27-7.26 (m, 2H), 7.01-6.97 (m, 2H), 4.32 (s, 2H), 4.23 (q, J=7.1, 2H), 2.42 (s, 3H), 1.16 (t, J=7.1, 3H).

Step B. [2-(4-Fluoro-benzyl)-4-p-tolyl-pyrimidin-5-yl]-methanol. To a 0° C. solution of the product from Step A (0.606 g, 1.73 mmol) in THF (8 mL) was added DIBAL-H (1.5 M in toluene; 2.5 mL, 3.8 mmol). The mixture was allowed to warm to rt, and was stirred for 18 h. The mixture was diluted with 20% aq. sodium potassium tartrate and extracted with EtOAc (2×). The combined organic layers were dried and concentrated. The resulting residue was purified via SiO$_2$ chromatography (40-60% EtOAc/hexanes) to give 0.330 g (62%) of the title compound. MS (ESI): exact mass calcd. for C$_{19}$H$_{17}$FN$_2$O, 308.13; m/z found, 309.4 [M+H]$^+$. $^1$H NMR (CDCl$_3$): 8.77 (s, 1H), 7.58 (d, J=8.0, 2H), 7.38-7.35 (m, 2H), 7.29 (d, J=7.9, 2H), 6.99-6.96 (m, 2H), 4.70 (s, 2H), 4.29 (s, 2H), 2.42 (s, 3H).

Step C. The title compound was prepared using the methods described in Example 112, Step C. MS (ESI): exact mass calcd. for C$_{21}$H$_{22}$FN$_3$, 335.18; m/z found, 336.4 [M+H]$^+$. $^1$H NMR (CDCl$_3$): 8.67 (s, 1H), 7.69 (d, J=8.1, 2H), 7.40-7.36 (m, 2H), 7.29 (d, J=7.9, 2H), 7.01-6.96 (m, 2H), 4.29 (s, 2H), 3.36 (s, 2H), 2.42 (s, 3H), 2.22 (s, 6H).

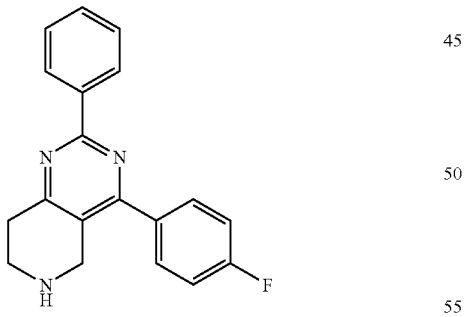

Example 117

4-(4-Fluoro-phenyl)-2-phenyl-5,6,7,8-tetrahydro-pyrido[4,3-d]pyrimidine

The title compound was prepared as described in the preceding examples. MS (ESI): exact mass calcd. for C$_{19}$H$_{16}$FN$_3$, 305.35; m/z found, 306.4 [M+H]$^+$. $^1$H NMR (CDCl$_3$): 8.48-8.46 (m, 2H), 7.66 (dd, J=5.4, 8.7, 2H), 7.49-7.45 (m, 3H), 7.21-7.17, (m, J=8.7, 2H), 4.06 (s, 2H), 3.31 (t, J=6.1, 2H), 3.08 (t, J=6.1, 2H).

The following Examples 118-163 may be prepared according to the methods described in the preceding examples.

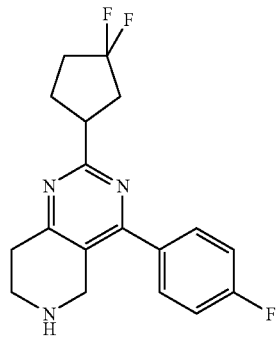

Example 118

2-(3,3-Difluoro-cyclopentyl)-4-(4-fluoro-phenyl)-5,6,7,8-tetrahydro-pyrido[4,3-d]pyrimidine

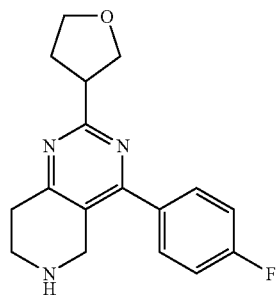

Example 119

4-(4-Fluoro-phenyl)-2-(tetrahydro-furan-3-yl)-5,6,7,8-tetrahydro-pyrido[4,3-d]pyrimidine

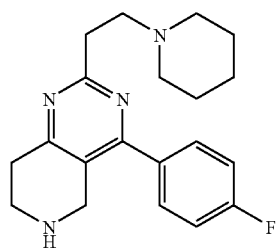

Example 120

4-(4-Fluoro-phenyl)-2-(2-piperidin-1-yl-ethyl)-5,6,7,8-tetrahydro-pyrido[4,3-d]pyrimidine

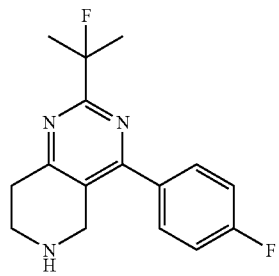

Example 121

2-(1-Fluoro-1-methyl-ethyl)-4-(4-fluoro-phenyl)-5,6,7,8-tetrahydro-pyrido[4,3-d]pyrimidine

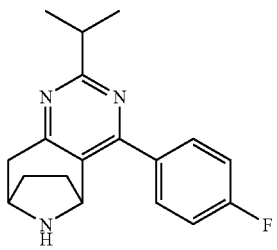

Example 122

3-(4-Fluoro-phenyl)-5-isopropyl-4,6,12-triaza-tricyclo[7.2.1.0$^{2,7}$]dodeca-2,4,6-triene

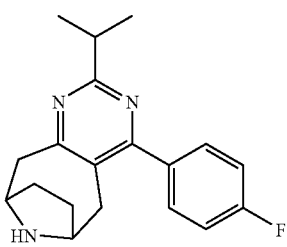

Example 123

7-(4-Fluoro-phenyl)-5-isopropyl-4,6,13-triaza-tricyclo[8.2.1.0$^{3,8}$]trideca-3,5,7-triene

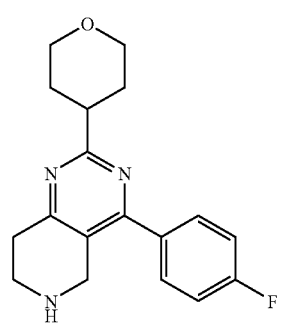

Example 124

4-(4-Fluoro-phenyl)-2-(tetrahydro-pyran-4-yl)-5,6,7,8-tetrahydro-pyrido[4,3-d]pyrimidine

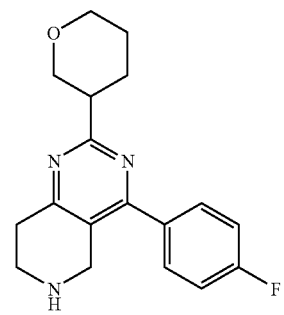

Example 125

4-(4-Fluoro-phenyl)-2-(tetrahydro-pyran-3-yl)-5,6,7,8-tetrahydro-pyrido[4,3-d]pyrimidine

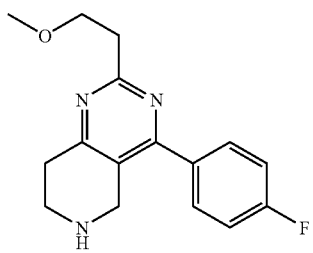

Example 126

4-(4-Fluoro-phenyl)-2-(2-methoxy-ethyl)-5,6,7,8-tetrahydro-pyrido[4,3-d]pyrimidine

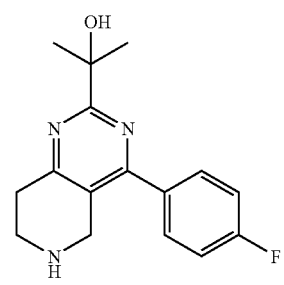

Example 127

2-[4-(4-Fluoro-phenyl)-5,6,7,8-tetrahydro-pyrido[4,3-d]pyrimidin-2-yl]-propan-2-ol

Example 130

3-[4-(4-Fluoro-phenyl)-5,6,7,8-tetrahydro-pyrido[4,3-d]pyrimidin-2-yl]-cyclohexanol

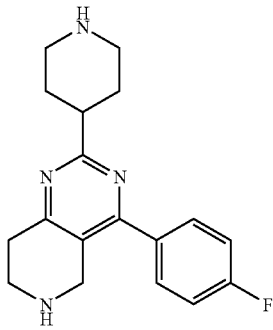

Example 128

4-(4-Fluoro-phenyl)-2-(1-methyl-1-phenyl-ethyl)-5,6,7,8-tetrahydro-pyrido[4,3-d]pyrimidine

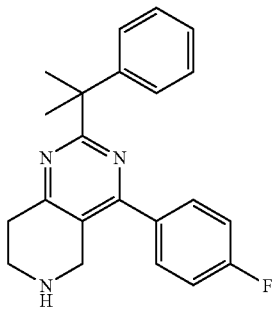

Example 131

4-(4-Fluoro-phenyl)-2-piperidin-4-yl-5,6,7,8-tetrahydro-pyrido[4,3-d]pyrimidine

Example 129

2-Cyclopent-3-enyl-4-(4-fluoro-phenyl)-5,6,7,8-tetrahydro-pyrido[4,3-d]pyrimidine

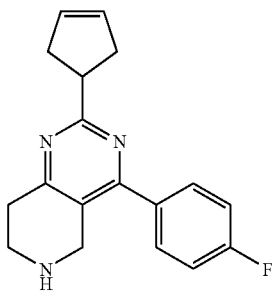

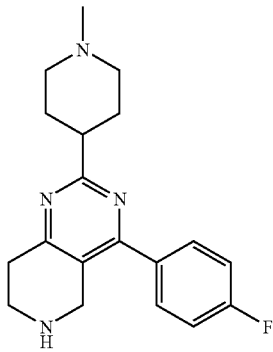

Example 132

4-(4-Fluoro-phenyl)-2-(1-methyl-piperidin-4-yl)-5,6,7,8-tetrahydro-pyrido[4,3-d]pyrimidine

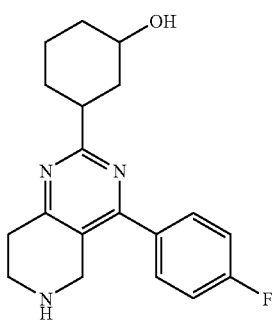

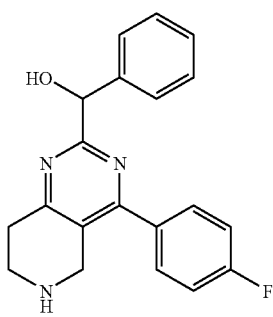

Example 133

[4-(4-Fluoro-phenyl)-5,6,7,8-tetrahydro-pyrido[4,3-d]pyrimidin-2-yl]-phenyl-methanol

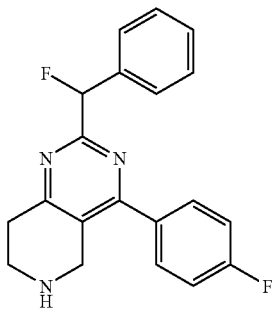

Example 134

4-(4-Fluoro-phenyl)-2-(fluoro-phenyl-methyl)-5,6,7,8-tetrahydro-pyrido[4,3-d]pyrimidine

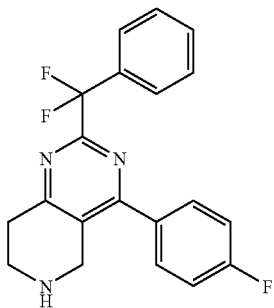

Example 135

2-(Difluoro-phenyl-methyl)-4-(4-fluoro-phenyl)-5,6,7,8-tetrahydro-pyrido[4,3-d]pyrimidine

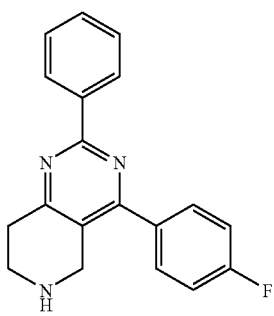

Example 136

4-(4-Fluoro-phenyl)-2-phenyl-5,6,7,8-tetrahydro-pyrido[4,3-d]pyrimidine

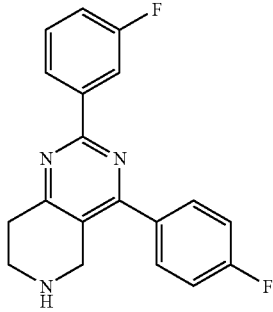

Example 137

4-(4-Fluoro-phenyl)-2-(3-fluoro-phenyl)-5,6,7,8-tetrahydro-pyrido[4,3-d]pyrimidine

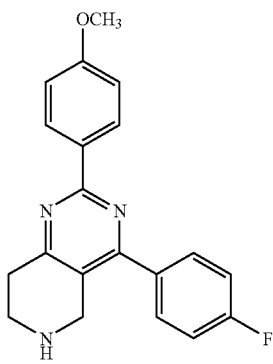

Example 138

4-(4-Fluoro-phenyl)-2-(4-methoxy-phenyl)-5,6,7,8-tetrahydro-pyrido[4,3-d]pyrimidine

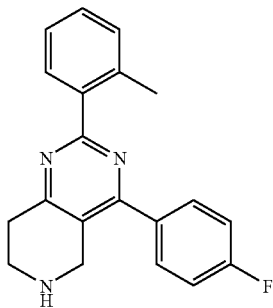

Example 139

4-(4-Fluoro-phenyl)-2-o-tolyl-5,6,7,8-tetrahydro-pyrido[4,3-d]pyrimidine

Example 142

4-(4-Fluoro-phenyl)-2-(1-methyl-cyclopropyl)-5,6,7,8-tetrahydro-pyrido[4,3-d]pyrimidine

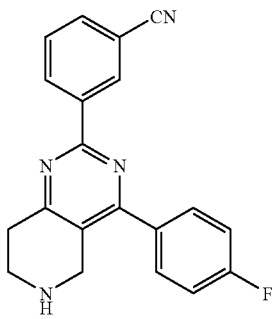

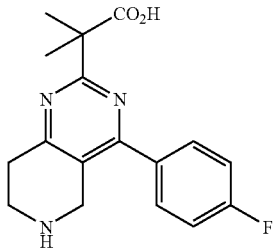

Example 140

3-[4-(4-Fluoro-phenyl)-5,6,7,8-tetrahydro-pyrido[4,3-d]pyrimidin-2-yl]-benzonitrile Example 143

2-[4-(4-Fluoro-phenyl)-5,6,7,8-tetrahydro-pyrido[4,3-d]pyrimidin-2-yl]-2-methyl-propionic acid

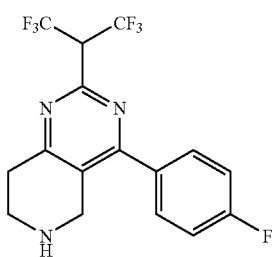

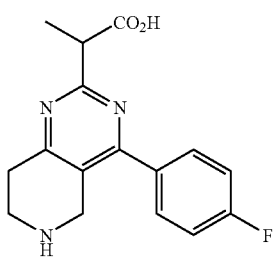

Example 141

4-(4-Fluoro-phenyl)-2-(2,2,2-trifluoro-1-trifluoromethyl-ethyl)-5,6,7,8-tetrahydro-pyrido[4,3-d]pyrimidine Example 144

2-[4-(4-Fluoro-phenyl)-5,6,7,8-tetrahydro-pyrido[4,3-d]pyrimidin-2-yl]-propionic acid

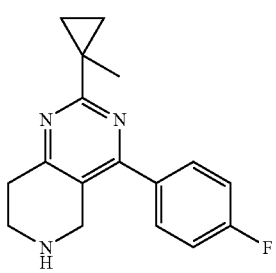

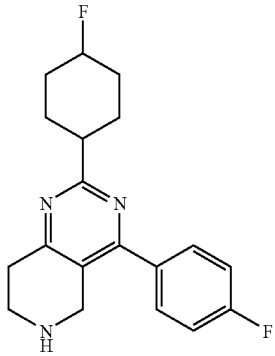

Example 145

2-(4-Fluoro-cyclohexyl)-4-(4-fluoro-phenyl)-5,6,7,8-tetrahydro-pyrido[4,3-d]pyrimidine

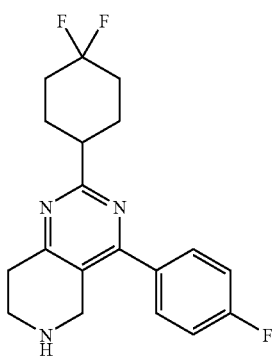

Example 146

2-(4,4-Difluoro-cyclohexyl)-4-(4-fluoro-phenyl)-5,6,7,8-tetrahydro-pyrido[4,3-d]pyrimidine

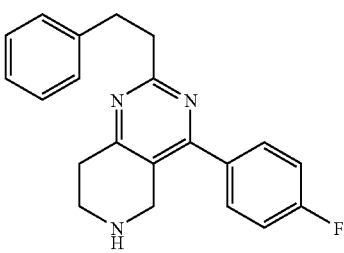

Example 147

4-(4-Fluoro-phenyl)-2-phenethyl-5,6,7,8-tetrahydro-pyrido[4,3-d]pyrimidine

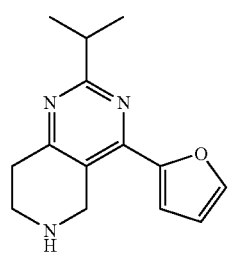

Example 148

4-Furan-2-yl-2-isopropyl-5,6,7,8-tetrahydro-pyrido[4,3-d]pyrimidine

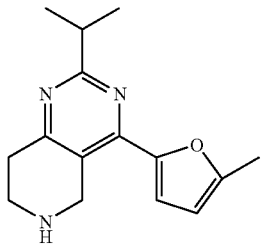

Example 149

2-Isopropyl-4-(5-methyl-furan-2-yl)-5,6,7,8-tetrahydro-pyrido[4,3-d]pyrimidine

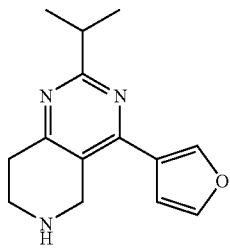

Example 150

4-Furan-3-yl-2-isopropyl-5,6,7,8-tetrahydro-pyrido[4,3-d]pyrimidine

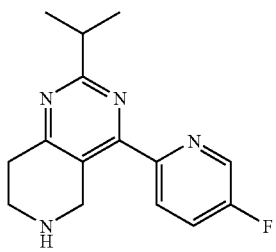

Example 151

4-(5-Fluoro-pyridin-2-yl)-2-isopropyl-5,6,7,8-tetrahydro-pyrido[4,3-d]pyrimidine

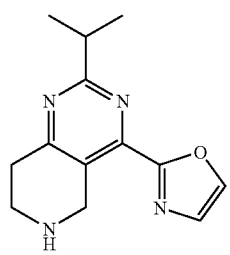

Example 152

2-Isopropyl-4-oxazol-2-yl-5,6,7,8-tetrahydro-pyrido[4,3-d]pyrimidine

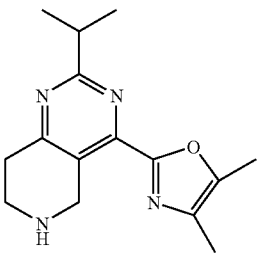

Example 153

4-(4,5-Dimethyl-oxazol-2-yl)-2-isopropyl-5,6,7,8-tetrahydro-pyrido[4,3-d]pyrimidine

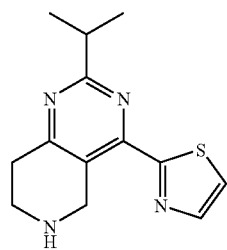

Example 154

2-Isopropyl-4-thiazol-2-yl-5,6,7,8-tetrahydro-pyrido[4,3-d]pyrimidine

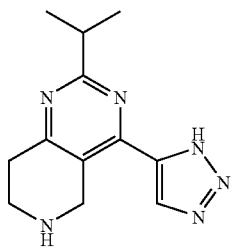

Example 155

2-Isopropyl-4-(3H-[1,2,3]triazol-4-yl)-5,6,7,8-tetrahydro-pyrido[4,3-d]pyrimidine

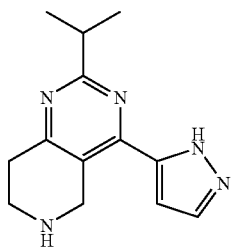

Example 156

2-Isopropyl-4-(2H-pyrazol-3-yl)-5,6,7,8-tetrahydro-pyrido[4,3-d]pyrimidine

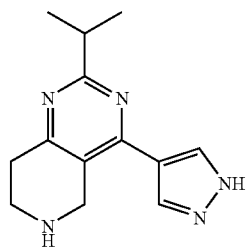

Example 157

2-Isopropyl-4-(1H-pyrazol-4-yl)-5,6,7,8-tetrahydro-pyrido[4,3-d]pyrimidine

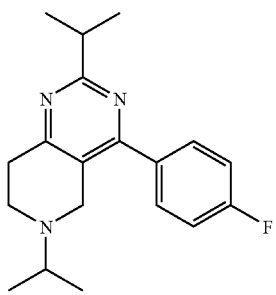

Example 158

4-(4-Fluoro-phenyl)-2,6-diisopropyl-5,6,7,8-tetrahydro-pyrido[4,3-d]pyrimidine

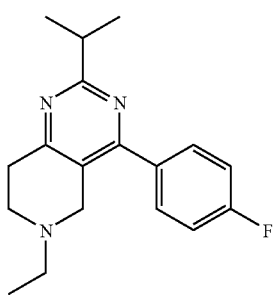

Example 159

6-Ethyl-4-(4-fluoro-phenyl)-2-isopropyl-5,6,7,8-tetrahydro-pyrido[4,3-d]pyrimidine

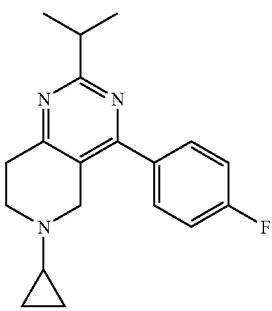

Example 160

6-Cyclopropyl-4-(4-fluoro-phenyl)-2-isopropyl-5,6,7,8-tetrahydro-pyrido[4,3-d]pyrimidine

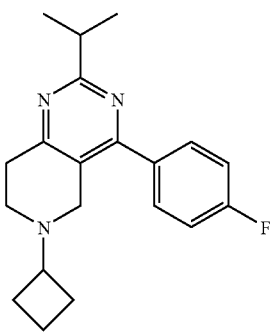

Example 161

6-Cyclobutyl-4-(4-fluoro-phenyl)-2-isopropyl-5,6,7,8-tetrahydro-pyrido[4,3-d]pyrimidine

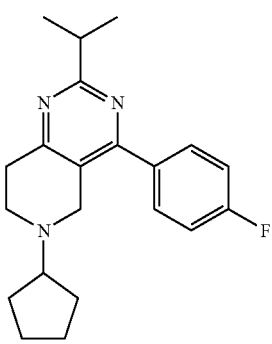

Example 162

6-Cyclopentyl-4-(4-fluoro-phenyl)-2-isopropyl-5,6,7,8-tetrahydro-pyrido[4,3-d]pyrimidine

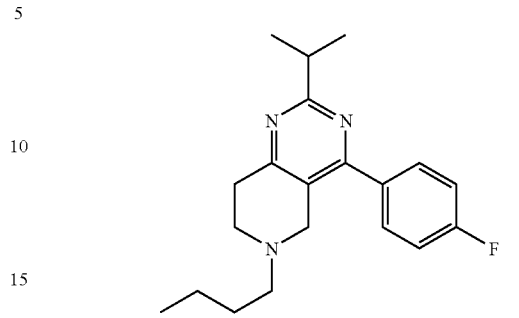

Example 163

6-Butyl-4-(4-fluoro-phenyl)-2-isopropyl-5,6,7,8-tetrahydro-pyrido[4,3-d]pyrimidine

Example 164

Alternative preparation of 4-(4-fluoro-phenyl)-2-isopropyl-5,6,7,8-tetrahydro-pyrido[4,3-d]pyrimidine Step A. 1-(3,4,5,6,3',6'-Hexahydro-2H,2'H-[1,4']bipyridinyl-1'-yl)-ethanone. A flask equipped with a Dean-Stark trap and a reflux condenser was charged with 1-acetyl-piperdin-4-one (100 g, 0.71 mol) and toluene (1 L). Piperidine (63.4 g, 0.75 mol) and p-toluenesulfonic acid monohydrate (0.27 g, 1.4 mmol, 0.2 mol %) were added, and the resulting solution was heated at reflux for 8 h. The mixture was cooled to rt and concentrated to give a crude product which was used directly in the next reaction.

Step B. 1-[5'-(4-Fluoro-benzoyl)-3,4,5,6,3',6'-hexahydro-2H,2'H-[1,4']bipyridinyl-1'-yl]-ethanone. A solution of crude 1-(3,4,5,6,3',6'-hexahydro-2H,2'H-[1,4']bipyridinyl-1'-yl)-ethanone in CH$_2$Cl$_2$ (1.5 L) was treated with Et$_3$N (108 mL, 0.78 mol) and then cooled to 0° C. A solution of 4-fluorobenzoyl chloride (107 g, 0.68 mol) in CH$_2$Cl$_2$ (150 mL) was added over 1 h. The reaction mixture was stirred at rt for 2 h, then was concentrated to give a crude material which was directly used on next reaction. HPLC: R$_T$=7.52 min. MS (ESI): exact mass calcd. for C$_{19}$H$_{23}$FN$_2$O$_2$, 330.17; m/z found, 331.0 [M+H]$^+$.

Step C. 1-[4-(4-Fluoro-phenyl)-2-isopropyl-7,8-dihydro-5H-pyrido[4,3-d]pyrimidin-6-yl]-ethanone. A solution of crude 1-[5'-(4-fluoro-benzoyl)-3,4,5,6,3',6'-hexahydro-2H,2'H-[1,4']bipyridinyl-1'-yl]-ethanone in t-amyl alcohol (1.5 L) was treated with Et$_3$N (108 mL, 0.78 mol) and 2-methyl propanimidamide hydrochloride (82.6 g, 0.67 mol). The reaction mixture was heated at reflux for 16 h and then was cooled to rt. The mixture was concentrated, and the residue was diluted with water (2 L) and extracted with EtOAc (2×). The combined organic layers were dried (MgSO$_4$) and concentrated to afford the crude title compound, which was used in next reaction without further purification. HPLC: R$_T$=8.11 min. MS (ESI): exact mass calcd. for C$_{18}$H$_{20}$FN$_3$O, 313.16; m/z found, 314.0 [M+H]$^+$. $^1$H NMR (CDCl$_3$; mixture of rotamers): 7.60-7.50 (m, 2H), 7.24-7.12 (m, 2H), 4.71 (s, 1.4H), 4.56 (s, 0.6H), 3.93 (t, J=6.2, 0.6H), 3.80 (t, J=6.2, 1.4H), 3.18 (sept, J=6.8, 1H), 3.07 (t, J=6.2, 1.4H), 3.02 (t, J=6.2, 0.6H), 2.15 (s, 2.1H), 2.00 (s, 0.9H), 1.34 (d, J=6.8, 6H).

Step D. A mixture of crude 1-[4-(4-fluoro-phenyl)-2-isopropyl-7,8-dihydro-5H-pyrido[4,3-d]pyrimidin-6-yl]-ethanone in 10% aq. HCl (800 mL) was heated at reflux for 2 h and then cooled to rt. The aqueous solution was washed with EtOAc (400 mL) and then was basified with NaOH pellets (~120 g) to pH>12. The basic solution was extracted with $CH_2Cl_2$ (2×500 mL). The combined organic layers were washed with 1 N NaOH (400 mL), dried ($MgSO_4$), and concentrated to give the crude product (100 g), which was used in the next reaction without further purification. HPLC: RT=6.89 min. MS (ESI): exact mass calcd. for $C_{16}H_{18}FN_3$, 271.15; m/z found, 271.9 [M+H]$^+$.

Example 165

4-(4-Fluoro-phenyl)-2-isopropyl-5,6,7,8-tetrahydro-pyrido[4,3-d]pyrimidine, citrate salt A solution of crude 4-(4-fluoro-phenyl)-2-isopropyl-5,6,7,8-tetrahydro-pyrido[4,3-d]pyrimidine (Example 164) in EtOH (1 L) was treated with citric acid (71 g, 0.37 mol). The solution was warmed to 50° C. to form a homogeneous solution, then was cooled to rt and stirred for 16 h. The mixture was diluted with $Et_2O$ (750 mL) and was stirred for 1 h. The precipitated white solid was collected by filtration and washed with cold EtOH (ca. 100 mL). The white solid was dried in a vacuum oven at 55° C. to give an off-white solid (157.3 g, 50% overall yield). HPLC: RT=6.86 min. MS (ESI): exact mass calcd. for $C_{16}H_{18}FN_3$, 271.15; m/z found, 271.9 [M+H]$^+$. $^1$H NMR ($D_2O$): 7.49-7.43 (m, 2H), 7.27-7.19 (m, 2H), 4.28 (s, 2H), 3.60 (t, J=6.5, 2H), 3.20 (t, J=6.5, 2H), 3.11 (sept, J=6.9, 1H), 2.77 (d, J=15.4, 2H), 2.65 (d, J=15.4, 2H), 1.23 (d, J=6.9, 6H). $^{13}$C NMR ($D_2O$): 176.59, 172.69, 171.99, 162.59 (d, $J_{C-F}$=11.6), 160.67, 159.41, 129.42, 128.53 (d, $J_{C-F}$=8.8), 115.91, 113.89 (d, $J_{C-F}$=22.4), 71.78, 41,61, 40.10, 38.77, 34.78, 25.33, 18.64.

The compounds in Examples 166-167 were prepared using methods analogous to those described in the preceding examples.

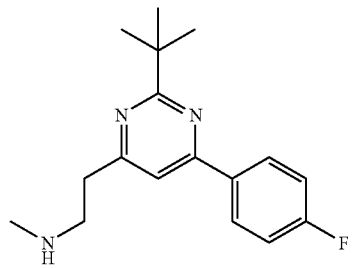

Example 166

{2-[2-tert-Butyl-6-(4-fluoro-phenyl)-pyrimidin-4-yl]-ethyl}-methyl-amine

MS (ESI): exact mass calcd. for $C_{17}H_{22}FN_3$, 287.18; m/z found, 288.7 [M+H]$^+$.

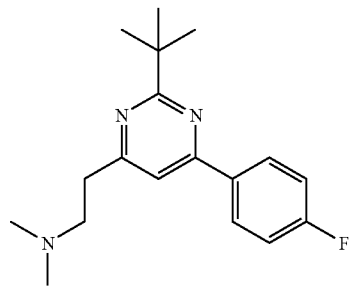

Example 167

{2-[2-tert-Butyl-6-(4-fluoro-phenyl)-pyrimidin-4-yl]-ethyl}-dimethyl-amine

MS (ESI): exact mass calcd. for $C_{18}H_{24}FN_3$, 301.20; m/z found, 302.7 [M+H]$^+$.

Assay Methods

In Vitro Pharmacology

Stock drug solutions (10 mM) were prepared in DMSO (the final assay concentration of DMSO not exceeding 0.4%). Drug dilutions were prepared in assay buffer.

Sigmoidal inhibition curves were generated and fitted by nonlinear regression analysis (GraphPad Prism). $K_i$ values were calculated according to the Cheng and Prussoff equation (Biochem. Pharmacol. 1973, 22, 3099-3108), $IC_{50}/(1+[S]/K_d)$, where the following values were used: 5-$HT_7$ ([S]=1 nM; $K_d$=0.42); 5-$HT_{2A}$ ([S]=1 nM; $K_d$=0.4 nM); 5-$HT_{2B}$ ([S]=4 nM; $K_d$=3.5 nM); 5-$HT_{2C}$ ([S]=3 nM; $K_d$=3 nM); 5-$HT_6$ ([S]=1.7 nM; $K_d$=1.7 nM).

Data obtained for compounds tested in Assays 1-4 are presented in Table 1 below.

1. Affinity for 5-$HT_7$ Receptor Binding Sites

The affinity of the compounds described in this invention for the 5-$HT_7$ receptor binding site was evaluated by single competition radioligand binding assay. The assay was performed on membranes prepared from HEK-293 cells that had been subjected to stable transfection with the rat 5-$HT_{7a}$ receptor (GB: NM022938). Cells were scraped from the culture plates, suspended in Tris-HCl 50 mM pH 7.5 and collected through centrifugation (1000 rpm for 5 min). The cell pellets were homogenized (Polytron, 15 s, setting 5) in 50 mM Tris-HCl (pH 7.5), 5 mM EDTA. Following centrifugation (15,000 rpm for 25 min), membranes (135 µg protein/mL) were resuspended in the same buffer and incubated for 60 min at RT with 1 nM [$^3$H]5-CT in the presence of increasing concentration of test compounds. Nonspecific binding was defined in the presence of 10 µM 5-HT. Incubation was stopped by rapid filtration using the cell harvester (Packard). Radioactivity was counted in a TopCount-NXT (Packard). Experiments were conducted in triplicate.

2. Affinity for 5-$HT_{2A}$ Receptor Binding Sites

The affinity of the compounds for the rat 5-$HT_{2A}$ receptor was evaluated by competitive radioligand binding assay using [$^3$H]ketanserine as the radioligand. The assay was performed on membranes from rat cortex (Schotte, A. et al. Psychopharmacology 1996, 124, 57-73). Brain tissue (rat cortex) was homogenized in 20 volumes per wet weight tissue of Tris-HCl buffer (50 mM, pH 7.4). The total membrane fraction was collected by centrifugation and washed by subsequent centrifugation runs (25 min at 25,000 g at 4° C.). Membranes were re-suspended in Tris-HCl buffer (50 mM, pH 7.4) containing 1 nM [$^3$H]ketanserin. Non-specific binding was estimated in the presence of 10 μM risperidone. The incubation was terminated by rapid filtration over Whatman GF/B filters pre-soaked in 0.1% polyethylenimine, and one washing step with 1 mL ice-cold Tris-HCl buffer, pH 7.4.

3. Affinity for 5HT$_2$ Receptor Binding Sites

Receptor binding was performed using the human recombinant 5-HT$_{2A}$ (GB: X57830), 5-HT$_{2B}$ (GB: Z36748) and 5-HT$_{2C}$ (GB: M81778) receptors. The affinity of the compounds for the 3 different human 5-HT$_2$ receptor subtypes was evaluated by competitive radioligand binding assays using [$^3$H]ketanserin (h5-HT$_{2A}$) or [$^3$H]mesulergine (h5-HT$_{2B}$ and h5-HT$_{2C}$). The assays were performed on membranes prepared from NIH3T3 stably transfected with h5-HT$_{2A}$ or CHO stably transfected with h5-HT$_{2B}$ and h5-HT$_{2C}$.

4. Affinity for 5-HT$_6$ Receptor Binding Sites

Receptor binding was performed using the human recombinant 5-HT$_6$ (GB: BC0794995) receptor. The affinity of the compounds for the human 5-HT$_6$ receptor was evelauated by competitive radioligand binding assays using [$^3$H]LSD. The assays were preformed on membranes prepared from HEK-293 stably transfected with h5-HT$_6$. Non-specific binding was estimated in the presence of 1 μM clozapine.

TABLE 1

| | Binding Affinities (nM) | | | | |
|---|---|---|---|---|---|
| Ex. | $K_i$ 5-HT$_7$ | $K_i$ 5-HT$_{2A}$ | $K_i$ 5-HT$_{2B}$ | $K_i$ 5-HT$_{2C}$ | $K_i$ 5-HT$_6$ |
| 1 | 540 | 4 | 70 | 90 | NT |
| 2 | >10000 | 20 | 5000 | 510 | NT |
| 3 | >10000 | 11 | 2250 | 1020 | >10000 |
| 4 | >10000 | 20 | 250 | 200 | NT |
| 5 | >10000 | 13 | 350 | 250 | NT |
| 6 | >10000 | 50 | 200 | 300 | NT |
| 7 | >10000 | 25 | 900 | 900 | NT |
| 8 | 1000 | 20 | 1000 | 320 | 200 |
| 9 | 5000 | 1350 | >10000 | 7500 | NT |
| 10 | >10000 | 200 | >10000 | 5000 | NT |
| 11 | >10000 | 100 | >10000 | 2000 | NT |
| 12 | >10000 | 300 | >10000 | 5000 | NT |
| 13 | >10000 | 12.5 | 2200 | 1000 | NT |
| 14 | >10000 | 30 | 4000 | 4000 | NT |
| 15 | >10000 | 1000 | >10000 | >10000 | NT |
| 16 | >10000 | 2000 | >10000 | >10000 | NT |
| 17 | >10000 | 4 | 250 | 70 | NT |
| 18 | 525 | 10 | 80 | 60 | 330 |
| 19 | >10000 | 100 | 140 | 200 | NT |
| 20 | >10000 | 700 | 1200 | >10000 | NT |
| 21 | >10000 | 25 | 1185 | 1170 | >10000 |
| 22 | >10000 | 32 | 500 | 1300 | NT |
| 23 | >10000 | 500 | >10000 | >10000 | NT |
| 24 | >10000 | 240 | >10000 | >10000 | NT |
| 25 | >10000 | 300 | >10000 | >10000 | NT |
| 26 | >10000 | 300 | >10000 | >10000 | NT |
| 27 | >10000 | 60 | >10000 | >10000 | NT |
| 28 | >10000 | 100 | 400 | 3000 | NT |
| 29 | >10000 | 240 | 1600 | 2000 | >10000 |
| 30 | >10000 | 800 | 1000 | 2500 | NT |
| 31 | >10000 | 70 | 2000 | >10000 | NT |
| 32 | >10000 | 2000 | >10000 | >10000 | NT |
| 33 | >10000 | >10000 | >10000 | >10000 | NT |
| 34 | >10000 | 150 | 400 | 1000 | NT |
| 35 | 500 | 70 | 400 | 2000 | NT |
| 36 | >10000 | >10000 | >10000 | >10000 | NT |
| 37 | >10000 | 40 | 400 | 1000 | NT |
| 38 | >10000 | 40 | 50 | 800 | NT |
| 39 | >10000 | 150 | >10000 | >10000 | NT |
| 40 | >10000 | 500 | >10000 | >10000 | NT |
| 41 | >10000 | 2000 | 5000 | 5000 | NT |
| 42 | >10000 | 120 | >10000 | >10000 | NT |
| 43 | >10000 | 200 | >10000 | >10000 | NT |
| 44 | >10000 | 400 | 500 | 1000 | NT |
| 45 | >10000 | >10000 | >10000 | >10000 | NT |
| 46 | 120 | 14 | 30 | 200 | 100 |
| 47 | 30 | 2.5 | 1 | 22 | 12 |
| 48 | 40 | 20 | 3 | 100 | 24 |
| 49 | 300 | 50 | 25 | 400 | 200 |
| 50 | 240 | 3.7 | 20 | 80 | 260 |
| 51 | >10000 | 470 | 140 | 9000 | NT |
| 52 | >10000 | 725 | 1150 | 9000 | NT |
| 53 | >10000 | 1000 | >10000 | >10000 | NT |
| 54 | 5000 | 0.55 | 30 | 20 | 30 |
| 55 | 35 | 0.42 | 2.5 | 16 | 8.5 |
| 56 | 180 | 0.80 | 22 | 38 | 30 |
| 57 | 550 | 0.70 | 40 | 50 | 80 |
| 58 | >10000 | 2 | 40 | 30 | 100 |
| 59 | 100 | 1.5 | 7.8 | 29 | 20 |
| 60 | 400 | 6 | 10 | 60 | 60 |
| 61 | 250 | 1.9 | 15 | 35 | 20 |
| 62 | 5275 | 0.75 | 21 | 21 | 27 |
| 63 | >10000 | 1.5 | 52 | 46 | 60 |
| 64 | >10000 | 10 | 1300 | 70 | 1300 |
| 65 | >10000 | 20 | 300 | 570 | >10000 |
| 66 | 300 | 8 | 30 | 145 | NT |
| 67 | 5400 | 56 | 80 | 495 | NT |
| 68 | >10000 | 80 | 660 | 7100 | NT |
| 69 | >10000 | 140 | >10000 | 650 | 7100 |
| 70 | >10000 | 117 | >10000 | 3733 | 250 |
| 71 | >10000 | 1027 | 4333 | 3583 | 300 |
| 72 | >10000 | 130 | >10000 | >10000 | NT |
| 73 | >10000 | 140 | >10000 | >10000 | NT |
| 74 | >10000 | 47 | 1900 | >10000 | NT |
| 75 | 5000 | 70 | 3000 | >10000 | NT |
| 76 | 150 | 9 | 315 | 75 | 300 |
| 77 | 22 | 15 | 200 | 130 | 400 |
| 78 | 400 | 25 | 900 | 380 | NT |
| 79 | 300 | 115 | 435 | 900 | NT |
| 80 | >10000 | 11 | 158 | 940 | 2800 |
| 81 | >10000 | 25 | 450 | 6000 | NT |
| 82 | >10000 | 2 | 500 | 20 | 230 |
| 83 | >10000 | 30 | 1000 | 300 | 230 |
| 84 | >10000 | 14 | 400 | 5000 | NT |
| 85 | >10000 | 82 | 1150 | >10000 | NT |
| 86 | 9000 | 100 | 4100 | >10000 | NT |
| 87 | >10000 | 600 | 2000 | >10000 | NT |
| 88 | 550 | 13 | 60 | 185 | NT |
| 89 | >10000 | 25 | 40 | 1400 | NT |
| 90 | 2300 | 17 | 130 | 1000 | NT |
| 91 | >10000 | 75 | 200 | 9000 | NT |
| 92 | >10000 | 300 | >10000 | >10000 | NT |
| 93 | >10000 | >10000 | >10000 | >10000 | NT |
| 94 | >10000 | >10000 | >10000 | >10000 | NT |
| 95 | >10000 | 2000 | >10000 | >10000 | NT |
| 96 | >10000 | >10000 | >10000 | >10000 | NT |
| 97 | >10000 | >10000 | >10000 | >10000 | NT |
| 98 | >10000 | >10000 | >10000 | >10000 | NT |
| 99 | >10000 | >10000 | >10000 | >10000 | NT |
| 100 | >10000 | 14 | 900 | 300 | NT |
| 101 | >10000 | 400 | >10000 | >10000 | NT |
| 102 | >10000 | 20 | 150 | 230 | 370 |
| 103 | >10000 | 40 | 1000 | 1000 | NT |
| 104 | >10000 | 700 | 500 | 3000 | NT |
| 105 | >10000 | 40 | 100 | 400 | NT |
| 106 | >10000 | 90 | 6300 | >10000 | NT |
| 107 | >10000 | 12 | 275 | 500 | 4000 |
| 108 | >10000 | 18 | 42 | 1000 | NT |
| 109 | >10000 | 400 | >10000 | >10000 | >10000 |
| 110 | >10000 | 220 | 1200 | 4000 | NT |
| 111 | >10000 | 300 | 3500 | >10000 | NT |
| 112 | >10000 | 130 | >10000 | >10000 | NT |
| 113 | >10000 | 650 | >10000 | >10000 | NT |

TABLE 1-continued

| | Binding Affinities (nM) | | | | |
|---|---|---|---|---|---|
| Ex. | $K_i$ 5-HT$_7$ | $K_i$ 5-HT$_{2A}$ | $K_i$ 5-HT$_{2B}$ | $K_i$ 5-HT$_{2C}$ | $K_i$ 5-HT$_6$ |
| 114 | >10000 | 35 | 300 | 1000 | NT |
| 115 | 5000 | 1000 | 5000 | >10000 | NT |
| 116 | >10000 | 2000 | >10000 | >10000 | NT |
| 117 | >10000 | 50 | 1000 | 4000 | NT |
| 166 | NT | 11 | 18 | 170 | NT |
| 167 | 450 | 7 | 14 | 200 | NT |

NT = not tested

5. In Vitro Functional Assay for 5-HT$_2$ Receptor (Intracellular Calcium)

In vitro functional properties of these compounds on the different 5-HT$_2$ receptor substypes were determined using fluorometric imaging plate reader (FLIPR) based calcium assay as previously described (Porter, R. H. et al. Br. *J. Pharmacol.* 1999, 128, 13-20; Jerman, J. C. et al. *Eur. J. Pharmacol.* 2001, 414, 23-30). The 5-HT$_2$ receptors are linked to the Gq family of G proteins and to subsequent activation of phospholipase C, induction of phosphoinositide metabolism and to an increase in intracelular calcium concentration. The same cell lines as described in the previous section (receptor binding) were used for the FLIPR experiments. Data obtained for compounds tested are presented in Table 2.

TABLE 2

| Ex. | pK$_b$ 5-HT$_{2A}$ | pK$_b$ 5-HT$_{2B}$ | pK$_b$ 5-HT$_{2C}$ |
|---|---|---|---|
| 13 | 7.1 | 5 | NT |
| 17 | 8.1 | 5.4 | NT |
| 18 | 7.6 | 6.7 | NT |
| 21 | 7.5 | 5 | 5 |
| 50 | 8.3 | 8.3 | NT |
| 57 | 8.2 | 6.9 | NT |
| 62 | 8.8 | 7.3 | NT |
| 63 | 7.8 | 6.3 | NT |
| 64 | 7.1 | 5 | NT |
| 69 | 6 | 5 | NT |
| 76 | 7 | 5 | NT |
| 78 | 7.1 | 5 | NT |
| 82 | 8.1 | 5.4 | NT |
| 100 | 7 | 5 | NT |

NT = not tested

What is claimed is:

1. A compound that is 4-(4-fluoro-phenyl)-2-isopropyl-5,6,7,8-tetrahydro-pyrido[4,3-d]pyrimidine or a pharmaceutically acceptable salt thereof.

2. A compound of claim 1 isotopically-labelled to be detectable by PET or SPECT.

3. The compound of claim 1 wherein said pharmaceutically acceptable salt is selected from the group consisting of hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate.

4. The compound of claim 3 wherein said pharmaceutically acceptable salt is hydrochloride.

5. A pharmaceutical composition comprising a pharmaceutically acceptable carrier and a therapeutically effective amount of a compound that is 4-(4-fluoro-phenyl)-2-isopropyl-5,6,7,8-tetrahydro-pyrido [4,3-d]pyrimidine or a pharmaceutically acceptable salt thereof.

6. The composition of claim 5 wherein said pharmaceutically acceptable salt is selected from the group consisting of hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate.

7. The composition of claim 6 wherein said pharmaceutically acceptable salt is hydrochloride.

8. The compound of claim 3 wherein said pharmaceutically acceptable salt is citrate.

9. The composition of claim 6 wherein said pharmaceutically acceptable salt is citrate.

10. A compound which is a citric acid salt of 4-(4-fluorophenyl)-2-isopropyl-5,6,7,8-tetrahydro-pyrido [4,3-d]pyrimidine.

11. A pharmaceutical composition comprising a pharmaceutically acceptable carrier and a therapeutically effective amount of a compound that is a citric acid salt of 4-(4-fluorophenyl)-2-isopropyl-5,6,7,8-tetrahydro-pyrido [4,3-d]pyrimidine.

* * * * *